United States Patent
Gotoh et al.

(10) Patent No.: US 9,527,870 B2
(45) Date of Patent: Dec. 27, 2016

(54) LIQUID CRYSTAL COMPOUND, LIQUID CRYSTAL COMPOSITION AND LIQUID CRYSTAL DISPLAY DEVICE

(71) Applicants: JNC CORPORATION, Tokyo (JP); JNC PETROCHEMICAL CORPORATION, Tokyo (JP)

(72) Inventors: Yasuyuki Gotoh, Tokyo (JP); Masahide Kobayashi, Ichihara (JP)

(73) Assignees: JNC CORPORATION, Tokyo (JP); JNC PETROCHEMICAL CORPORATION, Tokyo (JP)

( * ) Notice: Subject to any disclaimer, the term of this patent is extended or adjusted under 35 U.S.C. 154(b) by 0 days.

(21) Appl. No.: 14/749,158

(22) Filed: Jun. 24, 2015

(65) Prior Publication Data

US 2015/0368272 A1    Dec. 24, 2015

(30) Foreign Application Priority Data

Jun. 24, 2014 (JP) .................. 2014-129217
Aug. 4, 2014 (JP) .................. 2014-158794

(51) Int. Cl.
*G02F 1/1333* (2006.01)
*C07D 519/00* (2006.01)
(Continued)

(52) U.S. Cl.
CPC ............. *C07D 519/00* (2013.01); *C07C 25/18* (2013.01); *C07C 25/22* (2013.01); *C07C 25/24* (2013.01);
(Continued)

(58) Field of Classification Search
CPC ... C07D 519/00; C07D 239/26; C07D 319/06; C07D 309/04; C07D 213/26; C07D 413/04; C07C 321/28; C07C 255/50; C07C 331/28; C07C 25/18; C07C 25/22; C07C 25/24; C09K 19/3458; C09K 19/3098; C09K 19/322; C09K 19/3444; C09K 2019/3422; C09K 2019/3427; C09K 2019/122–2019/124; C09K 2019/3016; C09K 2019/3018; C09K 2019/3019; C09K 2019/3025; C09K 2019/3027; C09K 2019/325; C09K 2019/326; C09K 2019/3425
(Continued)

(56) References Cited

U.S. PATENT DOCUMENTS 5,045,229 A    9/1991 Bartmann et al. ....... 252/299.01
5,728,319 A    3/1998 Matsui et al. ........... 252/299.63
(Continued)

FOREIGN PATENT DOCUMENTS

DE    40 06 921 A1    9/1990
EP    1 081 123 A2    3/2001
(Continued)

*Primary Examiner* — Geraldina Visconti
(74) *Attorney, Agent, or Firm* — Stein IP, LLC

(57) ABSTRACT

To provide a liquid crystal compound satisfying at least one physical property such as high stability to light, a high clearing point, low minimum temperature of a liquid-crystal phase, small viscosity, suitable optical anisotropy, large dielectric anisotropy, a large dielectric constant in a minor axis direction, a suitable elastic constant, excellent compatibility with other liquid crystal compounds. The compound is represented by formula (1-1):

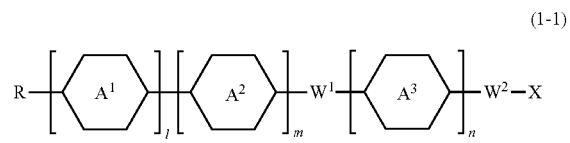

(1-1)

for example, R is alkyl having 1 to 10 carbons or alkoxy having 1 to 9 carbons, rings $A^1$ to $A^3$ are 1,4-cyclohexylene, 1,4-phenylene, or 1,4-phenylene in which at least one hydrogen is replaced by halogen; X is halogen, $-CF_3$ or $-OCF_3$; l is 1, and m, n is 0 or 1; $W^1$ is a group represented by formula (1a) or (1b);

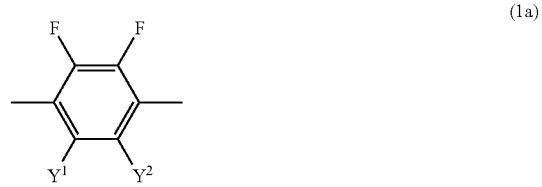

(1a)

(1b)

$W^2$ is a group represented by formula (1c) or (1d);

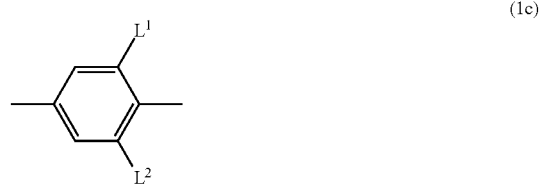

(1c)

(Continued)

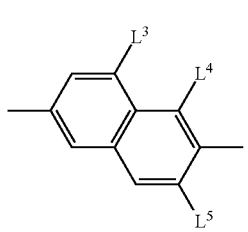

(1d)

$Y^1$ to $Y^2$ are hydrogen, $Y^3$ to $Y^5$ and $L^1$ to $L^5$ are fluorine.

18 Claims, No Drawings

(51) Int. Cl.
  C09K 19/34 (2006.01)
  C09K 19/30 (2006.01)
  C09K 19/32 (2006.01)
  C07C 25/18 (2006.01)
  C07D 239/26 (2006.01)
  C07D 319/06 (2006.01)
  C07C 321/28 (2006.01)
  C07C 255/50 (2006.01)
  C07C 331/28 (2006.01)
  C07C 25/22 (2006.01)
  C07D 309/04 (2006.01)
  C07D 213/26 (2006.01)
  C07D 413/04 (2006.01)
  C07C 25/24 (2006.01)
  C09K 19/12 (2006.01)

(52) U.S. Cl.
  CPC .......... *C07C 255/50* (2013.01); *C07C 321/28* (2013.01); *C07C 331/28* (2013.01); *C07D 213/26* (2013.01); *C07D 239/26* (2013.01); *C07D 309/04* (2013.01); *C07D 319/06* (2013.01); *C07D 413/04* (2013.01); *C09K 19/3098* (2013.01); *C09K 19/322* (2013.01); *C09K 19/3444* (2013.01); *C09K 19/3458* (2013.01); *C09K 2019/122* (2013.01); *C09K 2019/123* (2013.01); *C09K 2019/124* (2013.01); *C09K 2019/3016* (2013.01); *C09K 2019/3018* (2013.01); *C09K 2019/3019* (2013.01); *C09K 2019/3025* (2013.01); *C09K 2019/3027* (2013.01); *C09K 2019/325* (2013.01); *C09K 2019/326* (2013.01); *C09K 2019/3422* (2013.01); *C09K 2019/3425* (2013.01); *C09K 2019/3427* (2013.01)

(58) Field of Classification Search
  USPC ............ 252/299.01, 299.6, 299.61; 349/182
  See application file for complete search history.

(56) References Cited

U.S. PATENT DOCUMENTS

| 6,007,740 | A | 12/1999 | Andou et al. ............ 252/299.63 |
| 8,187,494 | B2* | 5/2012 | Kobayashi ........... C07D 309/06 |
|  |  |  | 252/299.01 |
| 2002/0028306 | A1 | 3/2002 | Kirsch et al. .................. 428/1.1 |

FOREIGN PATENT DOCUMENTS

| JP | H 10-204016 A | 8/1998 |
| JP | 2001-139511 A | 5/2001 |
| JP | 2002-323415 A | 11/2002 |
| JP | 2002-327175 A | 11/2002 |
| WO | WO 96/11897 A1 | 4/1996 |

\* cited by examiner

LIQUID CRYSTAL COMPOUND, LIQUID CRYSTAL COMPOSITION AND LIQUID CRYSTAL DISPLAY DEVICE

CROSS-REFERENCE TO RELATED APPLICATIONS

This application claims the benefit of priority to Japanese Application No. 2014-129217, filed Jun. 24, 2014, and Japanese Application No. 2014-158794, filed Aug. 4, 2014 in the Japanese Patent Office. All disclosures of the documents named above are incorporated herein by reference.

BACKGROUND OF THE INVENTION

Technical Field

The invention relates to a liquid crystal compound, a liquid crystal composition and a liquid crystal display device. More specifically, the invention relates to a compound having a difluoromethyleneoxy group, a liquid crystal composition containing the compound and having a nematic phase, and a liquid crystal display device including the composition.

The liquid crystal display device is widely utilized for a display of a personal computer, a television and so forth. The device utilizes optical anisotropy, dielectric anisotropy and so forth of the liquid crystal compound. As an operating mode of the liquid crystal display device, a phase change (PC) mode, a twisted nematic (TN) mode, a super twisted nematic (STN) mode, a bistable twisted nematic (BTN) mode, an electrically controlled birefringence (ECB) mode, an optically compensated bend (OCB) mode, an in-plane switching (IPS) mode, a vertical alignment (VA) mode, a fringe field switching (FFS) mode, a polymer sustained alignment (PSA) mode and so forth are known.

In such a liquid crystal display device, a liquid crystal composition having suitable physical properties is used. In order to further improve characteristics of the liquid crystal display device, the liquid crystal compound contained in the composition preferably has physical properties described in (1) to (8) below.

(1) High stability to heat, light and so forth,
(2) a high clearing point,
(3) a low minimum temperature of a liquid crystal phase,
(4) small viscosity ($\eta$),
(5) suitable optical anisotropy ($\Delta n$),
(6) large dielectric anisotropy ($\Delta \in$),
(7) a suitable elastic constant (K)
(8) excellent compatibility with other liquid crystal compounds, and
(9) a large dielectric constant ($\in \perp$) in a minor axis direction.

An effect of the physical properties of the liquid crystal compound on the characteristics of the device is described below. A compound having the high stability to heat, light and so forth as described in (1) increases a voltage holding ratio of the device. Therefore, a service life of the device becomes long. A compound having the high clearing point as described in (2) extends a temperature range in which the device can be used. A compound having the low minimum temperature of the liquid crystal phase such as the nematic phase or a smectic phase, particularly the low minimum temperature of the nematic phase as described in (3) also extends the temperature range in which the device can be used. A compound having the small viscosity as described in (4) shortens response time of the device.

A compound having the suitable optical anisotropy as described in (5) improves contrast of the device. A compound having a large optical anisotropy or a small optical anisotropy, more specifically, the suitable optical anisotropy according to a design of the device is required. A compound having the large optical anisotropy is suitable when the response time is shortened by decreasing a cell gap of the device. A compound having the large dielectric anisotropy as described in (6) decreases a threshold voltage of the device. Therefore, a power consumption of the device becomes small. Meanwhile, a compound having a small dielectric anisotropy shortens the response time of the device by decreasing the viscosity of the composition.

With regard to (7), a compound having a large elastic constant shortens the response time of the device. A compound having a small elastic constant decreases the threshold voltage of the device. Accordingly, the suitable elastic constant is needed depending on the characteristics to be improved. A compound having the excellent compatibility with other liquid crystal compounds as described in (8) is preferred. The reason is that the physical properties of the composition are adjusted by mixing compounds having different physical properties.

Further, an improvement of a transmittance in the liquid crystal composition has been strongly required in connection with a demand for achieving a low power consumption and a high definition in the liquid crystal display device in recent years. Above all, the transmittance in the liquid crystal composition used for an FFS mode liquid crystal display device is known to be correlated with the dielectric constant ($\in \perp$) in the minor axis direction of the liquid crystal composition, and therefore a liquid crystal compound having the large dielectric constant in the minor axis direction as described in (9) is preferred.

A variety of liquid crystal compounds each having a $CF_2O$ group have so far been prepared as the compound having the large dielectric anisotropy, and some of the compounds have been practically used. However, in the above compounds, the dielectric constant in the minor axis direction is far from sufficiently large. Under such circumstances, desire has been expressed for development of a compound having excellent physical properties and a suitable balance with regard to the physical properties (1) to (9) above, above all, a compound simultaneously having the large dielectric anisotropy ($\Delta \in$) and the large dielectric constant in the minor axis direction.

CITATION LIST

Patent Literature

Patent literature No. 1: WO 1996/011897 A.
Patent literature No. 2: JP H10-204016 A.
Patent literature No. 3: DE 4006921 A.
Patent literature No. 4: JP 2001-139511 A.
Patent literature No. 5: JP 2002-80452 A.
Patent literature No. 6: JP 2002-327175 A.

SUMMARY OF THE INVENTION

Technical Problem

A first object of the invention is to provide a liquid crystal compound satisfying at least one of physical properties such as a high stability to light, a high clearing point, a low minimum temperature of a liquid crystal phase, a small viscosity, a suitable optical anisotropy, a large dielectric anisotropy, a large dielectric constant in a minor axis direction, a suitable elastic constant and an excellent compatibility with other liquid crystal compounds, and in particular, to provide a compound satisfying the large dielectric anisotropy and the large dielectric constant in the minor axis direction. A second object is to provide a composition containing the compound and satisfying at least one of physical properties such as a high maximum temperature of a nematic phase, a low minimum temperature of the nematic phase, a small viscosity, a suitable optical anisotropy, a large dielectric anisotropy, a large dielectric constant in a minor axis direction and a suitable elastic constant. The object is to provide a liquid crystal composition having a suitable balance regarding at least two of the physical properties. A third object is to provide a liquid crystal display device including the composition and satisfying a wide temperature range in which the device can be used, a short response time, a large voltage holding ratio, a low threshold voltage, a large contrast ratio and a long service life.

Solution to Problem

The invention concerns a compound represented by formula (1-1), a liquid crystal composition containing the compound, and a liquid crystal display device including the composition.

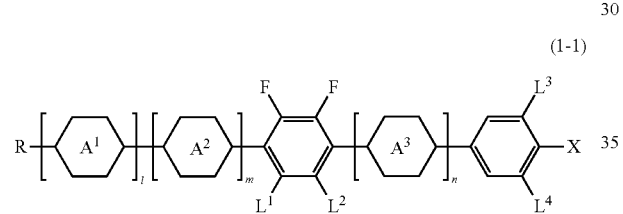

(1-1)

wherein, in formula (1-1),

R is hydrogen or alkyl having 1 to 10 carbons, and in the alkyl, at least one of —$CH_2$— may be replaced by —O— or —S—, at least one of —$(CH_2)_2$— may be replaced by —CH=CH—, and in the groups, at least one of hydrogen may be replaced by halogen;

ring $A^1$, ring $A^2$ and ring $A^3$ are independently 1,4-cyclohexylene, 1,4-cyclohexenylene, tetrahydropyran-2,5-diyl, 1,3-dioxane-2,5-diyl, 2,6,7-trioxabicyclo[2.2.2]octane-1,4-diyl, pyrimidine-2,5-diyl, pyridine-2,5-diyl, naphthalene-2,6-diyl, decahydronaphthalene-2,6-diyl, 1,2,3,4-tetrahydronaphthalene-2,6-diyl, 1,4-phenylene or 1,4-phenylene in which at least one of hydrogen is replaced by halogen;

$W^1$ is a group represented by formula (1a) or formula (1b);

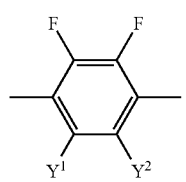

(1a)

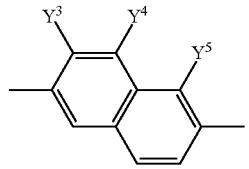

(1b)

wherein, in formula (1a) and formula (1b), $Y^1$ and $Y^2$ are independently hydrogen, chlorine or fluorine, $Y^3$, $Y^4$ and $Y^5$ are independently hydrogen, fluorine or chlorine, and at least two of $Y^3$, $Y^4$ and $Y^5$ is fluorine or chlorine; and in formula (1-1), $W^2$ is a group represented by formula (1c) or formula (1d);

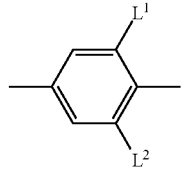

(1c)

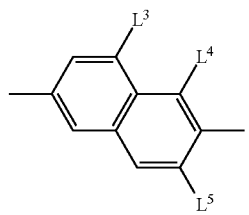

(1d)

wherein, in formula (1c) and formula (1d), $L^1$, $L^2$, $L^3$, $L^4$ and $L^5$ are independently hydrogen, fluorine or chlorine; and in formula (1-1), X is halogen, —C≡N, —N=C=S, —$SF_5$, —$CF_3$, —$CF_2H$, —$CFH_2$, —$OCF_3$, —$OCF_2H$, —$OCFH_2$ or alkyl having 1 to 10 carbons, and in the alkyl, at least one of —$CH_2$— may be replaced by —O— or —S—, at least one of —$(CH_2)_2$— may be replace by CH=CH—, and in the groups, at least one of hydrogen may be replaced by halogen; and l, m and n are 0 or 1, and a sum of l, m and n is 0, 1 or 2;

in which, when a sum of l and m is 1 and n is 0, at least one of $W^1$ and $W^2$ is a group represented by formula (1b) or formula (1d), or at least one of l piece of ring $A^1$ and m pieces of ring $A^2$ is 1,4-cyclohexylene, 1,4-cyclohexenylene, tetrahydropyran-2,5-diyl, 1,3-dioxane-2,5-diyl, 2,6,7-trioxabicyclo[2.2.2]octane-1,4-diyl, pyrimidine-2,5-diyl, pyridine-2,5-diyl, naphthalene-2,6-diyl, decahydronaphthalene-2,6-diyl, 1,2,3,4-tetrahydronaphthalene-2,6-diyl, or 1,4-phenylene in which at least one of hydrogen is replaced by halogen.

The invention also concerns use of the liquid crystal composition in a liquid crystal display device.

Advantageous Effects of the Invention

A first advantage of the invention is to provide a liquid crystal compound satisfying at least one of physical properties such as a high stability to light, a high clearing point, a low minimum temperature of a liquid crystal phase, a small viscosity, a suitable optical anisotropy, a large dielectric anisotropy, a suitable elastic constant and an excellent compatibility with other liquid crystal compounds. In particular, the advantage is to provide a compound simultaneously having the large dielectric anisotropy, and the large dielectric constant in a minor axis direction. A second advantage is provide a composition containing the compound and satisfying at least one of physical properties such as a high maximum temperature of a nematic phase, a low minimum temperature of the nematic phase, a small viscosity, a suitable optical anisotropy, a large dielectric anisotropy, a large dielectric constant in a minor axis direction and a suitable elastic constant. A third advantage is to provide a liquid crystal display device including the composition and satisfying a wide temperature range in which the device can be used, a short response time, a large voltage holding ratio, a low threshold voltage, a large contrast ratio and a long service life.

DESCRIPTION OF THE EMBODIMENTS

Usage of terms herein is as described below. A liquid crystal compound is a generic term for a compound having a liquid crystal phase such as a nematic phase or a smectic phase, and also a compound having no liquid crystal phase but being added for adjusting physical properties such as a maximum temperature, a minimum temperature, viscosity and dielectric anisotropy. The compound has a six-membered ring such as 1,4-cyclohexylene and 1,4-phenylene, and rod-like molecular structure. A liquid crystal composition is prepared by mixing such liquid crystal compounds. A ratio (content) of the liquid crystal compounds is expressed in terms of weight percent (% by weight) based on the weight of the liquid crystal composition. An additive such as a polymerizable compound, a polymerization initiator, an optically active compound, an antioxidant, an ultraviolet light absorber, a light stabilizer, a heat stabilizer, an antifoaming agent and a dye is added to the liquid crystal composition, when necessary. A ratio (content) of the additive is expressed in terms of weight percent (% by weight) based on the weight of the liquid crystal composition in a manner similar to the ratio of the liquid crystal compound. Weight parts per million (ppm) may be occasionally used. A Liquid crystal display device is a generic term for a liquid crystal display panel and a liquid crystal display module. The liquid crystal compound, the liquid crystal composition and the liquid crystal display device may be occasionally abbreviated as "compound," "composition" and "device," respectively. A clearing point is a transition temperature between the liquid crystal phase and an isotropic phase in the liquid crystal compound. The minimum temperature of the liquid crystal phase is a transition temperature between a solid and the liquid crystal phase (the smectic phase, the nematic phase or the like) in the liquid crystal compound. A higher limit of a temperature range of the nematic phase is a transition temperature between the nematic phase and the isotropic phase in the liquid crystal composition, and may be occasionally abbreviated as "maximum temperature." A lower limit of the temperature range of the nematic phase may be occasionally abbreviated as "minimum temperature."

A compound represented by formula (1) may be occasionally abbreviated as "compound (1)." The abbreviation may also apply occasionally to a compound represented by formula (2) or the like. In formulas (1) to (15), a symbol such as $A^1$, $B^1$, $C^1$ or the like surrounded by a hexagonal shape respectively corresponds to ring $A^1$, ring $B^1$, ring $C^1$ or the like. A symbol of terminal group $R^{11}$ is used for a plurality of compounds. In the compounds, two groups represented by two of arbitrary $R^{11}$ may be identical or different. For example, in one case, $R^{11}$ of compound (2) is ethyl and $R^{11}$ of compound (3) is ethyl. In another case, $R^{11}$ of compound (2) is ethyl and $R^{11}$ of compound (3) is propyl. A same rule further applies to a symbol of any other terminal group, ring or the like. In formula (5), when i is 2, two of ring $C^1$ exists. In the compound, two groups represented by two of ring $C^1$ may be identical or different. A same rule also applies to arbitrary two groups when i is larger than 2. A same rule further applies to a symbol of any other ring, bonding group or the like.

An expression "at least one of "A" may be replaced by "B"" means that a position of "A" when the number of "A" is 1 is arbitrary, and that positions thereof can be selected without restriction when the number of "A" is 2 or more. An expression "at least one of A may be replaced by B, C or D" means a case where at least one of A is replaced by B, a case where at least one of A is replaced by C, and a case where at least one of A is replaced by D, and also a case where a plurality of A are replaced by at least two of B, C and D. For example, alkyl in which at least one of —$CH_2$— may be replaced by —O— or —CH═CH— includes alkyl, alkenyl, alkoxy, alkoxyalkyl, alkoxyalkenyl and alkenyloxyalkyl. In addition, a case where replacement of two successive —$CH_2$— by —O— results in forming —O—O— is not preferred. In the alkyl or the like, a case where replacement of —$CH_2$— of a methyl group (—$CH_2$—H) by —O— results in forming —O—H is not preferred, either.

Then, 2-fluoro-1,4-phenylene means two divalent groups described below. In a chemical formula, fluorine may be leftward (L) or rightward (R). A same rule also applies to an asymmetrical divalent ring such as tetrahydropyran-2,5-diyl.

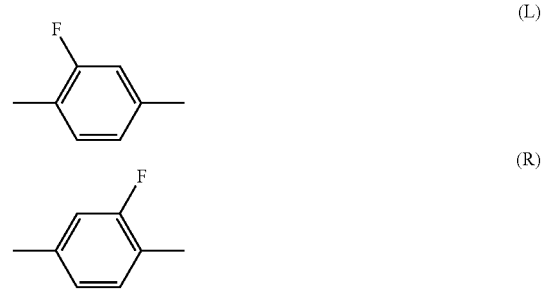

The invention includes the content described in items 1 to 19 below.

Item 1. A compound represented by formula (1-1):

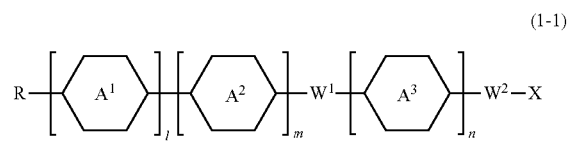

wherein, in formula (1-1),
R is hydrogen or alkyl having 1 to 10 carbons, and in the alkyl, at least one of —$CH_2$— may be replaced by —O— or —S—, at least one of —$(CH_2)_2$— may be replaced by —CH═CH—, and in the groups, at least one of hydrogen may be replaced by halogen;

ring $A^1$, ring $A^2$ and ring $A^3$ are independently 1,4-cyclohexylene, 1,4-cyclohexenylene, tetrahydropyran-2,5-diyl, 1,3-dioxane-2,5-diyl, 2,6,7-trioxabicyclo[2.2.2]octane-1,4-diyl, pyrimidine-2,5-diyl, pyridine-2,5-diyl, naphthalene-2,6-diyl, decahydronaphthalene-2,6-diyl, 1,2,3,4-tetrahydronaphthalene-2,6-diyl, 1,4-phenylene, or 1,4-phenylene in which at least one of hydrogen is replaced by halogen;

$W^1$ is a group represented by formula (1a) or formula (1b);

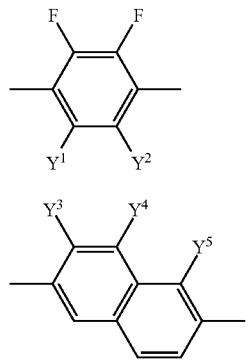

(1a)

(1b)

wherein, in formula (1a) and formula (1b), $Y^1$ and $Y^2$ are independently hydrogen, chlorine or fluorine, $Y^3$, $Y^4$ and $Y^5$ are independently hydrogen, fluorine or chlorine, and at least two of $Y^3$, $Y^4$ and $Y^5$ is fluorine or chlorine; and in formula (1-1), $W^2$ is a group represented by formula (1c) or formula (1d);

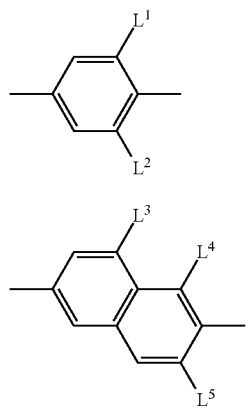

(1c)

(1d)

wherein, in formula (1c) and formula (1d), $L^1$, $L^2$, $L^3$, $L^4$ and $L^5$ are independently hydrogen, fluorine or chlorine; and in formula (1-1), X is halogen, —C≡N, —N═C═S, —SF$_5$, —CF$_3$, —CF$_2$H, —CFH$_2$, —OCF$_3$, —OCF$_2$H, —OCFH$_2$ or alkyl having 1 to 10 carbons, and in the alkyl, at least one of —CH$_2$— may be replaced by —O— or —S—, at least one of —(CH$_2$)$_2$— may be replace by —CH═CH—, and in the groups, at least one of hydrogen may be replaced by halogen; and l, m and n are 0 or 1, and a sum of l, m and n is 0, 1 or 2;

in which, when a sum of l and m is 1 and n is 0, at least one of $W^1$ and $W^2$ is a group represented by formula (1b) or formula (1d), or at least one of one piece of ring $A^1$ and m pieces of ring $A^2$ is 1,4-cyclohexylene, 1,4-cyclohexenylene, tetrahydropyran-2,5-diyl, 1,3-dioxane-2,5-diyl, 2,6,7-trioxabicyclo[2.2.2]octane-1,4-diyl, pyrimidine-2,5-diyl, pyridine-2,5-diyl, naphthalene-2,6-diyl, decahydronaphthalene-2,6-diyl, 1,2,3,4-tetrahydronaphthalene-2,6-diyl, or 1,4-phenylene in which at least one of hydrogen is replaced by halogen.

Item 2. The compound according to item 1, represented by formula (1-2):

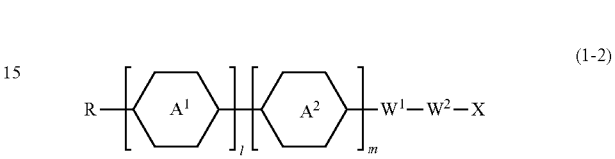

(1-2)

wherein, in formula (1-2),

R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^1$ and ring $A^2$ are independently 1,4-cyclohexylene, 1,4-cyclohexenylene, 1,3-dioxane-2,5-diyl, 2,6,7-trioxabicyclo[2.2.2]octane-1,4-diyl, pyrimidine-2,5-diyl, naphthalene-2,6-diyl, 2-fluoro-1,4-phenylene, 3-fluoro-1,4-phenylene, 2,3-difluoro-1,4-phenylene or 3,5-difluoro-1,4-phenylene;

$W^1$ is a group represented by formula (1a) or formula (1b);

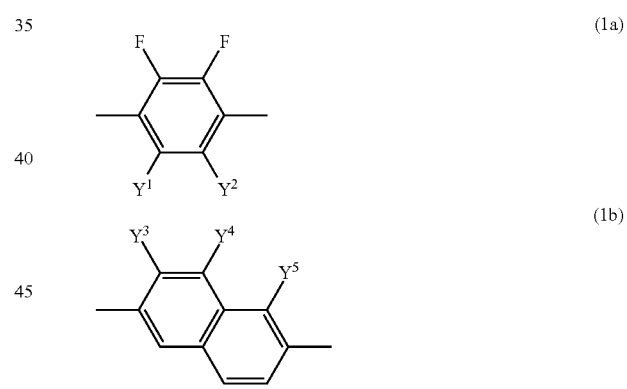

(1a)

(1b)

wherein, in formula (1a) and formula (1b), $Y^1$ and $Y^2$ are independently hydrogen, chlorine or fluorine, $Y^3$, $Y^4$ and $Y^5$ are independently hydrogen, fluorine or chlorine, and at least two of $Y^3$, $Y^4$ and $Y^5$ is fluorine or chlorine; and in formula (1-2), $W^2$ is a group represented by formula (1c) or formula (1d);

(1c)

-continued (1d)

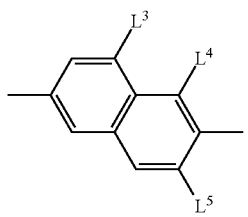

wherein, in formula (1c) and formula (1d), $L^1$, $L^2$, $L^3$, $L^4$ and $L^5$ are independently hydrogen, fluorine or chlorine; and in formula (1-2), X is fluorine, chlorine, —C≡N, —N=C=S, —SF$_5$, —CH$_2$F, —CHF$_2$, —CF$_3$, —(CH$_2$)$_2$—F, —CH$_2$CF$_3$, —CF$_2$CF$_3$, —(CH$_2$)$_3$—F, —(CH$_2$)$_2$—CF$_3$, —(CF$_2$)$_3$—F, —(CH$_2$)$_4$—F, —(CH$_2$)$_3$—CF$_3$, —(CF$_2$)$_4$—F, —(CF$_2$)$_5$—F, —(CF$_2$)$_6$—F, —(CF$_2$)$_7$—F, —OCH$_2$F, —OCHF$_2$, —OCF$_3$, —O—(CH$_2$)$_2$—F, —OCH$_2$CF$_3$, —OCF$_2$CF$_3$, —O—(CH$_2$)$_3$—F, —O—(CH$_2$)$_2$—CF$_3$, —O—(CF$_2$)$_3$—F, —O(CH$_2$)$_4$—F, —O—(CH$_2$)$_3$—CF$_3$, —O—(CF$_2$)$_4$—F, —O—(CF$_2$)$_5$—F, —O—(CF$_2$)$_6$—F, —CH=CHF, —CH=CF$_2$, —CF=CHF, —CH=CHCH$_2$F, —CH=C—CF=CF$_2$HCF$_3$, —CF=CHCF$_3$, —CF=CFCF$_3$, —(CH$_2$)$_2$—CH=CF$_2$, —(CH$_2$)$_2$—CF=CF$_2$, —(CH$_2$)$_2$—CH=CHCF$_3$, —(CH$_2$)$_2$—CF=CHCF$_3$ or —(CH$_2$)$_2$—CF=CFCF$_3$; and l and m are 0 or 1, and a sum of l and m is 0, 1 or 2;

in which, when a sum of l and m is 1, at least one of $W^1$ and $W^2$ is a group represented by formula (1b) or formula (1d), or at least one of ring $A^1$ and ring $A^2$ is 1,4-cyclohexylene, 1,4-cyclohexenylene, 1,3-dioxane-2,5-diyl, 2,6,7-trioxabicyclo[2.2.2]octane-1,4-diyl, pyrimidine-2,5-diyl, naphthalene-2,6-diyl, 2-fluoro-1,4-phenylene, 2,3-difluoro-1,4-phenylene or 3,5-difluoro-1,4-phenylene.

Item 3. The compound according to item 1, represented by formula (1-3):

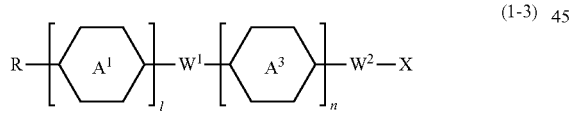

(1-3)

wherein, in formula (1-3),

R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^1$ is 1,4-cyclohexylene, 1,4-cyclohexenylene, 1,3-dioxane-2,5-diyl, 2,6,7-trioxabicyclo[2.2.2]octane-1,4-diyl, pyrimidine-2,5-diyl, naphthalene-2,6-diyl, 2-fluoro-1,4-phenylene, 3-fluoro-1,4-phenylene, 2,3-difluoro-1,4-phenylene or 3,5-difluoro-1,4-phenylene;

ring $A^3$ is 1,4-cyclohexylene, 1,4-cyclohexenylene, 1,3-dioxane-2,5-diyl, 2,6,7-trioxabicyclo[2.2.2]octane-1,4-diyl, pyrimidine-2,5-diyl, naphthalene-2,6-diyl, 1,4-phenylene, 2-fluoro-1,4-phenylene, 3-fluoro-1,4-phenylene, 2,3-difluoro-1,4-phenylene or 3,5-difluoro-1,4-phenylene;

$W^1$ is a group represented by formula (1a) or formula (1b);

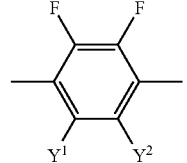

(1a)

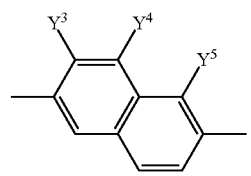

(1b)

wherein, in formula (1a) and formula (1b), $Y^1$ and $Y^2$ are independently hydrogen, chlorine or fluorine, $Y^3$, $Y^4$ and $Y^5$ are independently hydrogen, fluorine or chlorine, and at least two of $Y^3$, $Y^4$ and $Y^5$ is fluorine or chlorine; and in formula (1-3), $W^2$ is a group represented by formula (1c) or formula (1d);

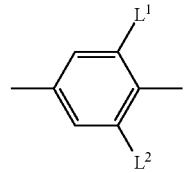

(1c)

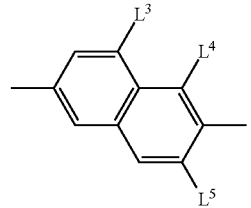

(1d)

wherein, in formula (1c) and formula (1d), $L^1$, $L^2$, $L^3$, $L^4$ and $L^5$ are independently hydrogen, fluorine or chlorine; and in formula (1-3), X is fluorine, chlorine, —C≡N, —N=C=S, —SF$_5$, —CH$_2$F, —CHF$_2$, —CF$_3$, —(CH$_2$)$_2$—F, —CH$_2$CF$_3$, —CF$_2$CF$_3$, —(CH$_2$)$_3$—F, (CH$_2$)$_2$—CF$_3$, —(CF$_2$)$_3$—F, —(CH$_2$)$_4$—F, —(CH$_2$)$_3$—CF$_3$, —(CF$_2$)$_4$—F, —(CF$_2$)$_5$—F, —(CF$_2$)$_6$—F, —(CF$_2$)$_7$—F, —OCH$_2$F, —OCHF$_2$, —OCF$_3$, —O—(CH$_2$)$_2$—F, —OCH$_2$CF$_3$, —OCF$_2$CF$_3$, —O—(CH$_2$)$_3$—F, —O—(CH$_2$)$_2$—CF$_3$, —O—(CF$_2$)$_3$—F, —O(CH$_2$)$_4$—F, —O—(CH$_2$)$_3$—CF$_3$, —O—(CF$_2$)$_4$—F, —O—(CF$_2$)$_5$—F, —O—(CF$_2$)$_6$—F, —CH=CHF, —CH=CF$_2$, —CF=CHF, —CF=CF$_2$, —CH=CHCH$_2$F, —CH=CHCF$_3$, —CF=CHCF$_3$, —CF=CFCF$_3$, —(CH$_2$)$_2$—CH=CF$_2$, —(CH$_2$)$_2$—CF=CF$_2$, —(CH$_2$)$_2$—CH=CHCF$_3$, —(CH$_2$)$_2$—CF=CHCF$_3$ or —(CH$_2$)$_2$—CF=CFCF$_3$; and l and n are 0 or 1, and a sum of l and n is 0, 1 or 2.

Item 4. The compound according to item 1, represented by formula (1-4):

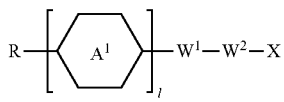

wherein, in formula (1-4),

R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^1$ is independently 1,4-cyclohexylene, 1,4-cyclohexenylene, 1,3-dioxane-2,5-diyl, pyrimidine-2,5-diyl, naphthalene-2,6-diyl, 2-fluoro-1,4-phenylene, 3-fluoro-1,4-phenylene or 2,3-difluoro-1,4-phenylene;

$W^1$ is a group represented by formula (1a) or formula (1b);

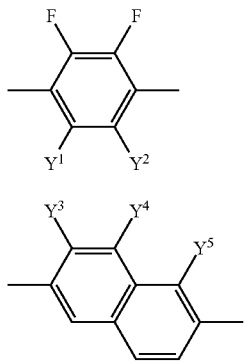

wherein, in formula (1c) and formula (1d), $Y^1$ and $Y^2$ are independently hydrogen, chlorine or fluorine, $Y^3$, $Y^4$ and $Y^5$ are independently hydrogen, fluorine or chlorine, and at least two of $Y^3$, $Y^4$ and $Y^5$ is fluorine or chlorine; and in formula (1-4), $W^2$ is a group represented by formula (1c) or formula (1d);

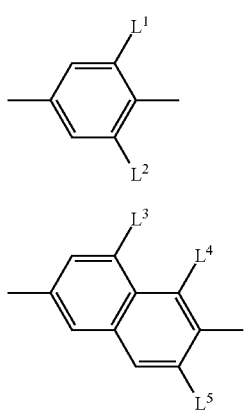

wherein, in formula (1c) and formula (1d), $L^1$, $L^2$, $L^3$, $L^4$ and $L^5$ are independently hydrogen, fluorine or chlorine; and in formula (1-4), X is fluorine, —C≡N, —N=C=S, —SF$_5$, —CF$_3$, —CHF$_2$, —CH$_2$F, —OCF$_3$, —OCHF$_2$ or —OCH$_2$F; and l is 0 or 1.

Item 5. The compound according to item 1, represented by formula (1-5):

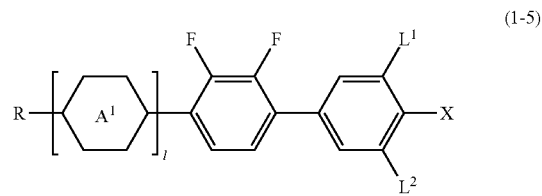

wherein, in formula (1-5),

R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^1$ is 1,4-cyclohexylene, 1,4-cyclohexenylene, 1,3-dioxane-2,5-diyl, pyrimidine-2,5-diyl, naphthalene-2,6-diyl, 1,4-phenylene, 2-fluoro-1,4-phenylene, 3-fluoro-1,4-phenylene or 2,3-difluoro-1,4-phenylene;

$L^1$ and $L^2$ are independently hydrogen or fluorine;

X is fluorine, —C≡N, —N=C=S, —SF$_5$, —CF$_3$, —CHF$_2$, —CH$_2$F, —OCF$_3$, —OCHF$_2$ or —OCH$_2$F; and l is 0 or 1.

Item 6. The compound according to item 1, represented by formulas (1-6-1) to (1-6-5):

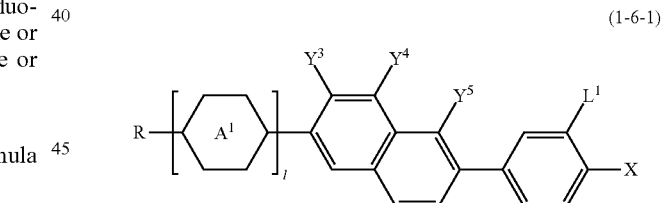

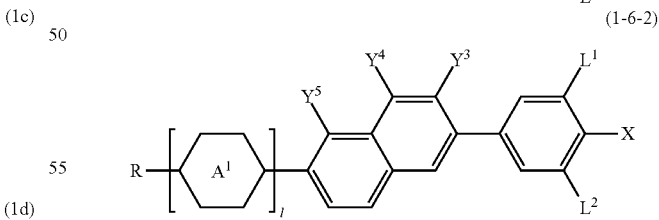

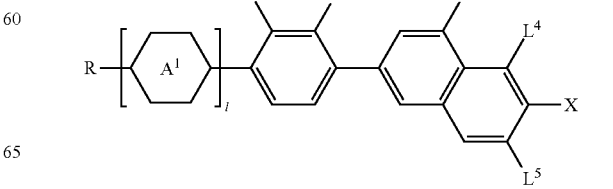

-continued (1-6-4)

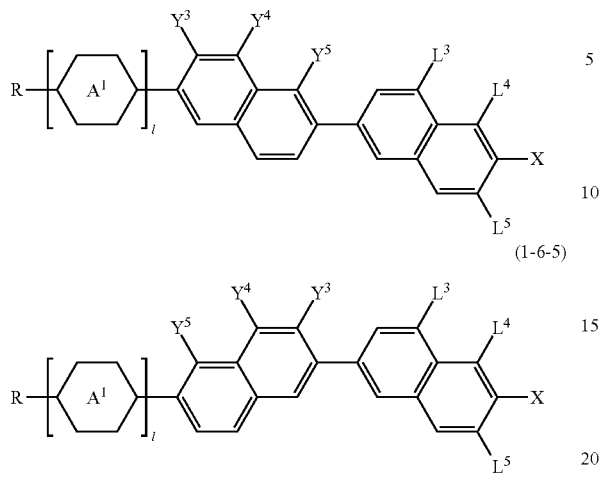

(1-6-5)

wherein, in formulas (1-6-1) to (1-6-5),

R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^1$ is 1,4-cyclohexylene, 1,4-cyclohexenylene, 1,3-dioxane-2,5-diyl or pyrimidine-2,5-diyl;

$Y^3$, $Y^4$ and $Y^5$ are independently hydrogen, fluorine or chlorine and at least two of $Y^3$, $Y^4$ and $Y^5$ is fluorine or chlorine;

$L^1$, $L^2$, $L^3$, $L^4$ and $L^5$ are independently hydrogen, fluorine or chlorine;

X is fluorine, —C≡N, —CF$_3$ or —OCF$_3$; and l is 0 or 1.

Item 7. The compound according to item 1, represented by formula (1-7):

(1-7)

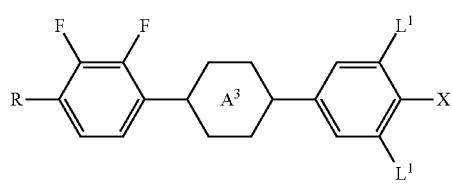

wherein, in formula (1-7),

R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^3$ is 1,4-cyclohexylene, 1,4-cyclohexenylene, 1,3-dioxane-2,5-diyl, pyrimidine-2,5-diyl, naphthalene-2,6-diyl, 1,4-phenylene, 2-fluoro-1,4-phenylene or 2,3-difluoro-1,4-phenylene;

$L^1$ and $L^2$ are independently hydrogen or fluorine; and

X is fluorine, —C≡N, —N=C=S, —SF$_5$, —CF$_3$, —CHF$_2$, —CH$_2$F, —OCF$_3$, —OCHF$_2$ or —OCH$_2$F.

Item 8. The compound according to item 1, represented by any one of formulas (1-8-1) to (1-8-5):

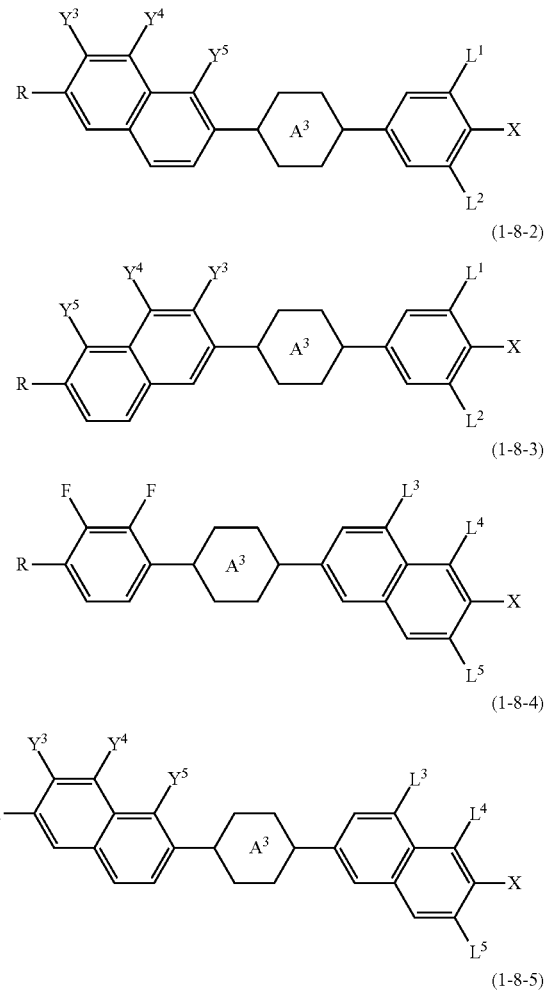

wherein, in formulas (1-8-1) to (1-8-5),

R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^3$ is 1,4-cyclohexylene, 1,4-cyclohexenylene, 1,3-dioxane-2,5-diyl, pyrimidine-2,5-diyl, 1,4-phenylene, 2-fluoro-1,4-phenylene or 2,3-difluoro-1,4-phenylene;

$Y^3$, $Y^4$ and $Y^5$ are independently hydrogen, fluorine or chlorine, and at least two of $Y^3$, $Y^4$ and $Y^5$ is fluorine or chlorine;

$L^1$, $L^2$, $L^3$, $L^4$ and $L^5$ are independently hydrogen, fluorine or chlorine; and X is fluorine, —C≡N, —CF$_3$ or —OCF$_3$.

Item 9. The compound according to item 1, represented by any one of formulas (1-9-1) to (1-9-12):

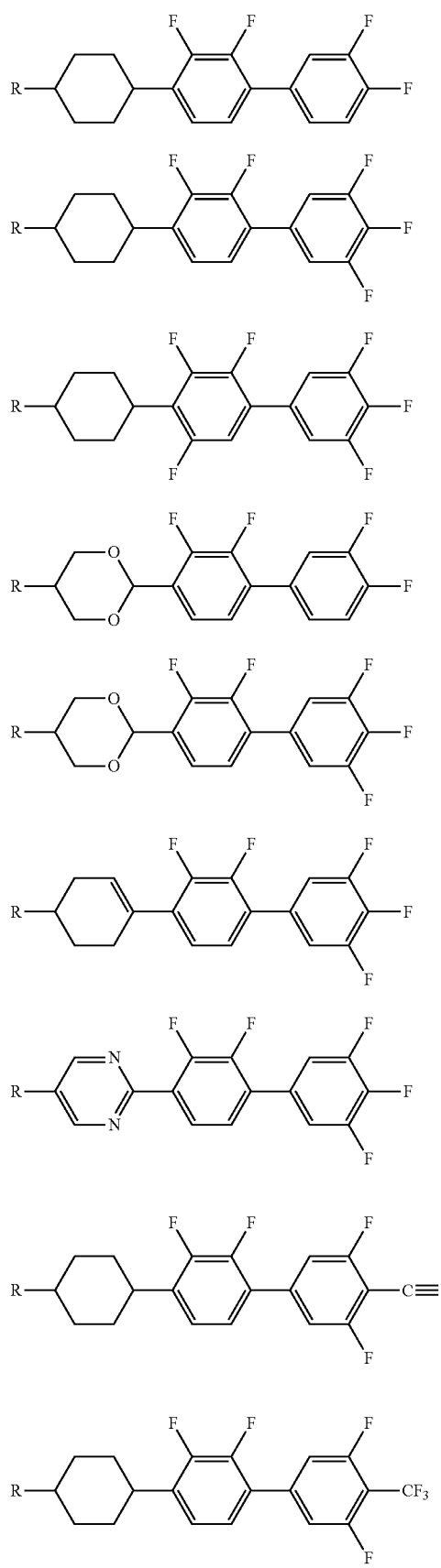
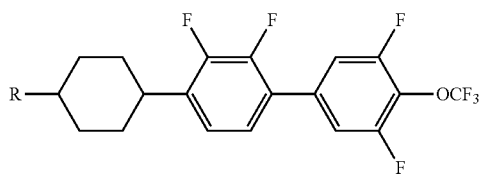
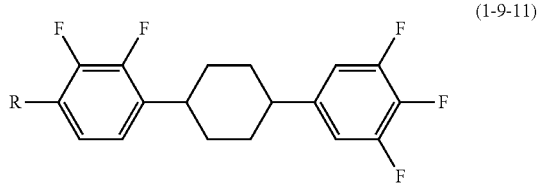
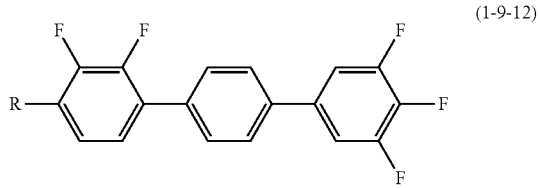
wherein, in formulas (1-9-1) to (1-9-12),
R is independently alkyl having 1 to 10 carbons, alkenyl having 2 to 10 carbons and alkoxy having 1 to 9 carbons.
Item 10. The compound according to item 1, represented by any one of formulas (1-10-1) to (1-10-12):
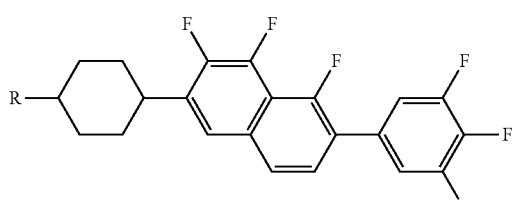
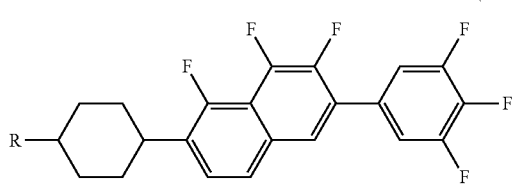
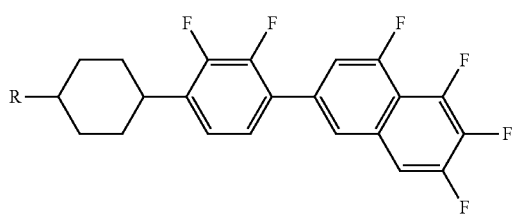

(1-10-4)
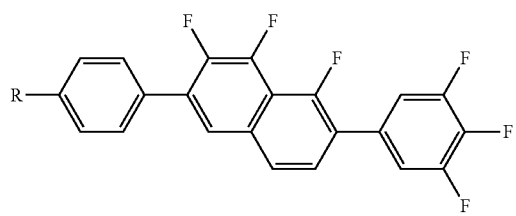

(1-10-5)
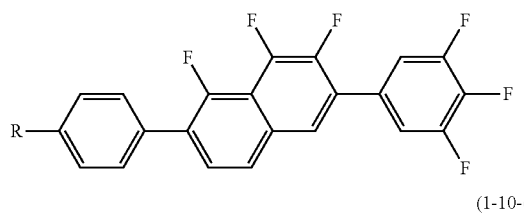

(1-10-6)
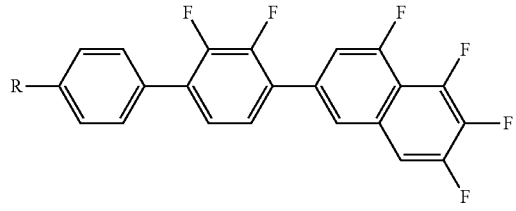

(1-10-7)
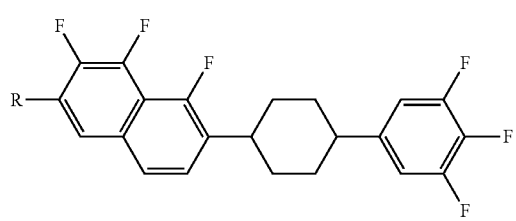

(1-10-8)
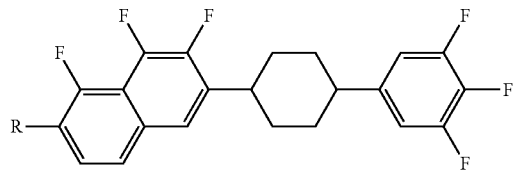

(1-10-9)
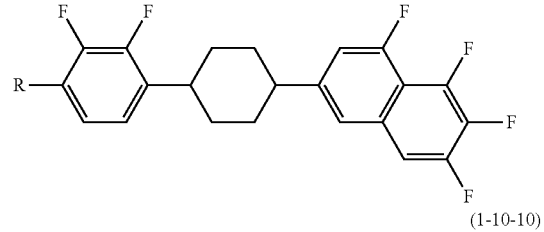

(1-10-10)
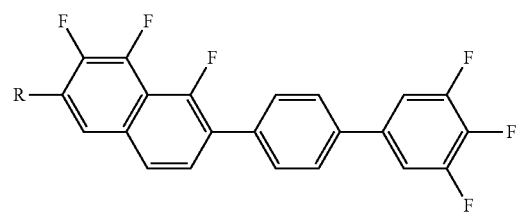

(1-10-11)
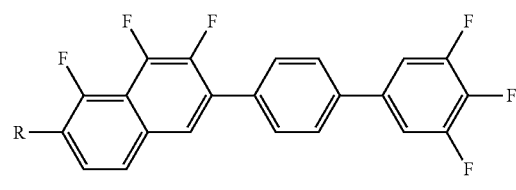

(1-10-12)
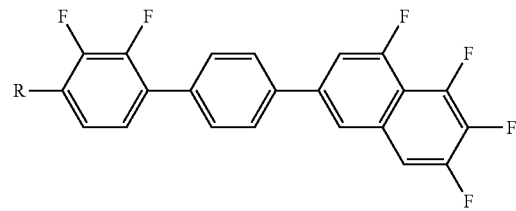

wherein, in formulas (1-10-1) to (1-10-12),

R is independently alkyl having 1 to 10 carbons, alkenyl having 2 to 10 carbons and alkoxy having 1 to 9 carbons.

Item 11. Use of at least one compound according to any one of items 1 to 10 as a component of a liquid crystal composition.

Item 12. A liquid crystal composition containing at least one of liquid crystal compounds according to any one of items 1 to 10.

Item 13. The liquid crystal composition according to item 12, further containing at least one compound selected from the group of compounds represented by formulas (2), (3) and (4):

(2)
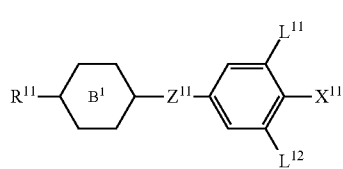

(3)
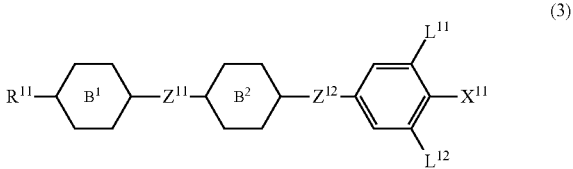

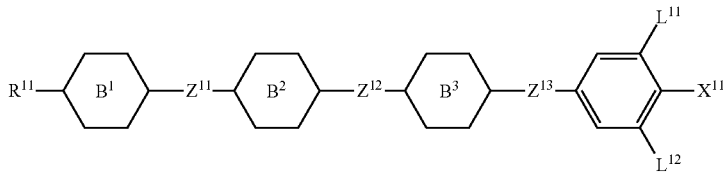
(4)

wherein, in formulas (2) to (4), $R^{11}$ is alkyl having 1 to 10 carbons or alkenyl having 2 to 10 carbons, and in the alkyl and the alkenyl, at least one of hydrogen may be replaced by fluorine and at least one of —$CH_2$— may be replaced by —O—;

$X^{11}$ is fluorine, chlorine, —$OCF_3$, —$OCHF_2$, —$CF_3$, —$CHF_2$, —$CH_2F$, —$OCF_2CHF_2$ or —$OCF_2CHFCF_3$;

ring $B^1$, ring $B^2$ and ring $B^3$ are independently 1,4-cyclohexylene, 1,4-phenylene, 2-fluoro-1,4-phenylene, 2,6-difluoro-1,4-phenylene, tetrahydropyran-2,5-diyl, 1,3-dioxane-2,5-diyl or pyrimidine-2,5-diyl;

$Z^{11}$, $Z^{12}$ and $Z^{13}$ are independently a single bond, —$CH_2CH_2$—, —CH=CH—, —C≡C—, —COO—, —$CF_2O$—, —$OCF_2$—, —$CH_2O$— or —$(CH_2)_4$—; and $L^{11}$ and $L^{12}$ are independently hydrogen or fluorine.

Item 14. The liquid crystal composition according to item 12 or 13, further containing at least one compound selected from the group of compounds represented by formula (5):

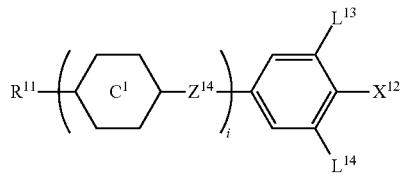
(5)

wherein, in formula (5), $R^{12}$ is alkyl having 1 to 10 carbons or alkenyl having 2 to 10 carbons, and in the alkyl and the alkenyl, at least one of hydrogen may be replaced by fluorine and at least one of —$CH_2$— may be replaced by —O—;

$X^{12}$ is —C≡N or —C≡C—C≡N;

ring $C^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{14}$ is a single bond, —$CH_2CH_2$—, —C≡C—, —COO—, —$CF_2O$—, —$OCF_2$—, or —$CH_2O$—, however, at least one of $Z^{14}$ is —$CH_2CH_2$—, —C≡C—, —COO—, —$CF_2O$—, —$OCF_2$— or —$CH_2O$—, $L^{13}$ and $L^{14}$ are independently hydrogen or fluorine; and i is 1, 2, 3 or 4.

Item 15. The liquid crystal composition according to any one of items 12 to 14, further containing at least one compound selected from the group of compounds represented by formulas (6) to (12):

(6)
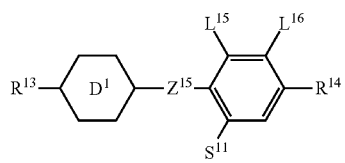

(7)
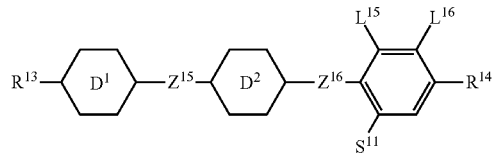

(8)
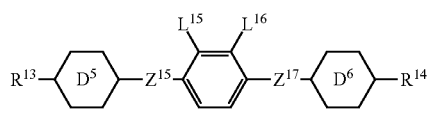

(9)
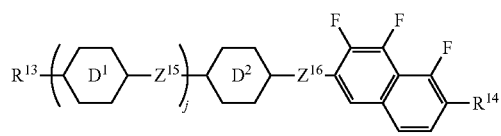

(10)
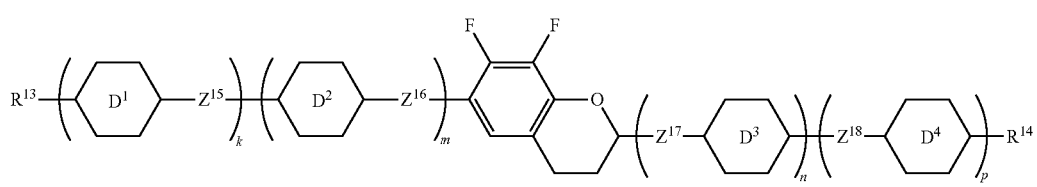

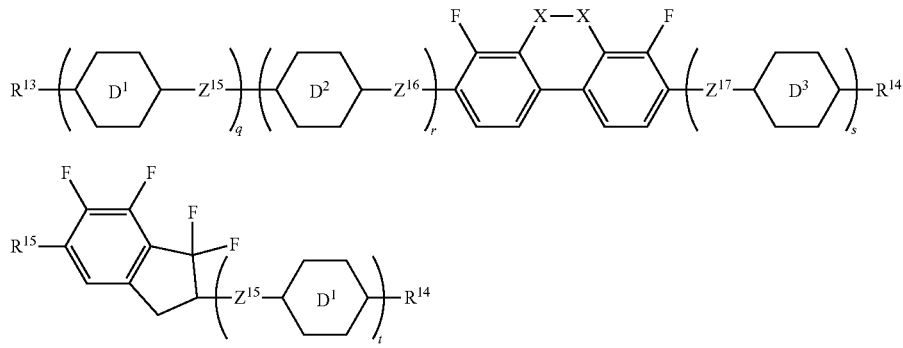

wherein, in formulas (6) to (12),

R[13] and R[14] are independently alkyl having 1 to 10 carbons or alkenyl having 2 to 10 carbons, and in the alkyl and the alkenyl, at least one of —CH$_2$— may be replaced by —O— and at least one of hydrogen may be replaced by fluorine;

R[15] is hydrogen, fluorine, alkyl having 1 to 10 carbons or alkenyl having 2 to 10 carbons, and in the alkyl and the alkenyl, at least one of —CH$_2$— may be replaced by —O— and at least one of hydrogen may be replaced by fluorine;

S[11] is hydrogen or methyl;

X is —CF$_2$—, —O— or —CHF—;

ring D[1], ring D[2], ring D[3] and ring D[4] are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;

ring D[6] and ring D[6] are independently 1,4-cyclohexylene, 1,4-cyclohexenylene, 1,4-phenylene, tetrahydropyran-2,5-diyl or decahydronaphthalene-2,6-diyl;

Z[15], Z[16], Z[17] and Z[18] are independently a single bond, —CH$_2$CH$_2$—, —COO—, —CH$_2$O—, —OCF$_2$— or —OCF$_2$CH$_2$CH$_2$—, L[15] and L[16] are independently fluorine or chlorine; and j, k, m, n, p, q, r and s are independently 0 or 1, a sum of k, m, n and p is 1 or 2, a sum of q, r and s is 0, 1, 2 or 3, and t is 1, 2 or 3.

Item 16. The liquid crystal composition according to any one of items 12 to 15, further containing at least one compound selected from the group of compounds represented by formulas (13) to (15):

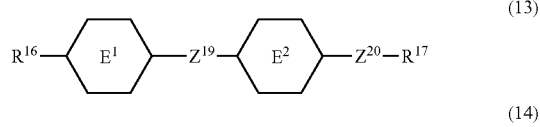

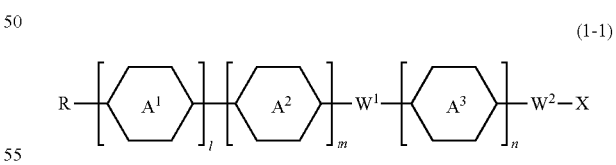

wherein, in formulas (13) to (15),

R[16] and R[17] are independently alkyl having 1 to 10 carbons or alkenyl having 2 to 10 carbons, and in the alkyl and the alkenyl, at least one of —CH$_2$— may be replaced by —O— and at least one of hydrogen may be replaced by fluorine;

ring E[1], ring E[2], ring E[3] and ring E[4] are independently 1,4-cyclohexylene, 1,4-phenylene, 2-fluoro-1,4-phenylene, 2,5-difluoro-1,4-phenylene or pyrimidine-2,5-diyl; and Z[19], Z[20] and Z[21] are independently a single bond, —CH$_2$CH$_2$—, —CH═CH—, —C≡C— or —COO—.

Item 17. The liquid crystal composition according to any one of items 12 to 16, further containing at least one optically active compound and/or polymerizable compound.

Item 18. The liquid crystal composition according to any one of items 12 to 17, further containing at least one antioxidant and/or ultraviolet light absorber.

Item 19. A liquid crystal display device including the liquid crystal composition according to any one of items 12 to 18.

The compound, the liquid crystal composition and the liquid crystal display device of the invention are described in the order.

1-1. Compound (1-1)

Compound (1-1) of the invention has 1,4-phenylene in which hydrogen in 2-position and 3-position of a ring are replaced by halogen, and therefore has a feature of having both a large dielectric anisotropy and a large dielectric constant in a minor axis direction. A preferred example of compound (1-1) of the invention is described. A preferred example of a terminal group, ring structure, a bonding group or a substituent in compound (1-1) applies also to a subordinate formula of formula (1-1) for compound (1-1).

$$R\underset{l}{\left[\bigcirc A^1\right]}\underset{m}{\left[\bigcirc A^2\right]}-W^1\underset{n}{\left[\bigcirc A^3\right]}-W^2-X \quad (1\text{-}1)$$

wherein, in formula (1-1),

R is hydrogen or alkyl having 1 to 10 carbons, and in the alkyl, at least one of —CH$_2$— may be replaced by —O— or —S—, at least one of —(CH$_2$)$_2$— may replace by —CH═CH—, and in the groups at least one of hydrogen may be replaced by halogen.

Examples of such a terminal group R include alkyl, alkoxy, alkoxyalkyl, alkoxyalkoxy, alkylthio, alkylthio-alkoxy, alkenyl, alkenyloxy, alkenyloxyalkyl, alkoxyalkenyl and alkenylthio. In the groups, at least one of hydrogen may be replaced by halogen. Preferred halogen is fluorine or chlorine. Further preferred halogen is fluorine. The groups have a straight chain or a branched chain, and contain no cyclic group such as cyclohexyl. In the groups, the straight chain is preferred to the branched chain.

A preferred configuration of —CH=CH— in the alkenyl depends on a position of a double bond. In alkenyl having a double bond in an odd-numbered position, such as —CH=CHCH$_3$, —CH=CHC$_2$H$_5$, —CH=CHC$_3$H$_7$, —CH=CHC$_4$H$_9$, —C$_2$H$_4$CH=CHCH$_3$ and —C$_2$H$_4$CH=CHC$_2$H$_5$, a trans configuration is preferred. In alkenyl having a double bond in an even-numbered position, such as —CH$_2$CH=CHCH$_3$, —CH$_2$CH=CHC$_2$H$_5$ and —CH$_2$CH=CHC$_3$H$_7$, a cis configuration is preferred. An alkenyl compound having a preferred configuration has a high clearing point or a wide temperature range of the liquid crystal phase. A detailed description is found in Mol. Cryst. Liq. Cryst., 1985, 131, 109 and Mol. Cryst. Liq. Cryst., 1985, 131, 327.

Examples of alkyl include —CH$_3$, —C$_2$H$_5$, —C$_3$H$_7$, —C$_4$H$_9$, —C$_6$H$_{13}$, —C$_7$H$_{15}$, —C$_8$H$_{17}$, —C$_9$H$_{19}$ or —C$_{10}$H$_{21}$.

Examples of alkoxy include —OCH$_3$, —OC$_2$H$_5$, —OC$_3$H$_7$, —OC$_4$H$_9$, —OC$_5$H$_{11}$, —OC$_6$H$_{13}$, —OC$_7$H$_{15}$, —OC$_8$H$_{17}$ or —OC$_9$H$_{19}$.

Examples of alkoxyalkyl include —CH$_2$OCH$_3$, —CH$_2$OC$_2$H$_5$, —CH$_2$OC$_3$H$_7$, —(CH$_2$)$_2$—OCH$_3$, —(CH$_2$)$_2$—OC$_2$H$_5$, —(CH$_2$)$_2$—OC$_3$H$_7$, —(CH$_2$)$_3$—OCH$_3$, —(CH$_2$)$_4$—OCH$_3$ or —(CH$_2$)$_5$—OCH$_3$.

Examples of alkenyl include —CH=CH$_2$, —CH=CHCH$_3$, —CH$_2$CH=CH$_2$, —CH=CHC$_2$H$_5$, —CH$_2$CH=CHCH$_3$, —(CH$_2$)$_2$—CH=CH$_2$, —CH=CHC$_3$H$_7$, —CH$_2$CH=CHC$_2$H$_5$, —(CH$_2$)$_2$—CH=CHCH$_3$ or —(CH$_2$)$_3$—CH=CH$_2$.

Examples of alkenyloxy include —OCH$_2$CH=CH$_2$, —OCH$_2$CH=CHCH$_3$ or —OCH$_2$CH=CHC$_2$H$_5$.

Examples of alkyl in which at least one of hydrogen is replaced by halogen include —CH$_2$F, —CHF$_2$, —CF$_3$, —(CH$_2$)$_2$—F, —CF$_2$CH$_2$F, —CF$_2$CHF$_2$, —CH$_2$CF$_3$, —CF$_2$CF$_3$, —(CH$_2$)$_3$—F, —(CF$_2$)$_3$—F, —CF$_2$CHFCF$_3$, —CHFCF$_2$CF$_3$, —(CH$_2$)$_4$—F, —(CF$_2$)$_4$—F, —(CH$_2$)$_5$—F, —(CF$_2$)$_5$—F, —CH$_2$Cl, —CHCl$_2$, —CCl$_3$, —(CH$_2$)$_2$—Cl, —CCl$_2$CH$_2$Cl, —CCl$_2$CHCl$_2$, —CH$_2$CCl$_3$, —CCl$_2$CCl$_3$, —(CH$_2$)$_3$—Cl, —(CCl$_2$)$_3$—Cl, —CCl$_2$CHClCCl$_3$, —CHClCCl$_2$CCl$_3$, —(CH$_2$)$_4$—Cl, —(CCl$_2$)$_4$—Cl, —(CH$_2$)$_5$—Cl or —(CCl$_2$)$_5$—Cl.

Examples of alkoxy in which at least one of hydrogen is replaced by halogen include —OCH$_2$F, —OCHF$_2$, —OCF$_3$, —O—(CH$_2$)$_2$—F, —OCF$_2$CH$_2$F, —OCF$_2$CHF$_2$, —OCH$_2$CF$_3$, —O—(CH$_2$)$_3$—F, —O—(CF$_2$)$_3$—F, —OCF$_2$CHFCF$_3$, —OCHFCF$_2$CF$_3$, —O(CH$_2$)$_4$—F, —O—(CF$_2$)$_4$—F, —O—(CH$_2$)$_5$—F, —O—(CF$_2$)$_5$—F, —OCH$_2$Cl, —OCHCl$_2$, —OCCl$_3$, —O—(CH$_2$)$_2$—Cl, —OCCl$_2$CH$_2$Cl, —OCCl$_2$CHCl$_2$, —OCH$_2$CCl$_3$, —O—(CH$_2$)$_3$—Cl, —OCCl$_2$CHClCCl$_3$, —OCHClCCl$_2$CCl$_3$, —O(CH$_2$)$_4$—Cl, —O—(CCl$_2$)$_4$—Cl, —O—(CH$_2$)$_5$—Cl or —O—(CCl$_2$)$_5$—Cl.

Examples of alkenyl in which at least one of hydrogen is replaced by halogen include —CH=CHF, —CH=CF$_2$, —CF=CHF, —CH=CHCH$_2$F, —CH=CHCF$_3$, —(CH$_2$)$_2$—CH=CF$_2$, —CH$_2$CH=CHCF$_3$, —CH=CHCF$_2$CF$_3$, —CH=CHCl, —CH=CCl$_2$, —CCl=CHCl, —CH=CHCH$_2$Cl, —CH=CHCCl$_3$, —(CH$_2$)$_2$—CH=CCl$_2$, —CH$_2$CH=CHCCl$_3$ or —CH=CHCCl$_2$CCl$_3$.

Preferred examples of R include alkyl having 1 to 10 carbons, alkenyl having 2 to 10 carbons or alkoxy having carbons 2 to 9. Further preferred examples of R include alkyl having 1 to 10 carbons or alkenyl having 2 to 10 carbons. Most preferred examples of R include —CH$_3$, —C$_2$H$_5$, —C$_3$H$_7$, —C$_4$H$_9$, —C$_5$H$_{11}$, —C$_6$H$_{13}$, —C$_7$H$_{15}$, —CH=CH$_2$, —CH=CHCH$_3$, —CH$_2$CH=CH$_2$, —CH=CHC$_2$H$_5$, —CH$_2$CH=CHCH$_3$, —(CH$_2$)$_2$—CH=CH$_2$, —CH=CHC$_3$H$_7$, —CH$_2$CH=CHC$_2$H$_5$, —(CH$_2$)$_2$—CH=CHCH$_3$ or —(CH$_2$)$_3$—CH=CH$_2$.

In formula (1-1), ring A$^1$, ring A$^2$ and ring A$^3$ are independently 1,4-cyclohexylene, 1,4-cyclohexenylene, tetrahydropyran-2,5-diyl, 1,3-dioxane-2,5-diyl, 2,6,7-trioxabicyclo[2.2.2]octane-1,4-diyl, pyrimidine-2,5-diyl, pyridine-2,5-diyl, naphthalene-2,6-diyl, decahydronaphthalene-2,6-diyl, 1,2,3,4-tetrahydronaphthalene-2,6-diyl, 1,4-phenylene, or 1,4-phenylene in which at least one of hydrogen is replaced by halogen.

Preferred examples of ring A$^1$, ring A$^2$ or ring A$^3$ include 1,4-cyclohexylene, 1,4-cyclohexenylene, 1,4-phenylene, 1,4-phenylene in which at least one of hydrogen is replaced by halogen, tetrahydropyran-2,5-diyl, 1,3-dioxane-2,5-diyl or 2,6,7-trioxabicyclo[2.2.2]octane-1,4-diyl. A configuration of cis or trans exists in 1,4-cyclohexylene. From a viewpoint of a high maximum temperature, a trans configuration is preferred. Preferred examples of 1,4-phenylene in which at least one of hydrogen is replaced by halogen include ring (A-1) to (A-17).

(A-1)

(A-2)

(A-3)

(A-4)

(A-5)

(A-6)

-continued

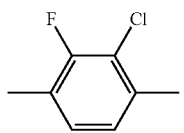 (A-7)

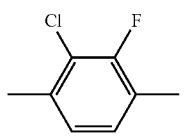 (A-8)

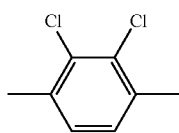 (A-9)

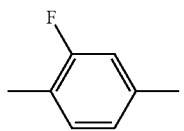 (A-10)

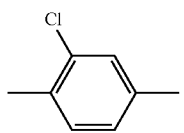 (A-11)

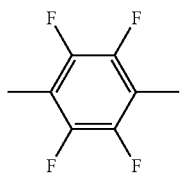 (A-12)

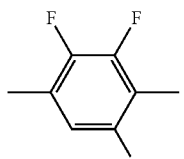 (A-13)

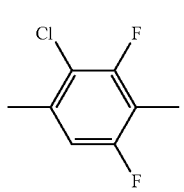 (A-14)

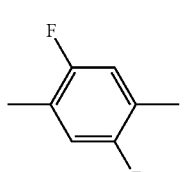 (A-15)

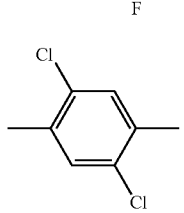 (A-16)

-continued

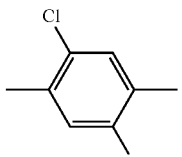 (A-17)

Then, 2-fluoro-1,4-phenylene (A-1) is asymmetrical. In the chemical formula thereof, a case where fluorine is located on a side of a left-terminal group (leftward) and a case where fluorine is located on a side of a right-terminal group (rightward) exist. Preferred 2-fluoro-1,4-phenylene is rightward (A-1) in order to increase the dielectric anisotropy. A same rule also applies to 2,6-difluoro-1,4-phenylene or the like. Rings (A-1) to (A-9) are further preferred.

Further preferred examples of 1,4-phenylene in which at least one of hydrogen is replaced by halogen include 2-fluoro-1,4-phenylene (A-1), 2,6-difluoro-1,4-phenylene (A-2), 2-chloro-6-fluoro-1,4-phenylene (A-3), 2,3-difluoro-1,4-phenylene (A-6) or 2-chloro-3-fluoro-1,4-phenylene (A-7 and A-8). Most preferred examples of 1,4-phenylene in which at least one of hydrogen is replaced by halogen include 2-fluoro-1,4-phenylene (A-1), 2,6-difluoro-1,4-phenylene (A-2) or 2,3-difluoro-1,4-phenylene (A-6).

Then, 1,3-dioxane-2,5-diyl is asymmetrical. A case where —O— is located on a side of a left-terminal group (leftward; A-18), and a case where —O— is located on a side of a right-terminal group (rightward; A-19) exist. Preferred 1,3-dioxane-2,5-diyl is rightward (A-19) in order to increase the dielectric anisotropy. In 2,6,7-trioxabicyclo[2.2.2]octane-1,4-diyl (A-20 and A-21), pyrimidine-2,5-diyl (A-22 and A-23) and pyridine-2,5-diyl (A-24 and A-25), —O— is preferably rightward (A-21, A-23 and A-25). In tetrahydropyran-2,5-diyl (A-26 and A-27), from a viewpoint of the large dielectric anisotropy, —O— is preferably rightward (A-27), and from a viewpoint of the large dielectric constant in the minor axis direction, —O— is preferably leftward (A-26).

 (A-18)

(A-19)

(A-20)

(A-21)

(A-22)

-continued

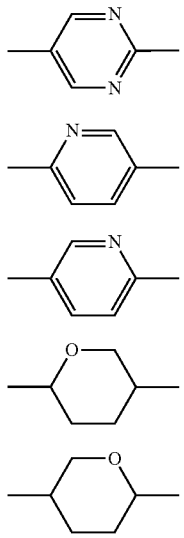

(A-23)

(A-24)

(A-25)

(A-26)

(A-27)

Further preferred examples of ring $A^1$, ring $A^2$ or ring $A^3$ include 1,4-cyclohexylene, 1,4-phenylene, 2-fluoro-1,4-phenylene, 2,6-difluoro-1,4-phenylene, tetrahydropyran-2,5-diyl or 1,3-dioxane-2,5-diyl.

In formula (1-1), $W^1$ is a group represented by formula (1a) or formula (1b).

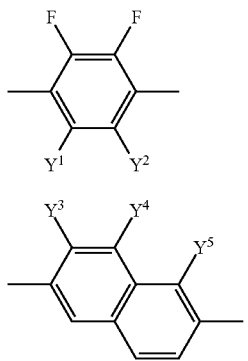

(1a)

(1b)

In formula (1a) and formula (1b), $Y^1$ and $Y^2$ are independently hydrogen, chlorine or fluorine, $Y^3$, $Y^4$ and $Y^5$ are independently hydrogen, fluorine or chlorine, and at least two of $Y^3$, $Y^4$ and $Y^5$ is fluorine or chlorine.

A preferred combination of $Y^1$ and $Y^2$ includes a combination in which both $Y^1$ and $Y^2$ are fluorine, or a combination in which one is hydrogen and the other is fluorine. A preferred combination of $Y^3$, $Y^4$ and $Y^5$ includes a combination in which two of $Y^3$, $Y^4$ and $Y^5$ is fluorine, and a remainder is hydrogen, or a combination in which all thereof are fluorine. A further preferred combination of $Y^3$, $Y^4$ and $Y^5$ includes a combination in which all of $Y^3$, $Y^4$ and $Y^5$ are fluorine.

In formula (1-1), $W^2$ is a group represented by formula (1c) or formula (1d).

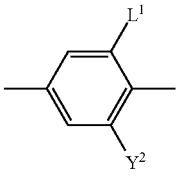

(1c)

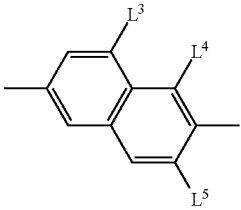

(1d)

In formula (1c) and formula (1d), $L^1$, $L^2$, $L^3$, $L^4$ and $L^5$ are independently hydrogen, fluorine or chlorine.

A preferred combination of $L^1$ and $L^2$ includes a combination in which one is hydrogen and the other is fluorine, or a combination in which both $L^1$ and $L^2$ are fluorine. A preferred combination of $L^3$, $L^4$ and $L^5$ includes a combination in which all of $L^3$, $L^4$ and $L^5$ are fluorine, or a combination in which $L^3$ is hydrogen and a remainder is fluorine. A further preferred combination of $L^3$, $L^4$ and $L^5$ includes a combination in which all of $L^3$, $L^4$ and $L^5$ are fluorine.

In formula (1-1), terminal group X is halogen, —C≡N, —N=C=S, —SF$_5$, —CF$_3$, —CF$_2$H, —CFH$_2$, —OCF$_3$, —OCF$_2$H, —OCFH$_2$ or alkyl having 1 to 10 carbons, in the alkyl, at least one of —CH$_2$— may be replaced by —O— or —S—, at least one of —(CH$_2$)$_2$— may replace by —CH=CH—, and in the groups, at least one of hydrogen may be replaced by halogen.

Examples of alkyl in which at least one of hydrogen is replaced by fluorine include —CH$_2$F, —CHF$_2$, —CF$_3$, —(CH$_2$)$_2$—F, —CF$_2$CH$_2$F, —CF$_2$CHF$_2$, —CH$_2$CF$_3$, —CF$_2$CF$_3$, —(CH$_2$)$_3$—F, —(CF$_2$)$_2$—CF$_3$, —CF$_2$CHFCF$_3$, —CHFCF$_2$CF$_3$, —(CH$_2$)$_4$—F, —(CF$_2$)$_3$—CF$_3$, —(CH$_2$)$_5$—F or —(CF$_2$)$_4$—CF$_3$.

Examples of alkoxy in which at least one of hydrogen is replaced by fluorine include —OCH$_2$F, —OCHF$_2$, —OCF$_3$, —O—(CH$_2$)$_2$—F, —OCF$_2$CH$_2$F, —OCF$_2$CHF$_2$, —OCH$_2$CF$_3$, —O—(CH$_2$)$_3$—F, —O—(CF$_2$)$_2$—CF$_3$, —OCF$_2$CHFCF$_3$, —OCHFCF$_2$CF$_3$, —O—(CH$_2$)$_4$—F, —O—(CF$_2$)$_3$—CF$_3$, —O—(CH$_2$)$_5$—F or —O—(CF$_2$)$_4$—CF$_3$.

Examples of alkenyl in which at least one of hydrogen is replaced by fluorine include —CH=CHF, —CH=CF$_2$, —CF=CHF, —CF=CF$_2$, —CH=CHCH$_2$F, —CH=CHCF$_3$, —CF=CHCF$_3$, —CF=CFCF$_3$, —(CH$_2$)$_2$—CH=CF$_2$, —(CH$_2$)$_2$—CF=CF$_2$, —(CH$_2$)$_2$—CH=CHCF$_3$, —(CH$_2$)$_2$—CF=CHCF$_3$ or —(CH$_2$)$_2$—CF=CFCF$_3$.

Preferred examples of X include fluorine, chlorine, —C≡N, —N=C=S, —SF$_5$, —CH$_2$F, —CHF$_2$, —CF$_3$, —(CH$_2$)$_2$—F, —CH$_2$CF$_3$, —CF$_2$CF$_3$, —(CH$_2$)$_3$—F, —(CH$_2$)$_2$—CF$_3$, —(CF$_2$)$_3$—F, —(CH$_2$)$_4$—F, —(CH$_2$)$_3$—CF$_3$, —(CF$_2$)$_4$—F, —(CF$_2$)$_5$—F, —(CF$_2$)$_6$—F, —(CF$_2$)$_7$—F, —OCH$_2$F, —OCHF$_2$, —OCF$_3$, —O—(CH$_2$)$_2$—F, —OCH$_2$CF$_3$, —OCF$_2$CF$_3$, —O—(CH$_2$)$_3$—F, —O—(CH$_2$)$_2$—CF$_3$, —O—(CF$_2$)$_3$—F, —O(CH$_2$)$_4$—F, —O—(CH$_2$)$_3$—CF$_3$, —O—(CF$_2$)$_4$—F, —O—(CF$_2$)$_5$—F, —O—

$(CF_2)_6$—F, —CH=CHF, —CH=CF$_2$, —CF=CHF, —CF=CF$_2$, —CH=CHCH$_2$F, —CH=CHCF$_3$, —CF=CHCF$_3$, —CF=CFCF$_3$, —(CH$_2$)$_2$—CH=CF$_2$, —(CH$_2$)$_2$—CF=CF$_2$, —(CH$_2$)$_2$—CH=CHCF$_3$, —(CH$_2$)$_2$—CF=CHCF$_3$ or —(CH$_2$)$_2$—CF=CFCF$_3$.

Further preferred examples of X include fluorine, chlorine, —C≡N, —CHF$_2$, —CF$_3$, —OCHF$_2$, —OCF$_3$, —CH=CHCF$_3$, —CF=CHCF$_3$ or —CF=CFCF$_3$. Most preferred examples of X include fluorine, —CF$_3$ or —OCF$_3$.

In formula (1), l, m and n are independently 0 or 1, and a sum of l, m and n is 0, 1 or 2. Preferred combinations of l, m and n include combinations (l=m=n=0), (l=1, m=n=0), (n=1, l=m=0), (l=m=1, n=0) and (l=n=1, m=0). Further preferred combinations of l, m and n include combinations (l=1, m=n=0) and (n=1, l=m=0).

1-2. Physical Properties of Compound (1-1)

In compound (1-1), physical properties such as a clearing point, optical anisotropy and dielectric anisotropy can be arbitrarily adjusted by suitably selecting a kind of $R^1$, ring $A^1$ to ring $A^3$, $W^1$, $W^2$ or X, or a combination of l, m and n. Compound (1-1) may also contain an isotope such as $^2$H (deuterium) and $^{13}$C in an amount larger than an amount of natural abundance, because no significant difference is in the physical properties of the compound. A main effect of kinds of R or the like on the physical properties of compound (1-1) are described below.

When left-terminal group R has a straight chain, the temperature range of the liquid crystal phase is wide, and the viscosity is small. When R is a branched chain, compatibility with other liquid crystal compounds is good. A compound in which R is optically active is useful as a chiral dopant. A reverse twisted domain to be generated in the liquid crystal device can be prevented by adding the compound to the composition. A compound in which R is not optically active is useful as a component of the composition. When R is alkenyl, a preferred configuration depends on a position of a double bond. An alkenyl compound having a preferred configuration has a small viscosity, a high maximum temperature or a wide temperature range of the liquid crystal phase. When R is alkoxy, compound (1-1) has the high maximum temperature.

When all of ring $A^1$ to ring $A^3$ are 1,4-cyclohexylene, the clearing point is high and the viscosity is small. When at least one of ring $A^1$ to ring $A^3$ is 1,4-phenylene, or 1,4-phenylene in which at least one of hydrogen is replaced by halogen, the optical anisotropy is comparatively large and an orientational order parameter is comparatively large. When all of ring $A^1$ to ring $A^3$ are 1,4-phenylene, 1,4-phenylene in which at least one of hydrogen is replaced by halogen, pyrimidine-2,5-diyl, pyridine-2,5-diyl or a combination thereof, the large optical anisotropy is particularly large. When at least one of ring $A^1$ to ring $A^3$ is 2-fluoro-1,4-phenylene, 2-chloro-1,4-phenylene, 2,6-difluoro-1,4-phenylene, 2,6-dichloro-1,4-phenylene, 2-chloro-6-fluoro-1,4-phenylene, tetrahydropyran-2,5-diyl, 1,3-dioxane-2,5-diyl, 2,6,7-trioxabicyclo[2.2.2]octane-1,4-diyl, pyrimidine-2,5-diyl or pyridine-2,5-diyl, the large dielectric anisotropy is satisfied. When at least one of rings $A^1$ to $A^3$ is 2,3-difluoro-1,4-phenylene, 2,3-dichloro-1,4-phenylene, 2-chloro-3-fluoro-1,4-phenylene, tetrahydropyran-2,5-diyl or 1,3-dioxane-2,5-diyl, the dielectric constant in the minor axis direction is large.

When both $Y^1$ and $Y^2$ are fluorine, the dielectric anisotropy is large and the dielectric constant in the minor axis direction is large. When either $Y^1$ or $Y^2$ is fluorine, the dielectric anisotropy is comparatively large, the dielectric constant in the minor axis direction is large and the compatibility with other liquid crystal compounds is good.

When all of $Y^3$, $Y^4$ and $Y^5$ are fluorine, the dielectric anisotropy is large and the dielectric constant in the minor axis direction is large. When two of $Y^3$, $Y^4$ and $Y^5$ is fluorine, the dielectric anisotropy is comparatively large, the dielectric constant in the minor axis direction is large and the compatibility with other liquid crystal compounds is good.

When both $L^1$ and $L^2$ are fluorine or when $L^1$ is fluorine and $L^2$ is hydrogen, the clearing point is high. When both $L^1$ and $L^2$ are fluorine, the viscosity is small and chemical stability is high.

When both $L^1$ and $L^2$ are hydrogen, the clearing point is high. When either $L^1$ or $L^2$ is fluorine, the dielectric anisotropy is comparatively large, the dielectric constant in the minor axis direction is large, and the compatibility with other liquid crystal compounds is good. When both $L^1$ and $L^2$ are fluorine, the dielectric constant in the minor axis direction is large and the dielectric anisotropy is particularly large.

When all of $L^3$, $L^4$ and $L^5$ are fluorine, the dielectric constant in the minor axis direction is large, the viscosity is small and the chemical stability is high. Alternatively, when two of $L^3$, $L^4$ and $L^5$ are fluorine and a remainder is hydrogen, the clearing point is high.

When X is fluorine, chlorine, —C≡N, —N=C=S, —CF$_3$, —CF=CHF, —CH=CHCF$_3$, —CF=CHCF$_3$ or —CF=CFCF$_3$, the dielectric anisotropy is particularly large. When X is —C≡N, —N=C=S, —CH=CHF, —CH=CF$_2$, —CF=CHF, —CF=CF$_2$, —CH=CHCH$_2$F, —CH=CHCF$_3$, —CF=CHCF$_3$ or —CF=CFCF$_3$, the clearing point is high and the optical anisotropy is large. When X is fluorine, chlorine, —OCH$_2$F, —OCHF$_2$ or —OCF$_3$, the compatibility with other liquid crystal compounds is good. When X is fluorine, —CF$_3$, —CF$_2$CF$_3$, —(CF$_2$)$_3$—F, —(CF$_2$)$_4$—F, —(CF$_2$)$_5$—F, —(CF$_2$)$_6$—F, —(CF$_2$)$_7$—F, —OCF$_3$, —OCF$_2$CF$_3$, —O—(CF$_2$)$_3$—F, —O—(CF$_2$)$_4$—F, —O—(CF$_2$)$_5$—F or —O—(CF$_2$)$_6$—F, the chemical stability is high.

When a combination of l, m and n includes a combination (l=m=n=0), the compatibility with other liquid crystal compounds is good and the viscosity is small. When the combination includes a combination (l=1, m=n=0) or (n=1, l=m=0), the compatibility with other liquid crystal compounds is good, the dielectric anisotropy is large and the dielectric constant in the minor axis direction is particularly large. When the combination includes a combination (l=m=1, n=0) or (l=n=1, m=0), the clearing point is high, the dielectric anisotropy is large and the dielectric constant in the minor axis direction is large. When the combination includes a combination (l=1, m=n=0) or (n=1, l=m=0), the clearing point is particularly high and the dielectric anisotropy is large.

As described above, a compound having objective physical properties can be obtained by suitably selecting a kind of ring structure, a terminal group a bonding group or the like. Accordingly, compound (1-1) is useful as the component of the composition used for a liquid crystal display device having a mode such as a PC, TN, STN, ECB, OCB, IPS, FFS or VA mode.

1-3. Preferred Compound

Preferred examples of compound (1-1) include a compound represented by formula (1-2).

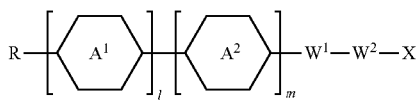

In formula (1-2),

R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^1$ and ring $A^2$ are independently 1,4-cyclohexylene, 1,4-cyclohexenylene, 1,3-dioxane-2,5-diyl, 2,6,7-trioxabicyclo[2.2.2]octane-1,4-diyl, pyrimidine-2,5-diyl, naphthalene-2,6-diyl, 2-fluoro-1,4-phenylene, 3-fluoro-1,4-phenylene, 2,3-difluoro-1,4-phenylene or 3,5-difluoro-1,4-phenylene;

$W^1$ is a group represented by formula (1a) or formula (1b).

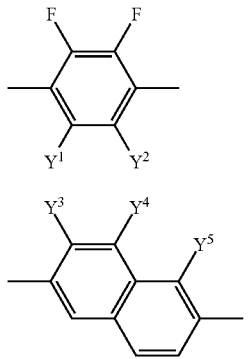

In formulas (1a) and (1b), $Y^1$ and $Y^2$ are independently hydrogen, chlorine or fluorine, $Y^3$, $Y^4$ and $Y^5$ are independently hydrogen, fluorine or chlorine, and at least two of $Y^3$, $Y^4$ and $Y^5$ is fluorine or chlorine.

In formula (1-2), $W^2$ is a group represented by formula (1c) or formula (1d).

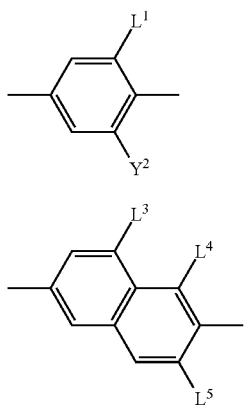

In formulas (1c) and (1d), $L^1$, $L^2$, $L^3$, $L^4$ and $L^5$ are independently hydrogen, fluorine or chlorine; and in formula (1-2), X is fluorine, chlorine, —C≡N, —N=C=S, —SF$_5$, —CH$_2$F, —CHF$_2$, —CF$_3$, —(CH$_2$)$_2$—F, —CH$_2$CF$_3$, —CF$_2$CF$_3$, —(CH$_2$)$_3$—F, —(CH$_2$)$_2$—CF$_3$, —(CF$_2$)$_3$—F, —(CH$_2$)$_4$—F, —(CH$_2$)$_3$—CF$_3$, —(CF$_2$)$_4$—F, —(CF$_2$)$_5$—F, —(CF$_2$)$_6$—F, —(CF$_2$)$_7$—F, —OCH$_2$F, —OCHF$_2$, —OCF$_3$, —O—(CH$_2$)$_2$—F, —OCH$_2$CF$_3$, —OCF$_2$CF$_3$, —O—(CH$_2$)$_3$—F, —O—(CH$_2$)$_2$—CF$_3$, —O—(CF$_2$)$_3$—F, —O(CH$_2$)$_4$—F, —O—(CH$_2$)$_3$—CF$_3$, —O—(CF$_2$)$_4$—F, —O—(CF$_2$)$_5$—F, —O—(CF$_2$)$_6$—F, —CH=CHF, —CH=CF$_2$, —CF=CHF, —CF=CF$_2$, —CH=CHCH$_2$F, —CH=CHCF$_3$, —CF=CHCF$_3$, —CF=CFCF$_3$, —(CH$_2$)$_2$—CH=CF$_2$, —(CH$_2$)$_2$—CF=CF$_2$, —(CH$_2$)$_2$—CH=CHCF$_3$, —(CH$_2$)$_2$—CF=CHCF$_3$ or —(CH$_2$)$_2$—CF=CFCF$_3$; and l and m are 0 or 1, and a sum of l and m is 0. 1 or 2;

in which, when a sum of l and m is 1, either $W^1$ or $W^2$ is a group represented by formula (1b) or (1d), or ring $A^1$ or $A^2$ is 1,4-cyclohexylene, 1,4-cyclohexenylene, 1,3-dioxane-2,5-diyl, 2,6,7-trioxabicyclo[2.2.2]octane-1,4-diyl, pyrimidine-2,5-diyl, naphthalene-2,6-diyl, 2-fluoro-1,4-phenylene, 2,3-difluoro-1,4-phenylene or 3,5-difluoro-1,4-phenylene.

Further preferred examples of compound (1-1) include a compound represented by formula (1-3) or formula (1-4).

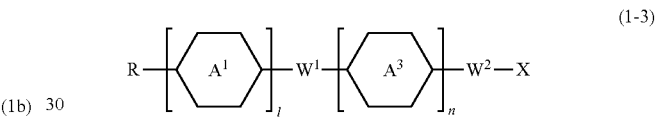

In formula (1-3),

R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^1$ is 1,4-cyclohexylene, 1,4-cyclohexenylene, 1,3-dioxane-2,5-diyl, 2,6,7-trioxabicyclo[2.2.2]octane-1,4-diyl, pyrimidine-2,5-diyl, naphthalene-2,6-diyl, 2-fluoro-1,4-phenylene, 3-fluoro-1,4-phenylene, 2,3-difluoro-1,4-phenylene or 3,5-difluoro-1,4-phenylene;

ring $A^3$ is 1,4-cyclohexylene, 1,4-cyclohexenylene, 1,3-dioxane-2,5-diyl, 2,6,7-trioxabicyclo[2.2.2]octane-1,4-diyl, pyrimidine-2,5-diyl, naphthalene-2,6-diyl, 1,4-phenylene, 2-fluoro-1,4-phenylene, 3-fluoro-1,4-phenylene, 2,3-difluoro-1,4-phenylene or 3,5-difluoro-1,4-phenylene;

$W^1$ is a group represented by formula (1a) or (1b).

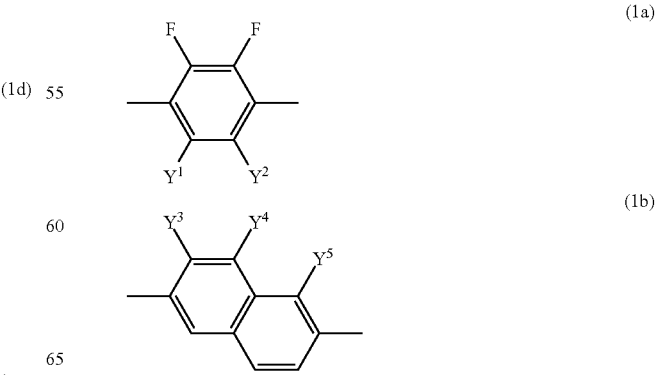

In formulas (1a) and (1b), $Y^1$ and $Y^2$ are independently hydrogen, chlorine or fluorine, $Y^3$, $Y^4$ and $Y^5$ are independently hydrogen, fluorine or chlorine, and at least two of $Y^3$, $Y^4$ and $Y^5$ is fluorine or chlorine.

In formula (1-3), $W^2$ is a group represented by formula (1c) or (1d).

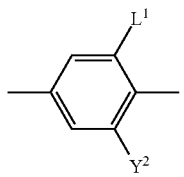
(1c)

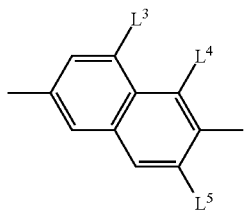
(1d)

In formulas (1c) and (1d), $L^2$, $L^3$, $L^4$ and $L^5$ are independently hydrogen, fluorine or chlorine; and in formula (1-3), X is fluorine, chlorine, —C≡N, —N═C═S, —SF$_5$, —CH$_2$F, —CHF$_2$, —CF$_3$, —(CH$_2$)$_2$—F, —CH$_2$CF$_3$, —CF$_2$CF$_3$, —(CH$_2$)$_3$—F, —(CH$_2$)$_2$—CF$_3$, —(CF$_2$)$_3$—F, —(CH$_2$)$_4$—F, —(CH$_2$)$_3$—CF$_3$, —(CF$_2$)$_4$—F, —(CF$_2$)$_5$—F, —(CF$_2$)$_6$—F, —(CF$_2$)$_7$—F, —OCH$_2$F, —OCHF$_2$, —OCF$_3$, —O—(CH$_2$)$_2$—F, —OCH$_2$CF$_3$, —OCF$_2$CF$_3$, —O—(CH$_2$)$_3$—F, —O—(CH$_2$)$_2$—CF$_3$, —O—(CF$_2$)$_3$—F, —O(CH$_2$)$_4$—F, —O—(CH$_2$)$_3$—CF$_3$, —O—(CF$_2$)$_4$—F, —O—(CF$_2$)$_5$—F, —O—(CF$_2$)$_6$—F, —CH═CHF, —CH═CF$_2$, —CF═CHF, —CF═CF$_2$, —CH═CHCH$_2$F, CH═CHCF$_3$, —CF═CHCF$_3$, —CF═CFCF$_3$, —(CH$_2$)$_2$—CH═CF$_2$, —(CH$_2$)$_2$—CF═CF$_2$, —(CH$_2$)$_2$—CH═CHCF$_3$, —(CH$_2$)$_2$—CF═CHCF$_3$ or —(CH$_2$)$_2$—CF═CFCF$_3$; and l and n are 0 or 1, and a sum of l and n is 0, 1 or 2.

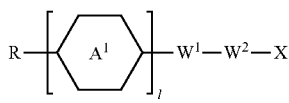
(1-4)

In formula (1-4),

R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^1$ is independently 1,4-cyclohexylene, 1,4-cyclohexenylene, 1,3-dioxane-2,5-diyl, pyrimidine-2,5-diyl, naphthalene-2,6-diyl, 2-fluoro-1,4-phenylene, 3-fluoro-1,4-phenylene or 2,3-difluoro-1,4-phenylene; and $W^1$ is a group represented by formula (1a) or (1b).

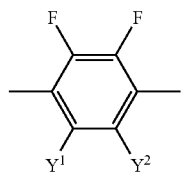
(1a)

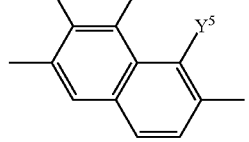
(1b)

In formulas (1a) and (1b), $Y^1$ and $Y^2$ are independently hydrogen, chlorine or fluorine, $Y^3$, $Y^4$ and $Y^5$ are independently hydrogen, fluorine or chlorine, and at least two of $Y^3$, $Y^4$ and $Y^5$ is fluorine or chlorine.

In formula (1-4), $W^2$ is a group represented by formula (1c) or (1d).

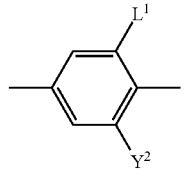
(1c)

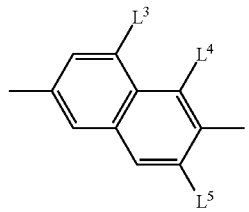
(1d)

In formulas (1c) and (1d), $L^1$, $L^2$, $L^3$, $L^4$ and $L^5$ are independently hydrogen, fluorine or chlorine.

In formula (1-4),

X is fluorine, —C≡N, —N═C═S, —SF$_5$, —CF$_3$, —CHF$_2$, —CH$_2$F, —OCF$_3$, —OCHF$_2$ or —OCH$_2$F; and l is 0 or 1.

Particularly preferred examples of compound (1-1) include a compound represented by formula (1-5), formulas (1-6-1) to (1-6-5), formula (1-7) or formulas (1-8-1) to (1-8-5).

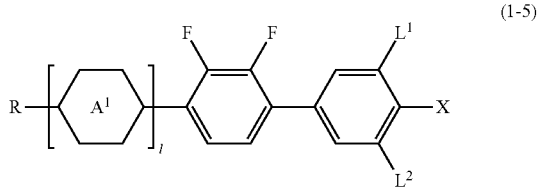
(1-5)

In formula (1-5),

R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^1$ is 1,4-cyclohexylene, 1,4-cyclohexenylene, 1,3-dioxane-2,5-diyl, pyrimidine-2,5-diyl, naphthalene-2,6-diyl, 1,4-phenylene, 2-fluoro-1,4-phenylene, 3-fluoro-1,4-phenylene or 2,3-difluoro-1,4-phenylene;

$L^1$ and $L^2$ are independently hydrogen or fluorine;

X is fluorine, —C≡N, —N=C=S, —SF$_5$, —CF$_3$, —CHF$_2$, —CH$_2$F, —OCF$_3$, —OCHF$_2$ or —OCH$_2$F; and l is 0 or 1.

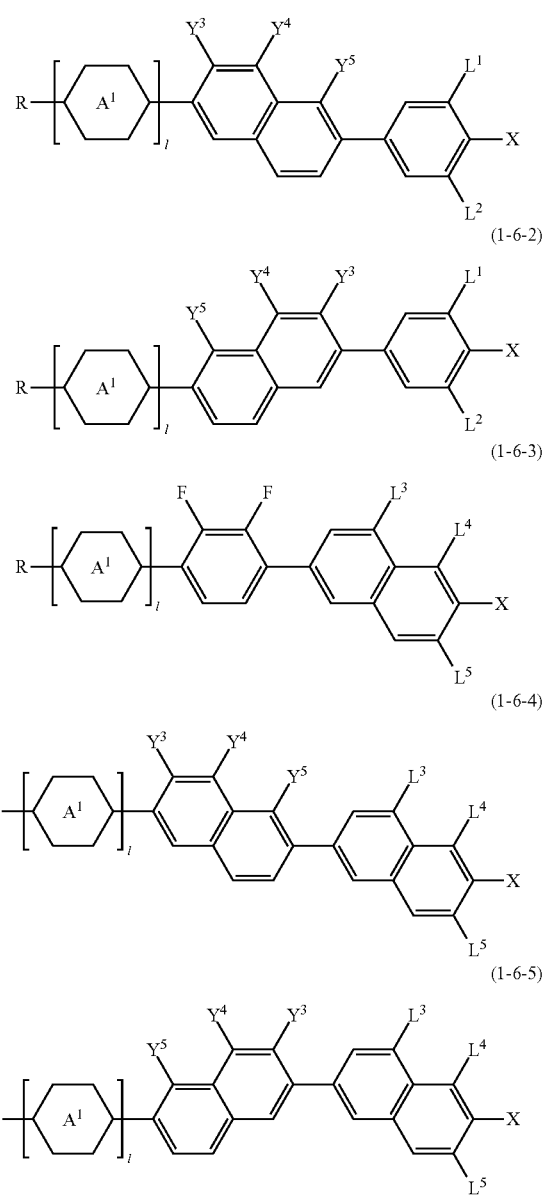

In formulas (1-6-1) to (1-6-5),

R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^1$ is 1,4-cyclohexylene, 1,4-cyclohexenylene, 1,3-dioxane-2,5-diyl, or pyrimidine-2,5-diyl;

$Y^3$, $Y^4$ and $Y^5$ are independently hydrogen, fluorine or chlorine, and at least two of $Y^3$, $Y^4$ and $Y^5$ is fluorine or chlorine;

$L^1$, $L^2$, $L^3$, $L^4$ and $L^5$ are independently hydrogen, fluorine or chlorine;

X is fluorine, —C≡N, —CF$_3$ or —OCF$_3$; and l is 0 or 1.

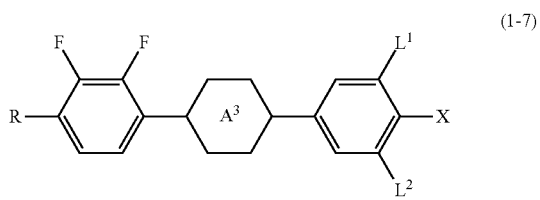

In formula (1-7),

R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^3$ is 1,4-cyclohexylene, 4-cyclohexenylene, 1,3-dioxane-2,5-diyl, pyrimidine-2,5-diyl, naphthalene-2,6-diyl, 1,4-phenylene, 2-fluoro-1,4-phenylene or 2,3-difluoro-1,4-phenylene;

$L^1$ and $L^2$ are independently hydrogen or fluorine; and

X is fluorine, —C≡N, —N=C=S, —SF$_5$, —CF$_3$, —CHF$_2$, —CH$_2$F, —OCF$_3$, —OCHF$_2$ or —OCH$_2$F.

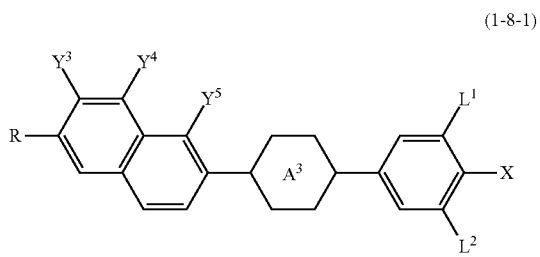

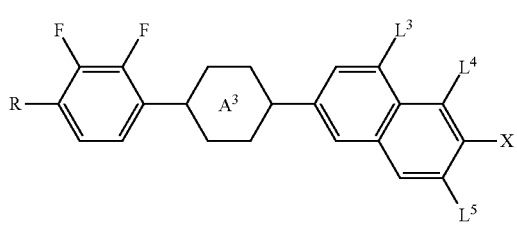

(1-8-4)

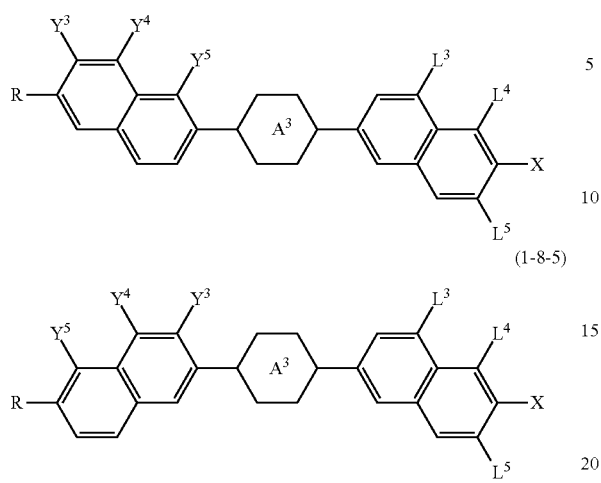

(1-8-5)

In formulas (1-8-1) to (1-8-5),

R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;

ring $A^3$ is 1,4-cyclohexylene, 1,4-cyclohexenylene, 1,3-dioxane-2,5-diyl, pyrimidine-2,5-diyl, 1,4-phenylene, 2-fluoro-1,4-phenylene or 2,3-difluoro-1,4-phenylene;

$Y^3$, $Y^4$ and $Y^5$ are independently hydrogen, fluorine or chlorine, and at least two of $Y^3$, $Y^4$ and $Y^5$ is fluorine or chlorine;

$L^1$, $L^2$, $L^3$, $L^4$ and $L^5$ are independently hydrogen, fluorine or chlorine; and X is fluorine, —C≡N, —CF$_3$ or —OCF$_3$.

Most preferred examples of compound (1-1) include a compound represented by formulas (1-9-1) to (1-9-12) or formulas (1-10-1) to (1-10-12).

(1-9-1)

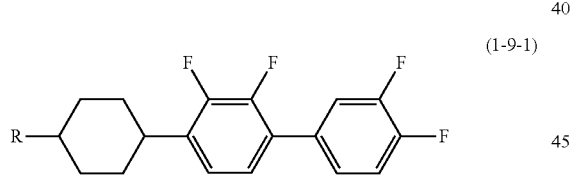

(1-9-2)

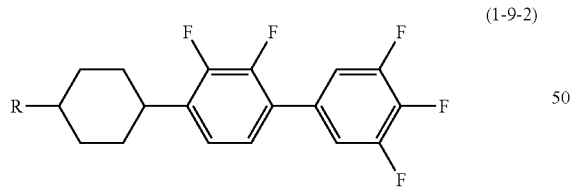

(1-9-3)

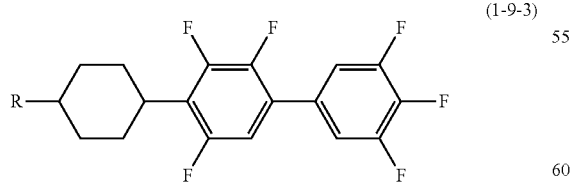

(1-9-4)

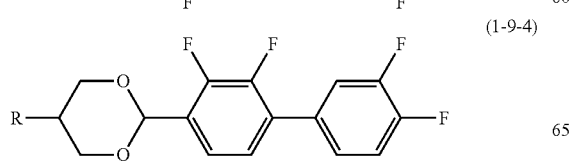

(1-9-5)

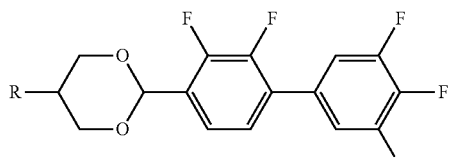

(1-9-6)

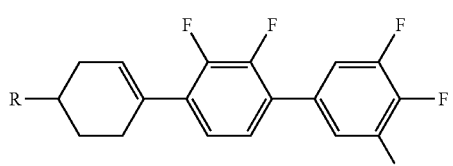

(1-9-7)

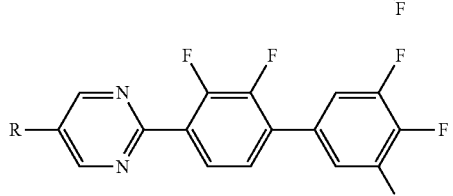

(1-9-8)

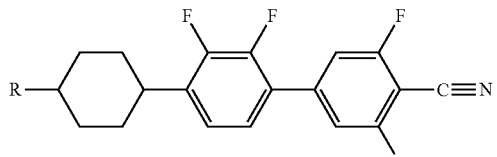

(1-9-9)

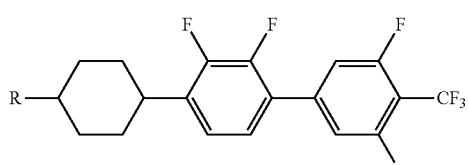

(1-9-10)

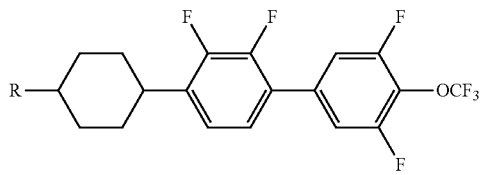

(1-9-11)

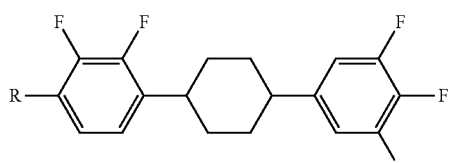

(1-9-12)

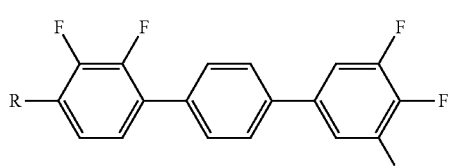

In formulas (1-9-1) to (1-9-12), R is independently alkyl having 1 to 10 carbons, alkenyl having 2 to 10 carbons or alkoxy having 1 to 9 carbons.

(1-10-1)
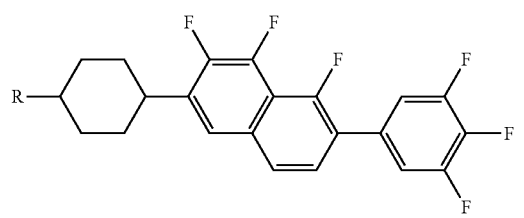

(1-10-2)
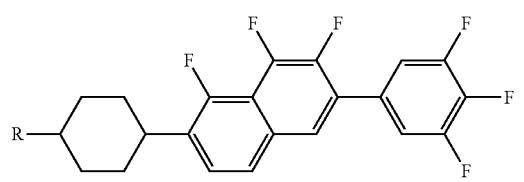

(1-10-3)
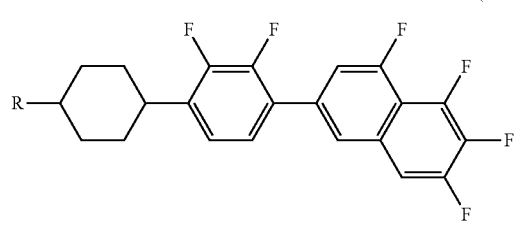

(1-10-4)
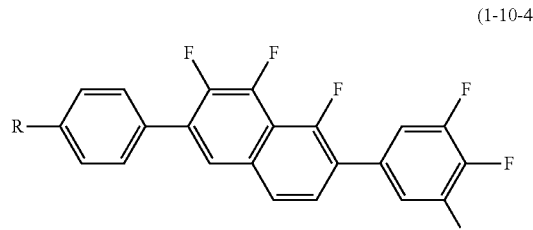

(1-10-5)
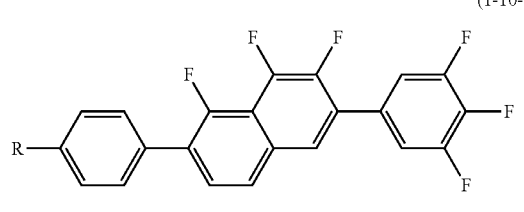

(1-10-6)
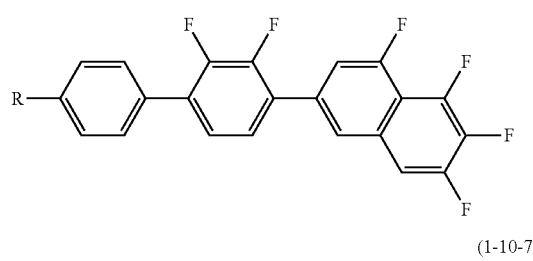

(1-10-7)
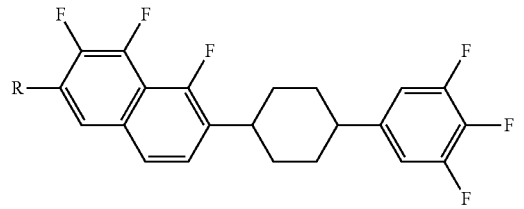

(1-10-8)
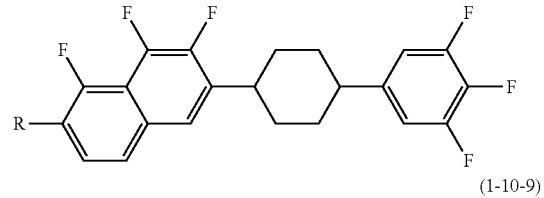

(1-10-9)
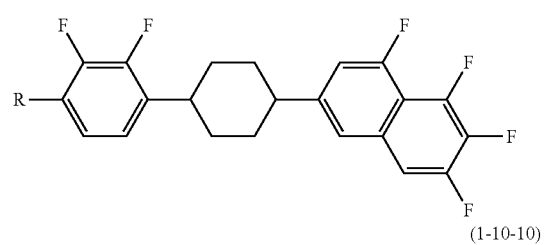

(1-10-10)
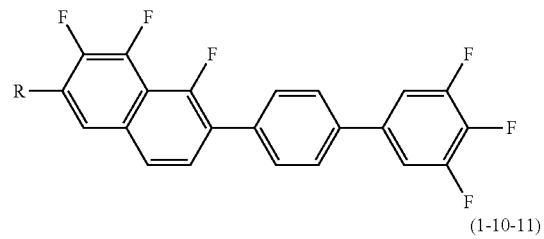

(1-10-11)
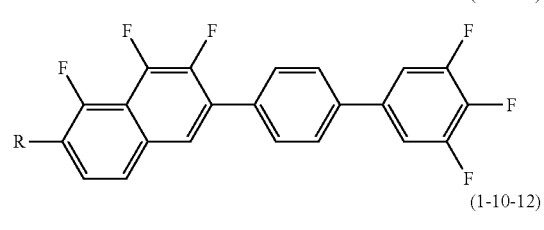

(1-10-12)
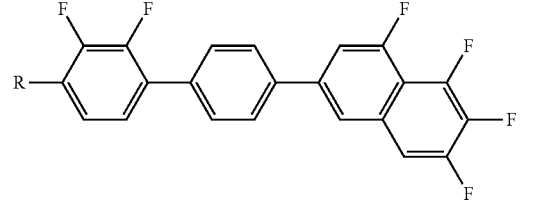

In formulas (1-10-1) to (1-10-12), R is independently alkyl having 1 to 10 carbons, alkenyl having 2 to 10 carbons or alkoxy having 1 to 9 carbons.

1-4. Synthesis of Compound (1-1)

A synthetic method of compound (1-1) is described. Compound (1-1) can be synthesized by suitably combining methods in synthetic organic chemistry. A method of introducing an objective terminal group, a ring or a bonding group into a starting material is described in books such as "Organic Syntheses" (John Wiley & Sons, Inc.), "Organic Reactions" (John Wiley & Sons, Inc.), "Comprehensive Organic Synthesis" (Pergamon Press) and "New Experimental Chemistry Course (Shin Jikken Kagaku Koza in Japanese)" (Maruzen Co., Ltd.).

1-4-1. Formation of a Single Bond

An example of method of forming a single bond in compound (1-1) is as described in a scheme below. In the scheme, MSG$^1$ (or MSG$^2$) is a monovalent organic group having at least one ring. The monovalent organic groups represented by a plurality of MSG$^1$ (or MSG$^2$) may be identical or different. Compound (1A) corresponds to compound (1-1) or an intermediate of compound (1-1).

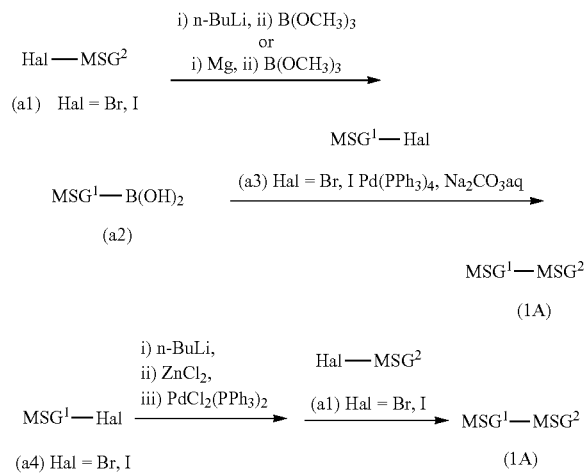

Compound (1A) is prepared by allowing arylboronic acid (a2) obtained from compound (a1) to react with compound (a3) in the presence of carbonate and a tetrakis(triphenylphosphine)palladium catalyst. The compound (1A) can be also prepared by allowing compound (a4) to react with n-butyllithium, and subsequently with zinc chloride, and allowing the resulting product to react with compound (a1) in the presence of a dichlorobis(triphenylphosphine) palladium catalyst.

1-4-2. Formation of Ring $A^1$, Ring $A^2$ or Ring $A^3$

With regard to a ring such as 1,4-cyclohexenylene, 1,4-phenylene, 2-fluoro-1,4-phenylene, 2,6-difluoro-1,4-phenylene, tetrahydropyran-2,5-diyl, 1,3-dioxane-2,5-diyl, 2,6,7-trioxabicyclo[2.2.2]octane-1,4-diyl, pyrimidine-2,5-diyl and pyridine-2,5-diyl, a starting material thereof is commercially available or a synthetic method thereof is well known.

1-4-3. Synthesis Example

An example of a method of preparing compound (1-1) is as described below. In the compounds, R, ring $A^1$ to ring $A^3$, $Y^1$ to $Y^5$, $L^1$ to $L^5$, X, l, m and n are defined in a manner identical with the definitions in item 1 described above.

Compound (1-1) can be prepared by the method described below. Compound (1-1) can be derived from compound (b1) and compound (b2) to be prepared according to a known method by being subjected to reaction in the presence of a tetrakis(triphenylphosphine)palladium catalyst, and a base such as potassium carbonate.

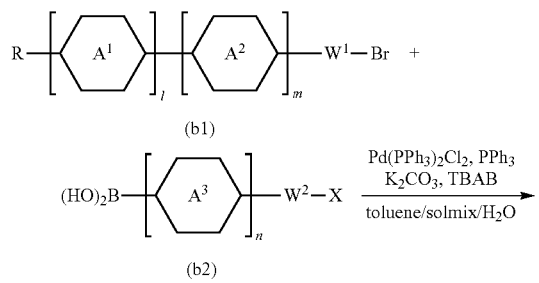

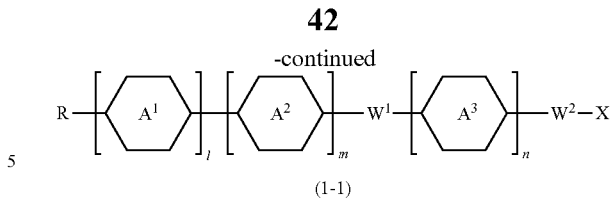

2. Liquid Crystal Composition

A liquid crystal composition of the invention is described. The composition contains at least one of compound (1) as component A. The composition may contain two or more compounds (1). The component of the liquid crystal compound may include only compound (1). In order to obtain excellent physical properties, the composition preferably contains at least one compound (1) in the range of approximately 1 to approximately 99% by weight. In a composition having a positive dielectric anisotropy, a preferred content of compound (1) is in the range of approximately 5 to approximately 60% by weight. In a composition having a negative dielectric anisotropy, the preferred content of compound (1) is approximately 30% by weight or less. The composition may also contain compound (1) and various kinds of liquid crystal compounds that are not described herein.

A preferred liquid crystal composition contains a compound selected from components B, C, D and E shown below. When a composition is prepared, a component can also be selected, for example, in consideration of the dielectric anisotropy of compound (1). When a composition having the positive dielectric anisotropy is prepared for the mode such as TFT, IPS and FFS, a main component thereof includes component A, B or E. When a composition having the positive dielectric anisotropy is prepared for the mode such as STN and TN, a main component thereof includes component A, C or E. When a composition having the negative dielectric anisotropy is prepared for the mode such as VA and PSA, a main component thereof includes component D or E, and component A is added for the purpose of adjusting a voltage-transmittance curve of the device. The composition in which the component is suitably selected has a high maximum temperature, a low minimum temperature, a small viscosity, a suitable optical anisotropy, a large dielectric anisotropy and a suitable elastic constant.

Component B includes compounds (2) to (4). Component C is compound (5). Component D includes compounds (6) to (12). Component E includes compounds (13) to (15). The components are described in the order.

Component B is a compound having a halogen-containing or fluorine-containing group at a right terminal. Specific preferred examples of component B include compounds (2-1) to (2-16), compounds (3-1) to (3-113) or compounds (4-1) to (4-57). In the compounds, $R^{11}$ and $X^{11}$ are defined in a manner identical with the definitions in item 13 as described above.

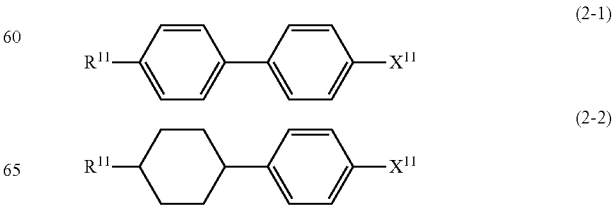

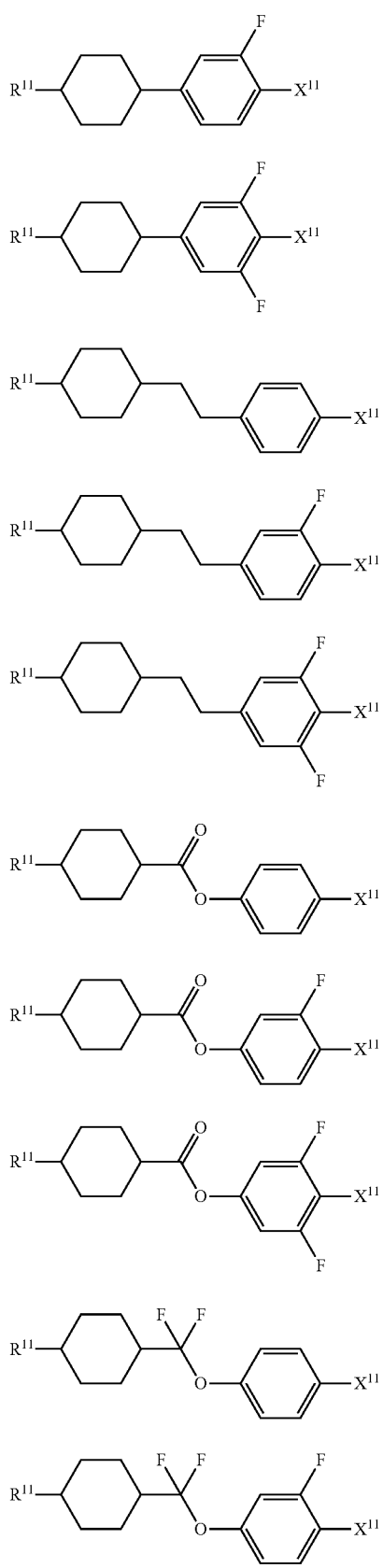
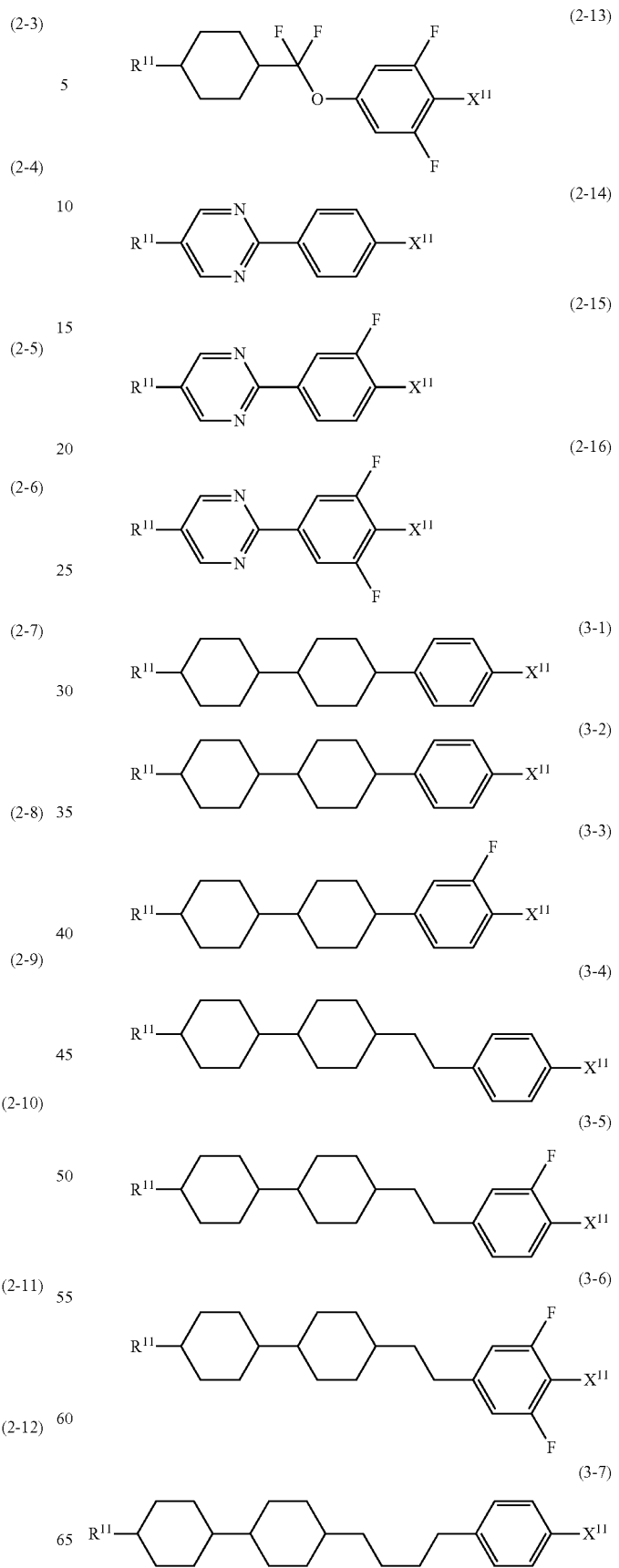

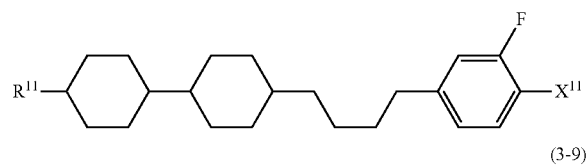
(3-8)
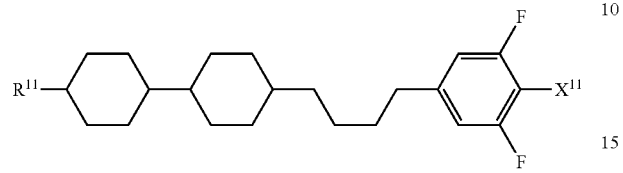
(3-9)
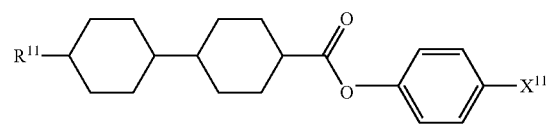
(3-10)
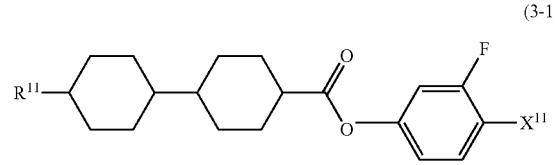
(3-11)
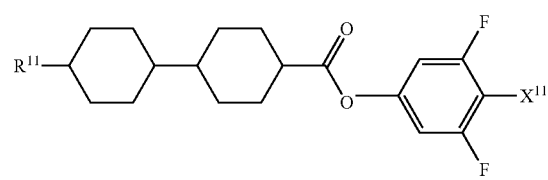
(3-12)
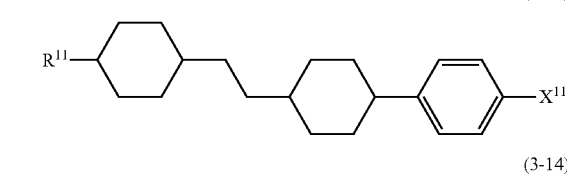
(3-13)
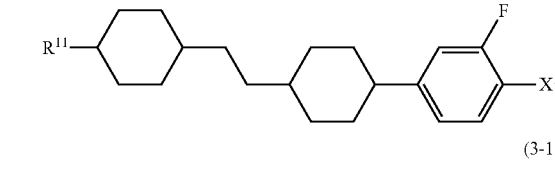
(3-14)
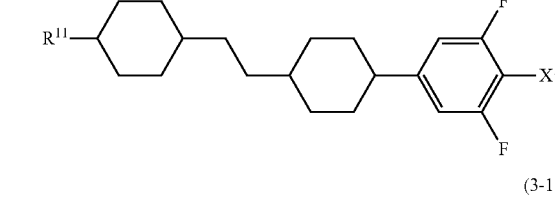
(3-15)
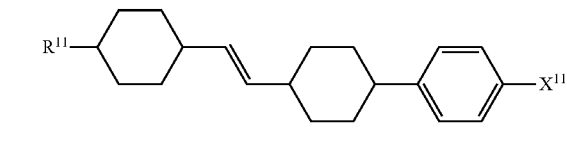
(3-16)
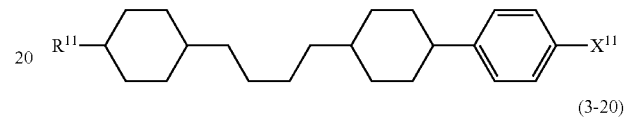
(3-17)
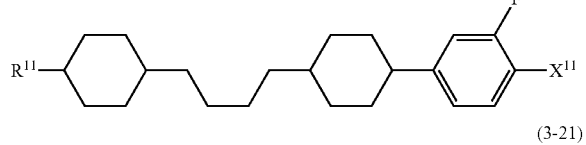
(3-18)
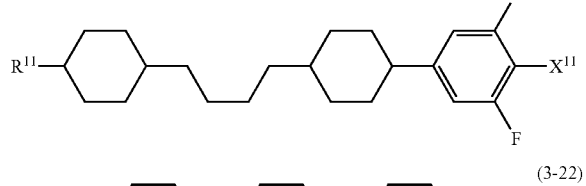
(3-19)
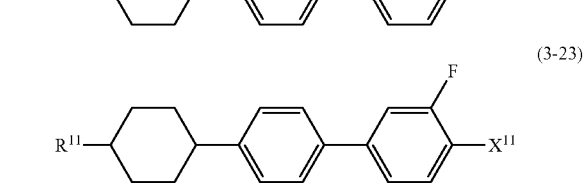
(3-20)
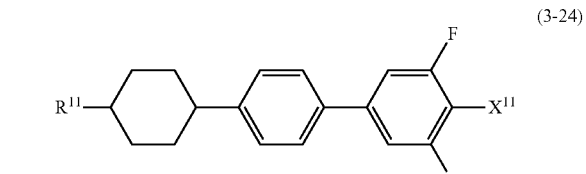
(3-21)
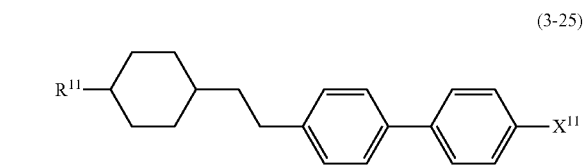
(3-22)
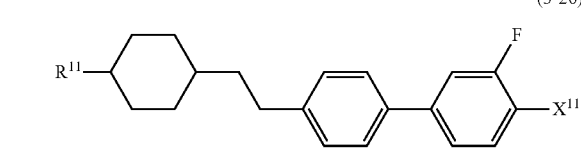
(3-23)
(3-24)
(3-25)
(3-26)

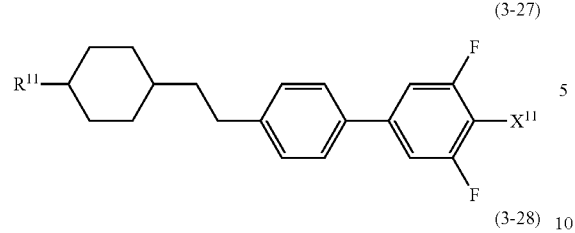
(3-27)
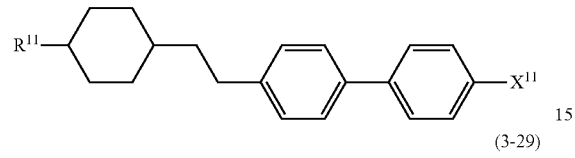
(3-28)
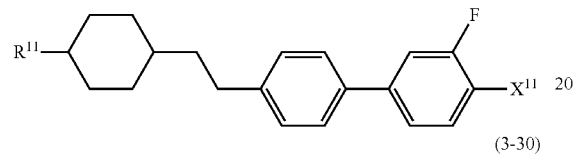
(3-29)
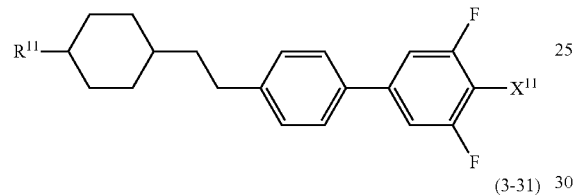
(3-30)
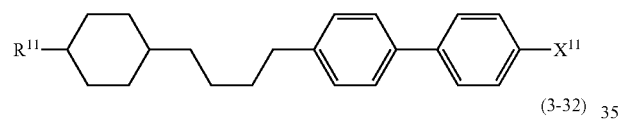
(3-31)
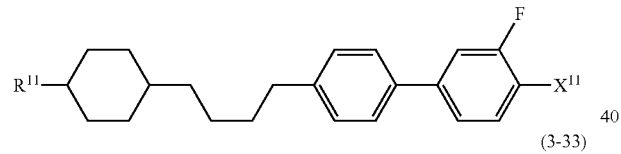
(3-32)
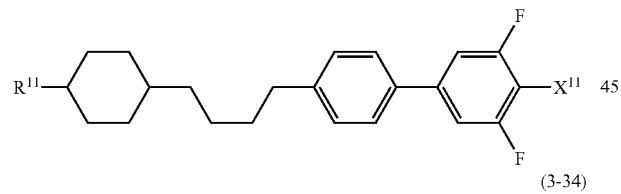
(3-33)
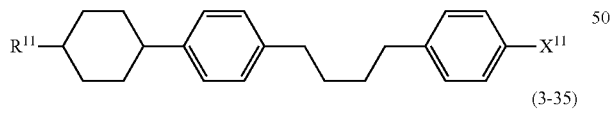
(3-34)
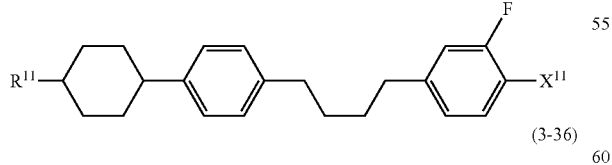
(3-35)
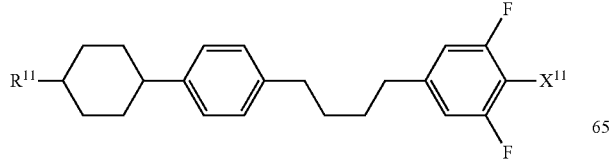
(3-36)
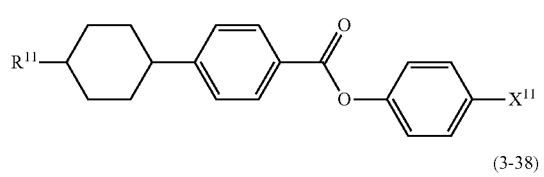
(3-37)
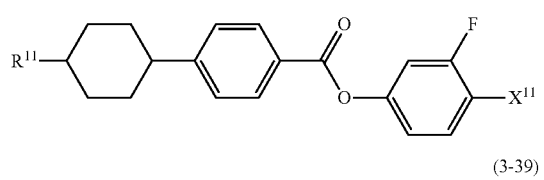
(3-38)
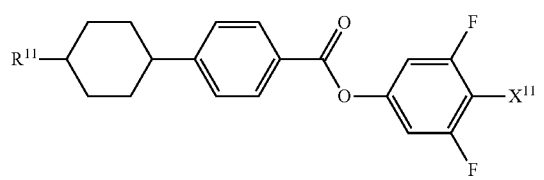
(3-39)
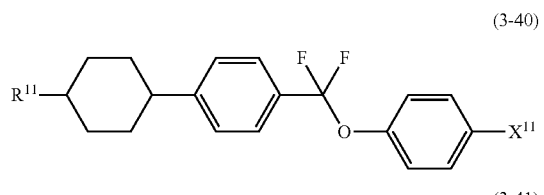
(3-40)
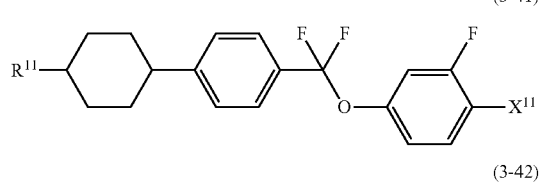
(3-41)
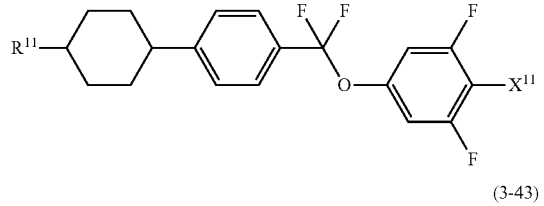
(3-42)
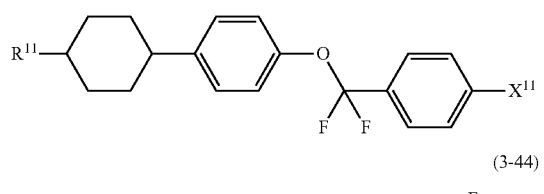
(3-43)
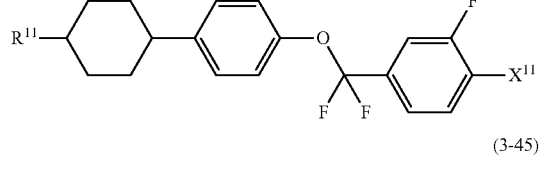
(3-44)
(3-45)

(3-46)
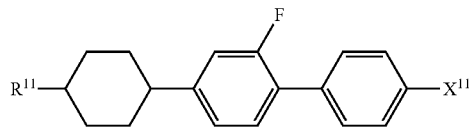
(3-47)
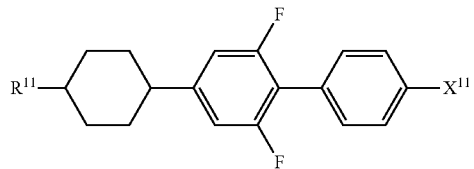
(3-48)
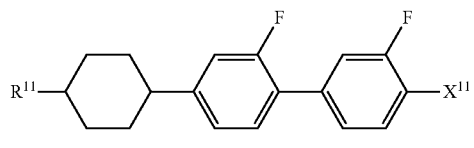
(3-49)
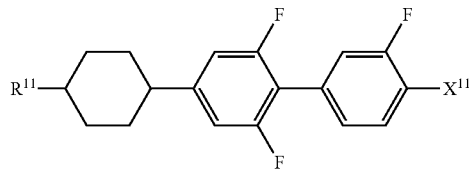
(3-50)
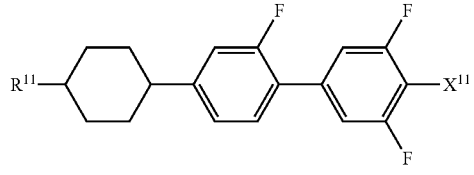
(3-51)
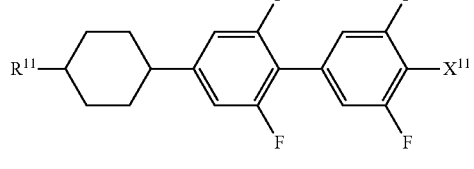
(3-52)
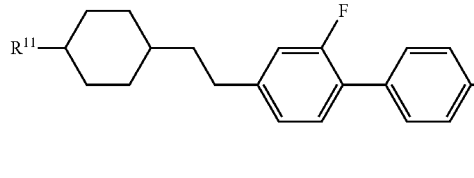
(3-53)
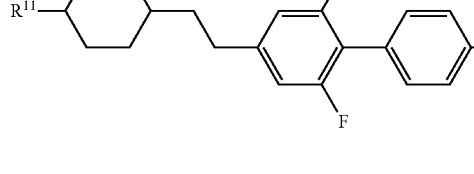
(3-54)
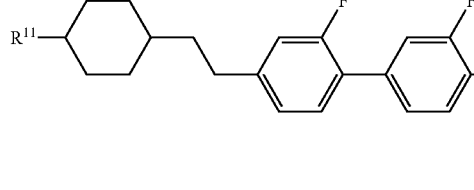
(3-55)
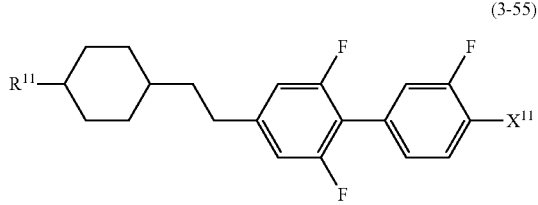
(3-56)
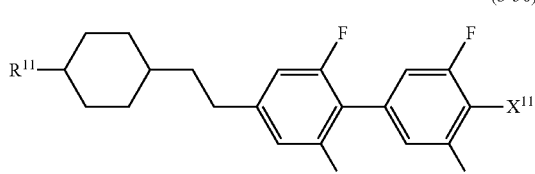
(3-57)
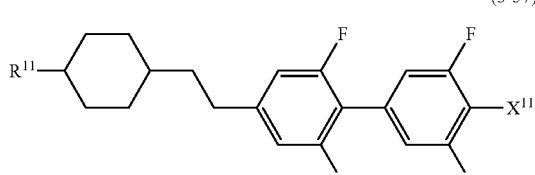
(3-58)
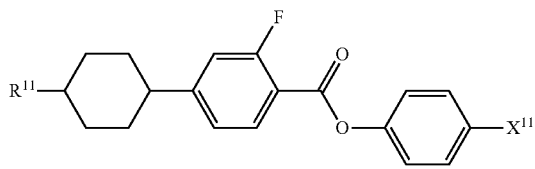
(3-59)
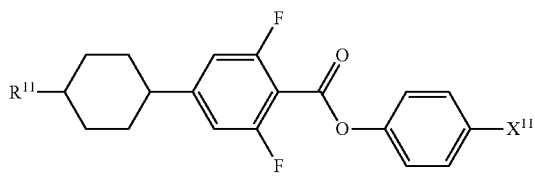
(3-60)
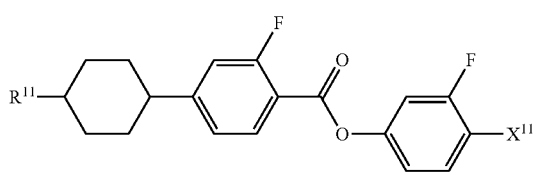
(3-61)
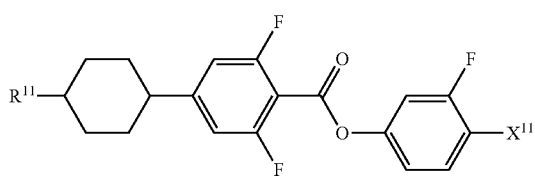
(3-62)
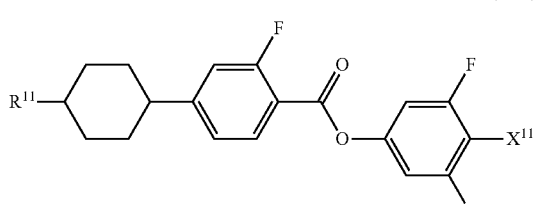

(3-63) 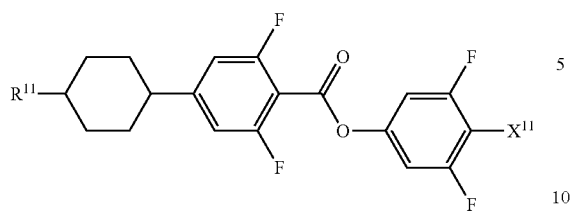
(3-64) 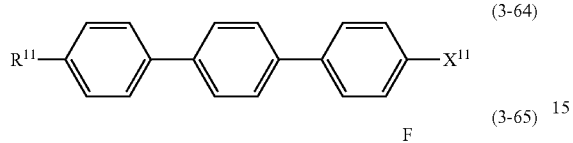
(3-65) 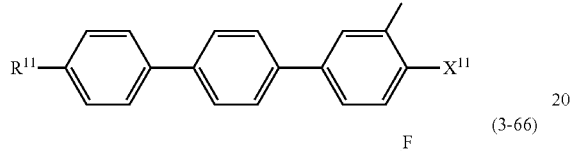
(3-66) 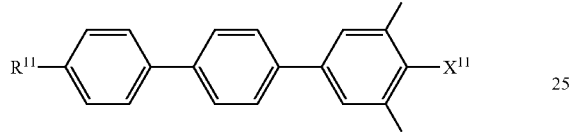
(3-67) 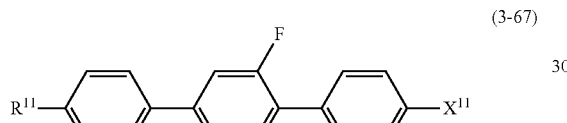
(3-68) 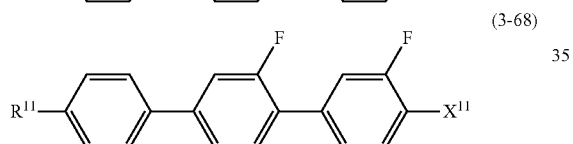
(3-69) 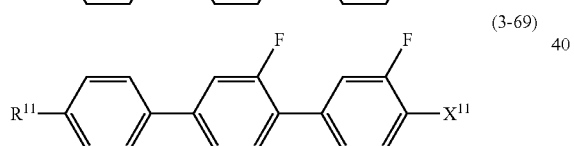
(3-70) 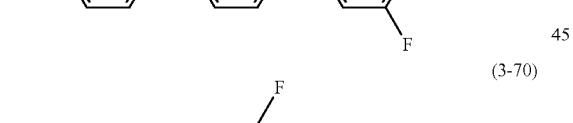
(3-71) 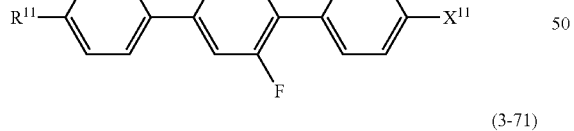
(3-72) 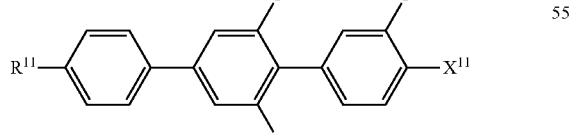
(3-73) 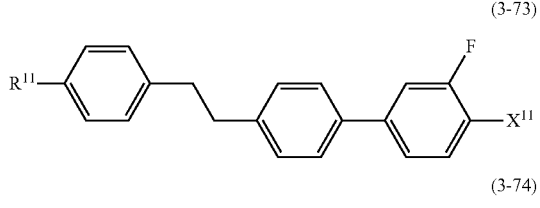
(3-74) 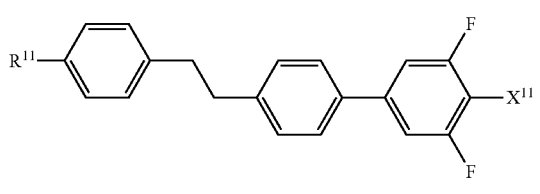
(3-75) 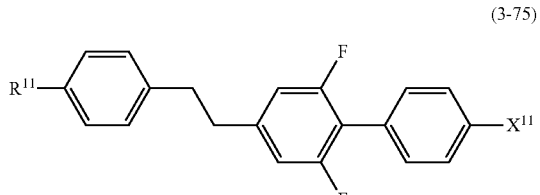
(3-76) 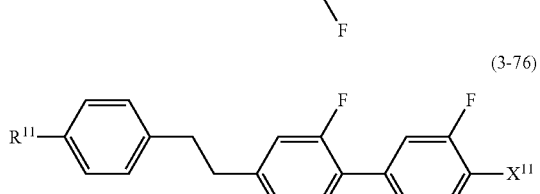
(4-1) 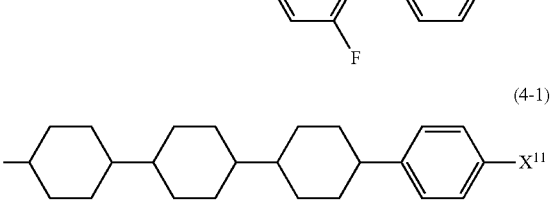
(4-2) 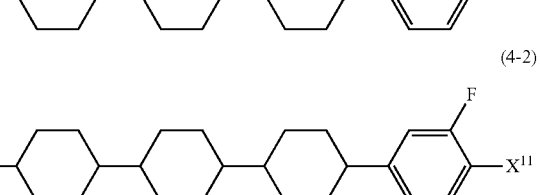
(4-3) 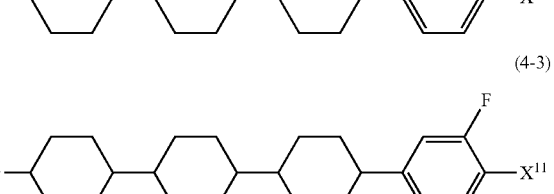
(4-4) 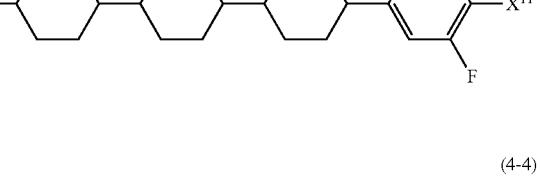
(4-5) 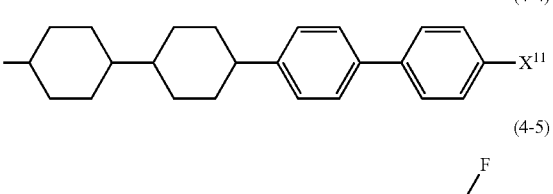

(4-6) 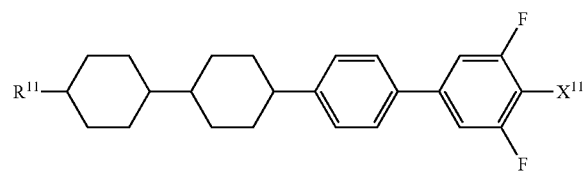
(4-7) 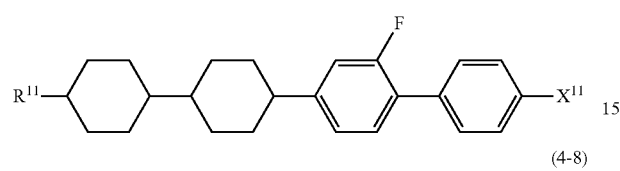
(4-8) 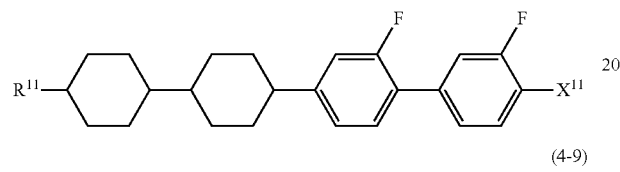
(4-9) 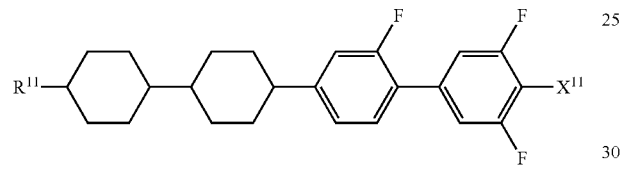
(4-10) 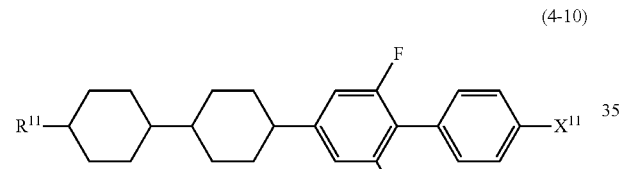
(4-11) 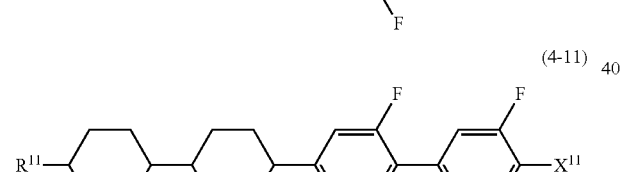
(4-12) 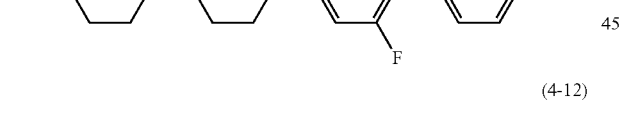
(4-13) 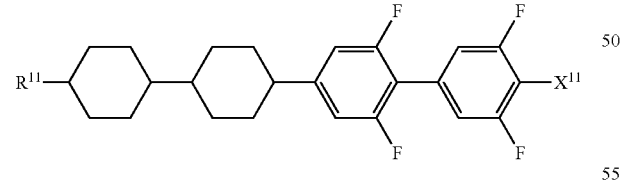
(4-14) 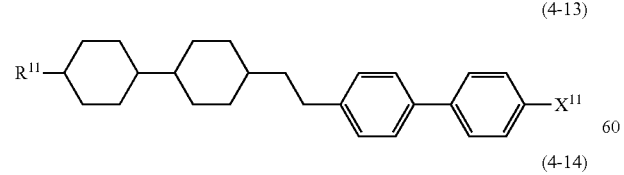
(4-15) 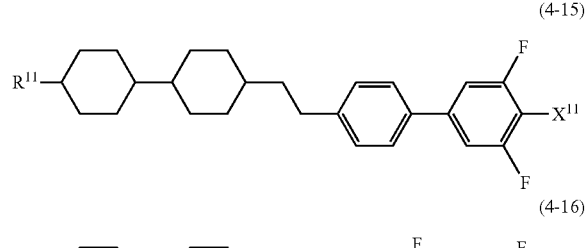
(4-16) 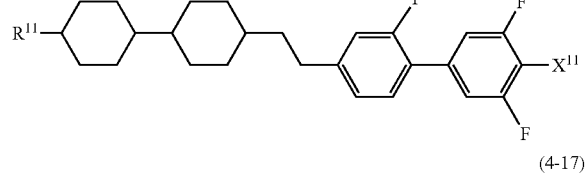
(4-17) 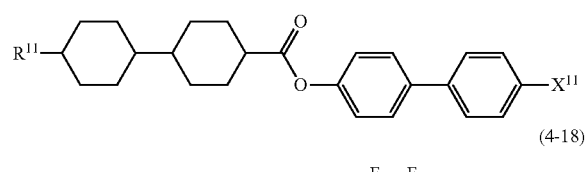
(4-18) 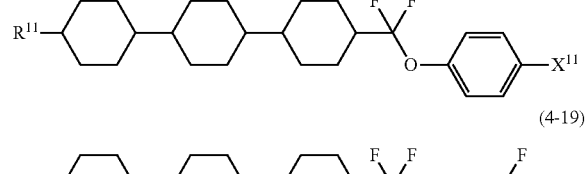
(4-19) 
(4-20) 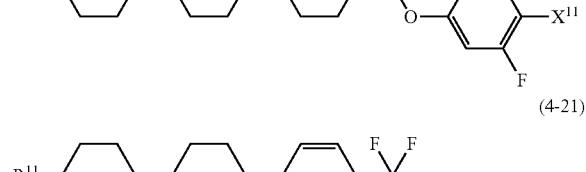
(4-21) 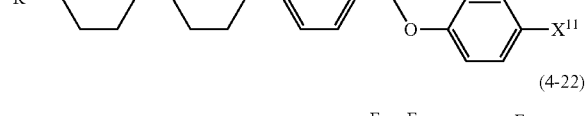
(4-22) 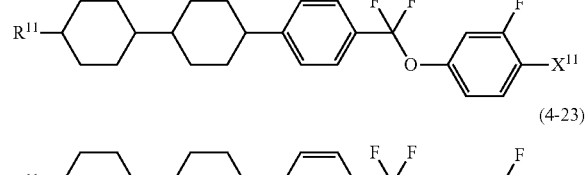
(4-23) 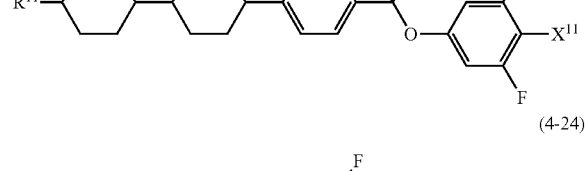
(4-24) 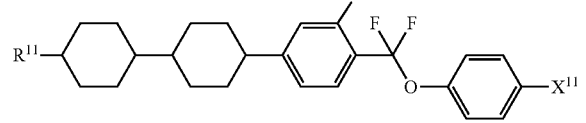

(4-25) 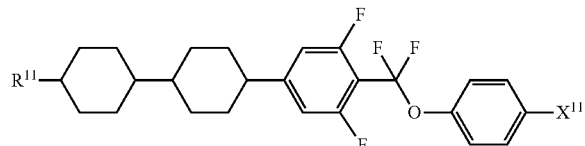
(4-26) 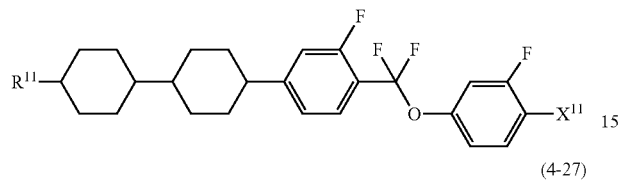
(4-27) 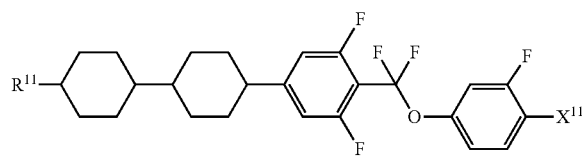
(4-28) 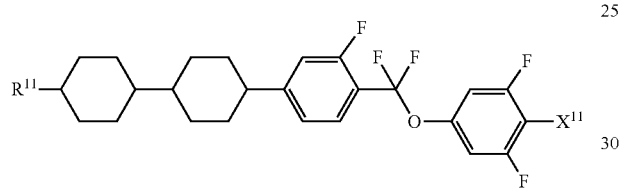
(4-29) 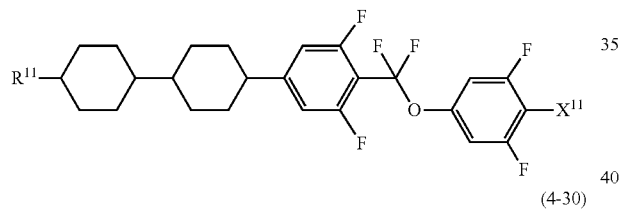
(4-30) 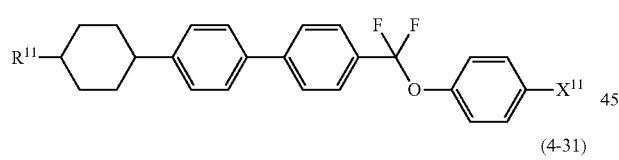
(4-31) 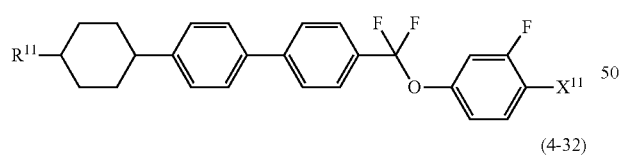
(4-32) 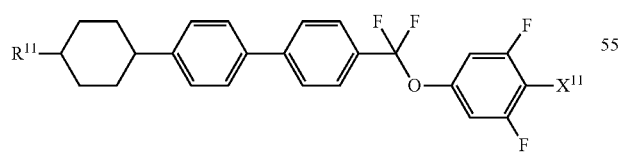
(4-33) 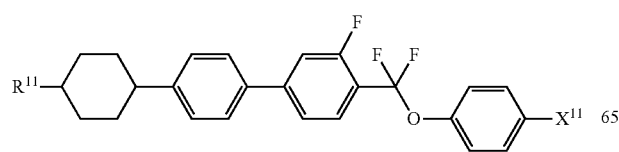
(4-34) 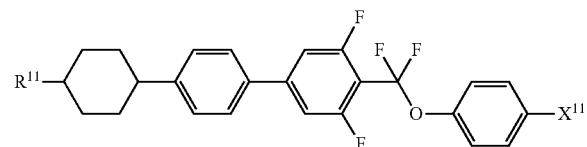
(4-35) 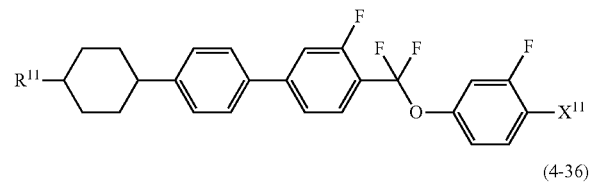
(4-36) 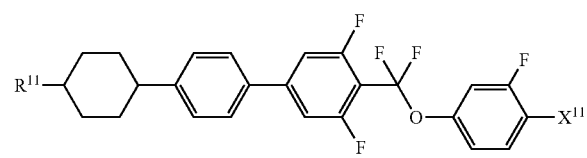
(4-37) 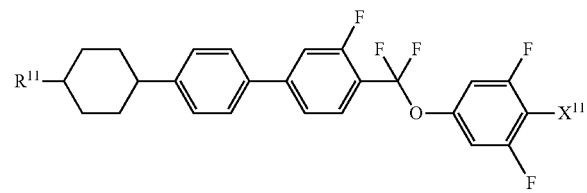
(4-38) 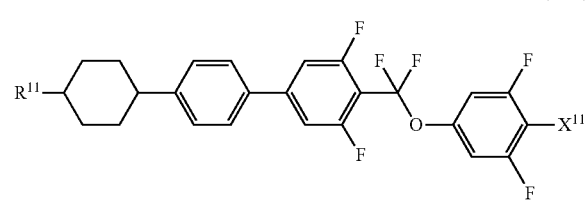
(4-39) 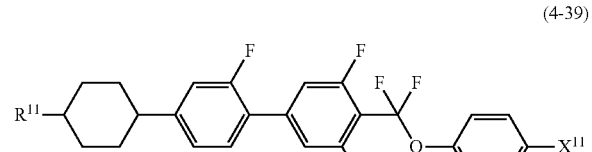
(4-40) 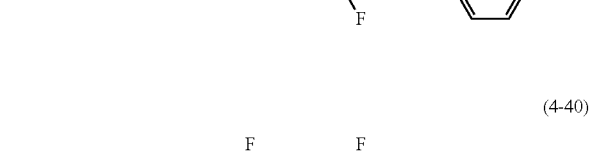
(4-41) 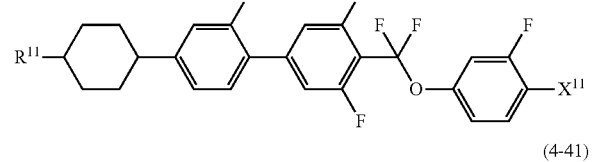

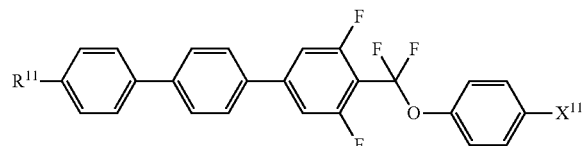 (4-42)
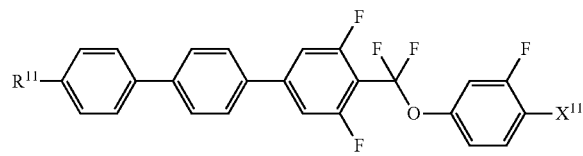 (4-43)
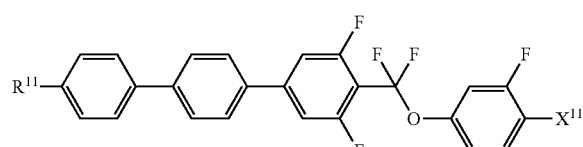 (4-44)
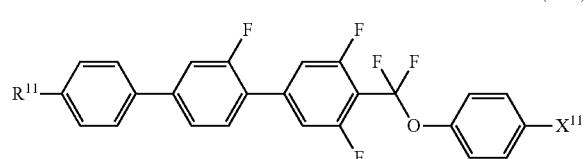 (4-45)
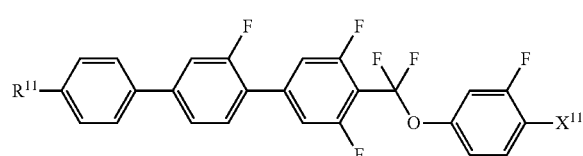 (4-46)
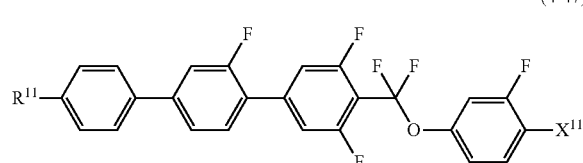 (4-47)
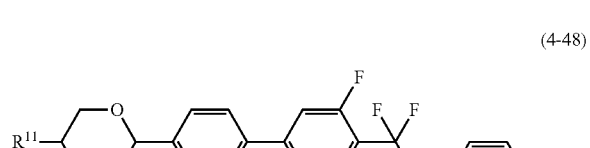 (4-48)
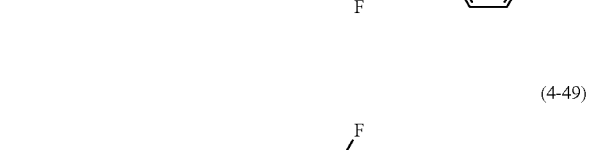 (4-49)
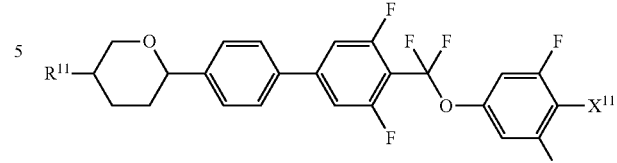 (4-50)
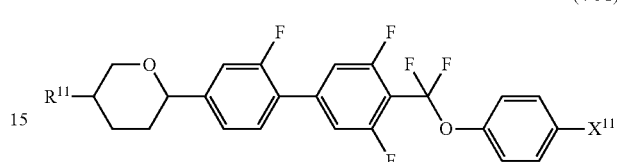 (4-51)
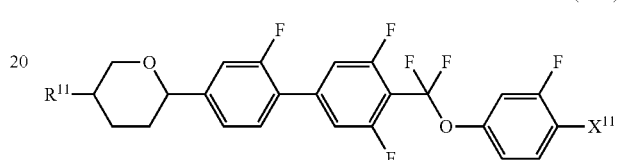 (4-52)
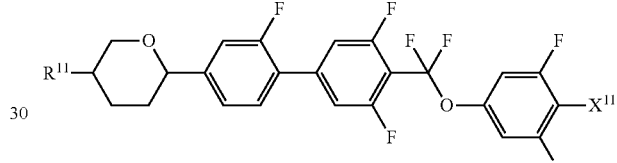 (4-53)
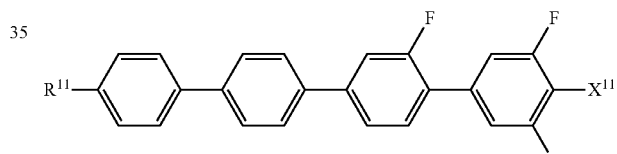 (4-54)
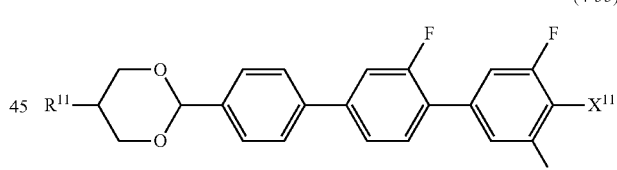 (4-55)
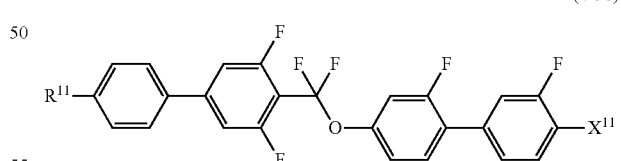 (4-56)
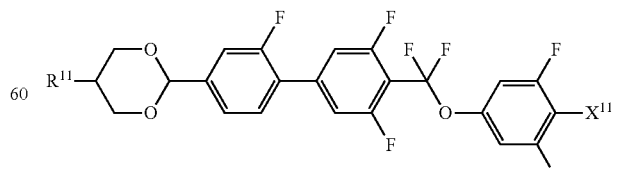 (4-57)
Component B has the positive dielectric anisotropy and a superb stability to heat, light and so forth, and therefore is used when a composition for the mode such as TFT, IPS and FFS is prepared. A content of component (B) is suitably in the range of approximately 1 to approximately 99% by weight, preferably in the range of approximately 10 to approximately 97% by weight, and further preferably in the range of approximately 40 to approximately 95% by weight, based on the weight of the composition. In the composition, the viscosity can be adjusted by further adding compounds (13) to (15) (component E).

Component C is compound (5) in which a right-terminal group is —C≡N or —C≡C—C≡N. Specific preferred examples of component C include compounds (5-1) to (5-64). In the compounds (component C), $R^{12}$ and $X^{12}$ are defined in a manner identical with the definitions in item 14 described above.

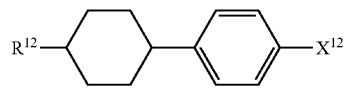 (5-1)

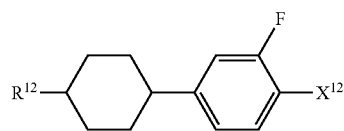 (5-2)

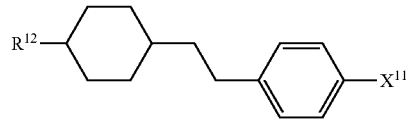 (5-3)

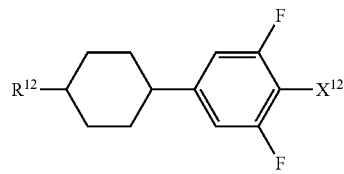 (5-4)

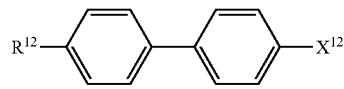 (5-5)

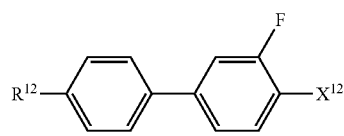 (5-6)

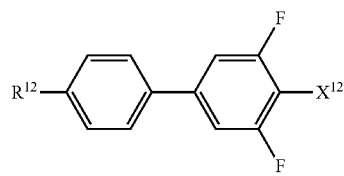 (5-7)

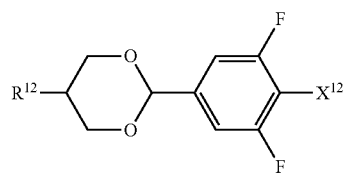 (5-8)

-continued

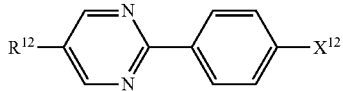 (5-9)

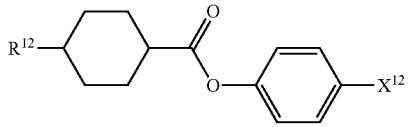 (5-10)

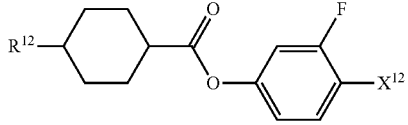 (5-11)

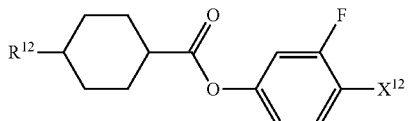 (5-12)

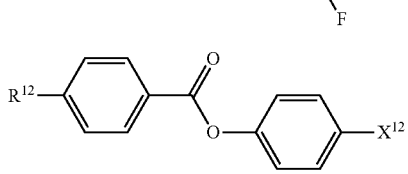 (5-13)

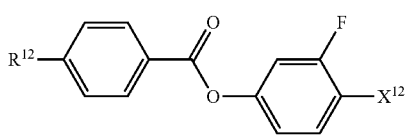 (5-14)

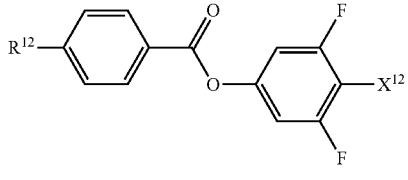 (5-15)

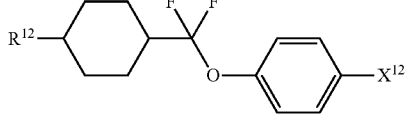 (5-16)

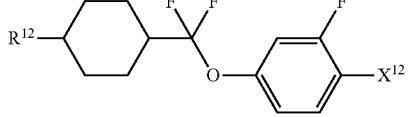 (5-17)

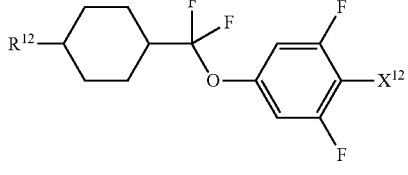 (5-18)

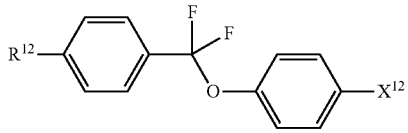 (5-19)

-continued
(5-20) 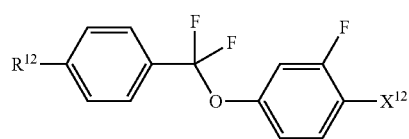
(5-21) 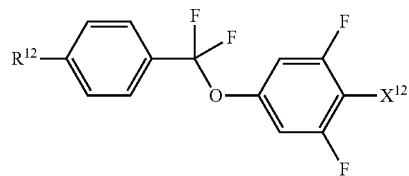
(5-22) 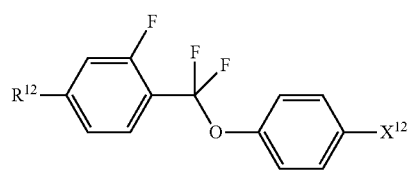
(5-23) 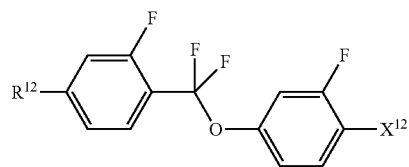
(5-24) 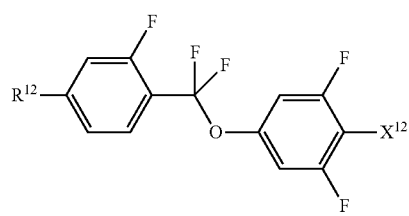
(5-25) 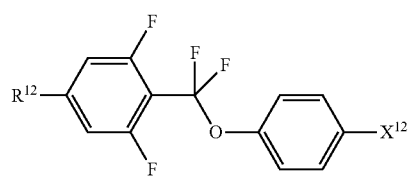
(5-26) 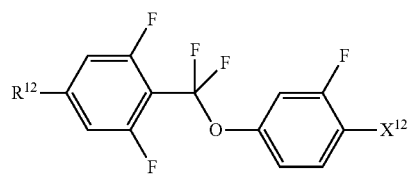
(5-27) 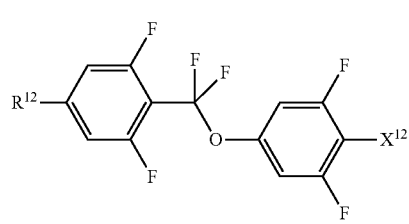
(5-28) 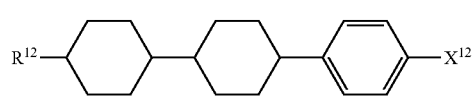
-continued
(5-29) 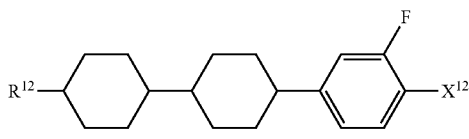
(5-30) 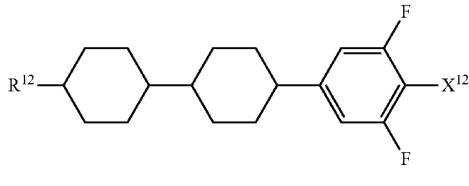
(5-31) 
(5-32) 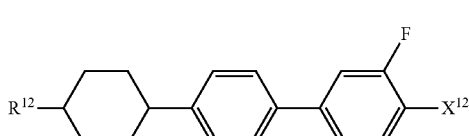
(5-33) 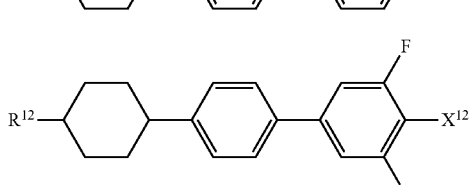
(5-34) 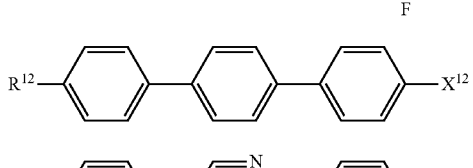
(5-35) 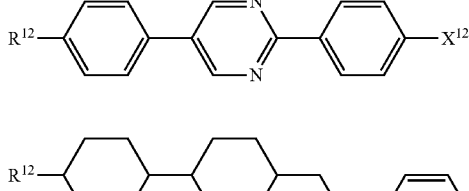
(5-36) 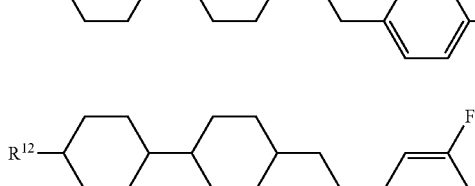
(5-37) 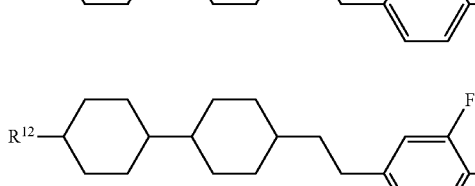
(5-38) 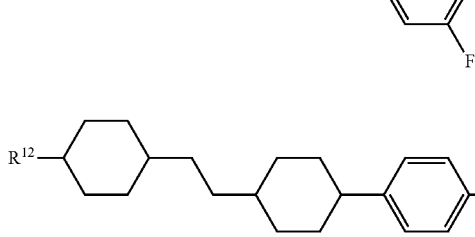
(5-39)

(5-40) 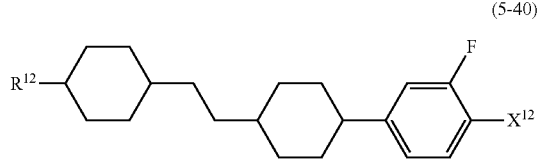
(5-41) 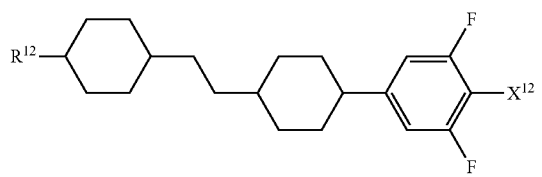
(5-42) 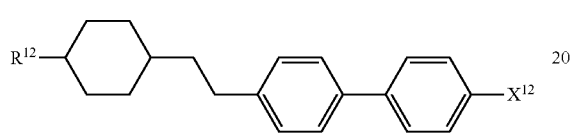
(5-43) 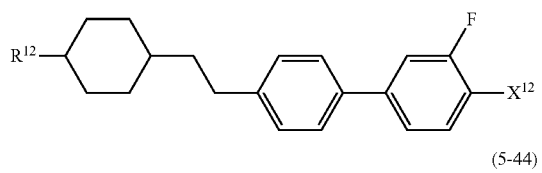
(5-44) 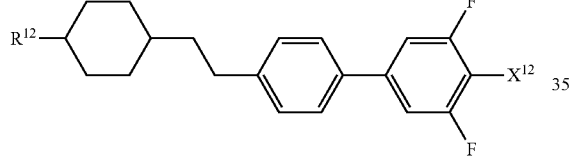
(5-45) 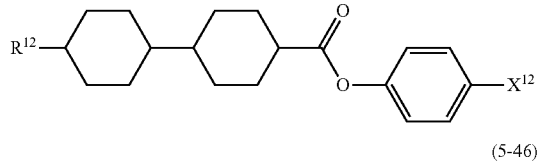
(5-46) 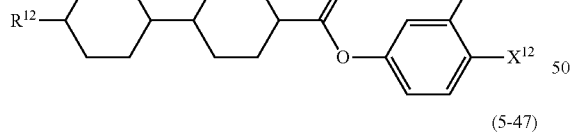
(5-47) 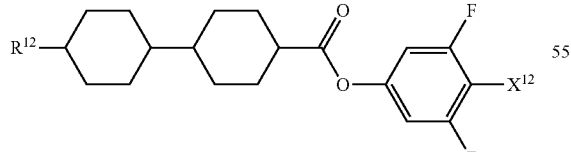
(5-48) 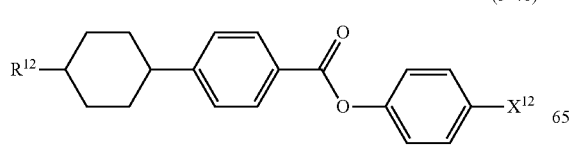
(5-49) 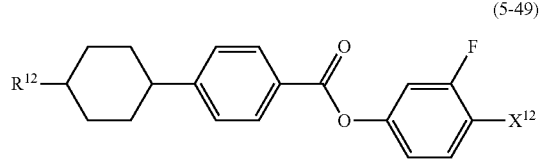
(5-50) 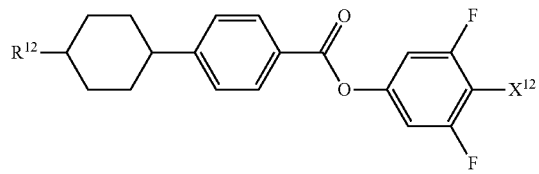
(5-51) 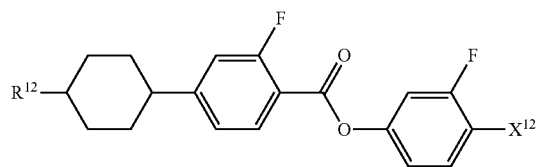
(5-52) 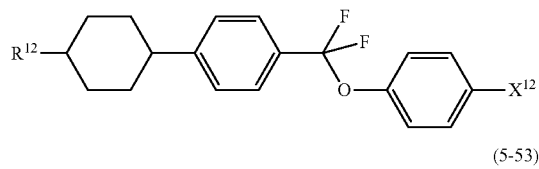
(5-53) 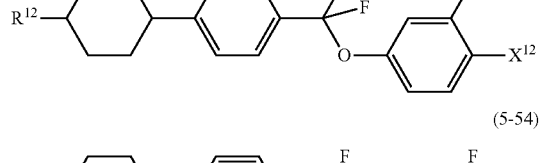
(5-54) 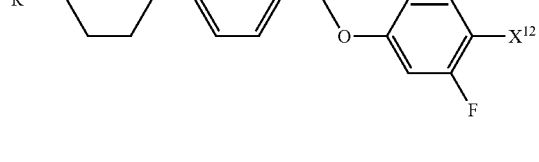
(5-55) 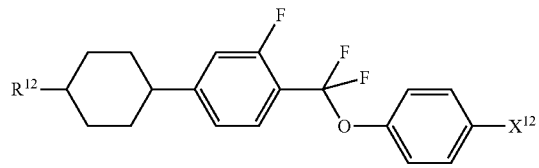
(5-56) 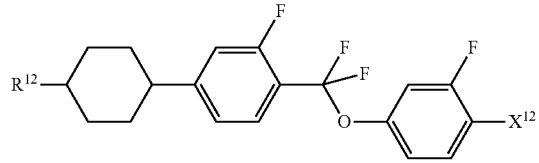

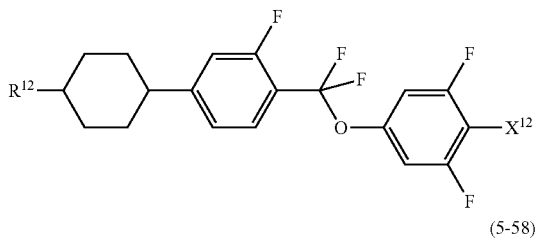

(5-57)

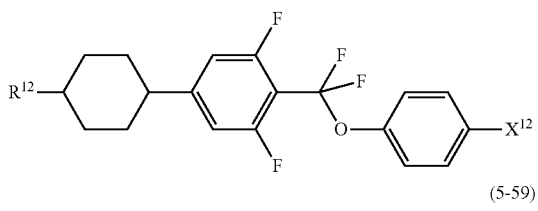

(5-58)

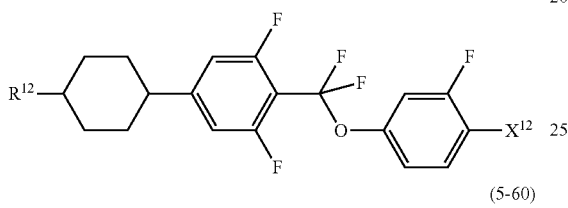

(5-59)

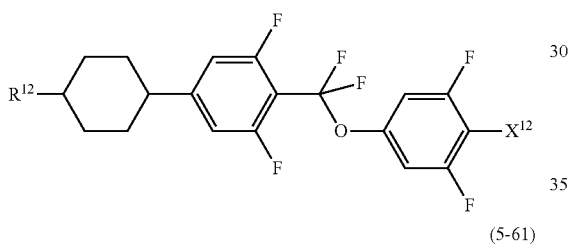

(5-60)

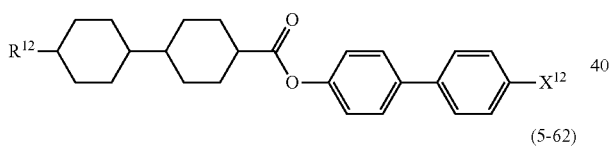

(5-61)

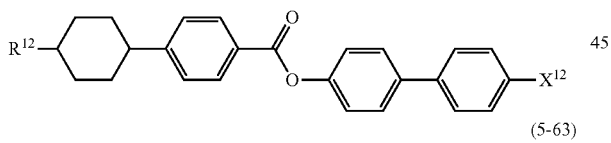

(5-62)

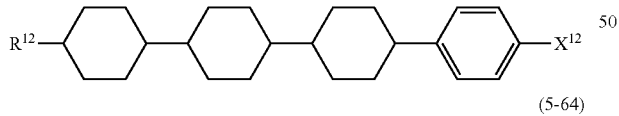

(5-63)

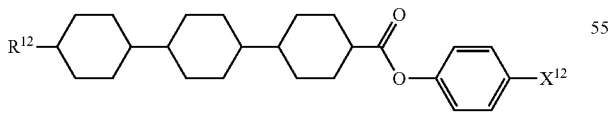

(5-64)

Component C has the positive dielectric anisotropy, and a value thereof is large, and therefore is mainly used when a composition for the STN mode, the TN mode or the PSA mode is prepared. The dielectric anisotropy of the composition can be increased by adding component C. Component C is effective in extending the temperature range of the liquid crystal phase, adjusting the viscosity or the optical anisotropy. Component C is useful also in adjusting the voltage-transmittance curve of the device.

When the composition for the STN mode or the TN mode is prepared, a content of component C is suitably in the range of approximately 1 to approximately 99%, preferably in the range of approximately 10 to approximately 97% by weight, and further preferably in the range of approximately 40 to approximately 95% by weight, based on the weight of the composition. In the composition, the temperature range of the liquid crystal phase, the viscosity, the optical anisotropy, the dielectric anisotropy and so forth can be adjusted by adding component E.

Component D includes compounds (6) to (12). The compounds have a benzene ring in which two of hydrogen in a lateral position thereof is replaced by two of halogen, such as 2,3-difluoro-1,4-phenylene. Specific preferred examples of component D include compounds (6-1) to (6-8), compounds (7-1) to (7-17), compound (8-1), compounds (9-1) to (9-3), compounds (10-1) to (10-11), compounds (11-1) to (11-3) or compounds (12-1) to (12-3). In the compounds (component D), $R^{13}$, $R^{14}$ and $R^{15}$ are defined in a manner identical with the definitions in item 15 described above.

(6-1)

(6-2)

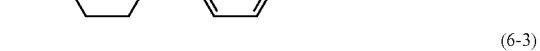

(6-3)

(6-4)

(6-5)

(6-6)

(6-7)

(6-8) 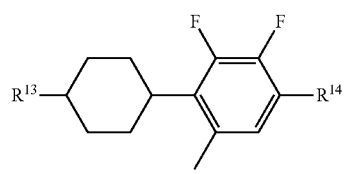
(7-1) 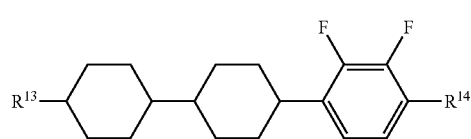
(7-2) 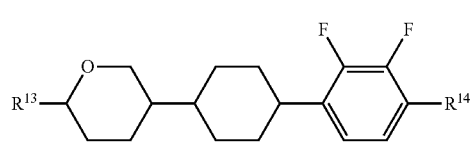
(7-3) 
(7-4) 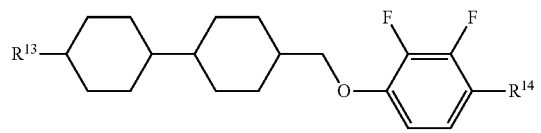
(7-5) 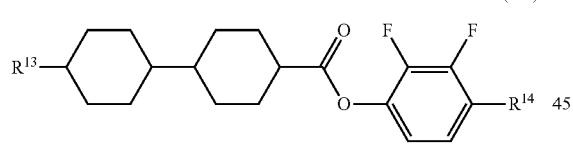
(7-6) 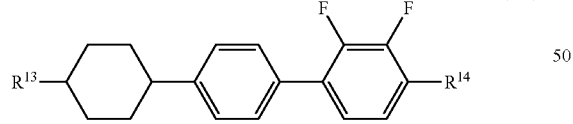
(7-7) 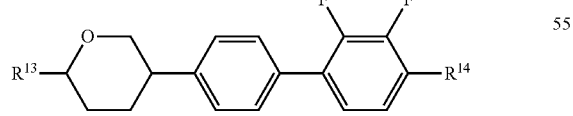
(7-8) 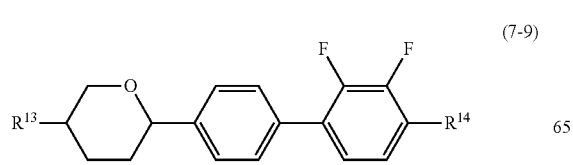
(7-9) 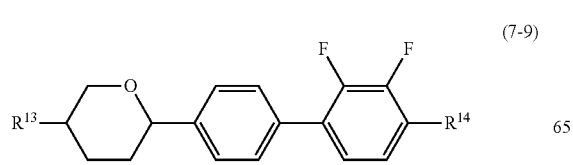
(7-10) 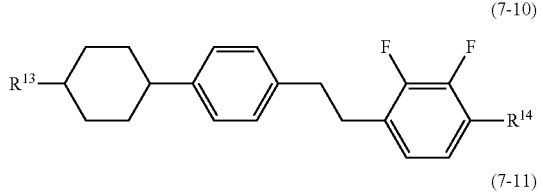
(7-11) 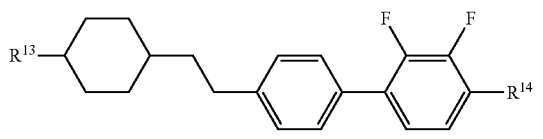
(7-12) 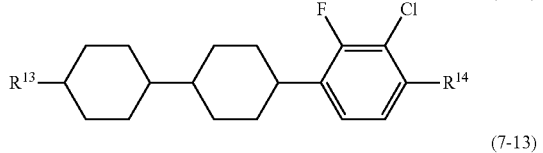
(7-13) 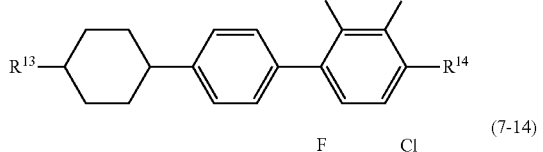
(7-14) 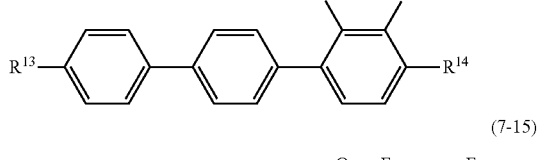
(7-15) 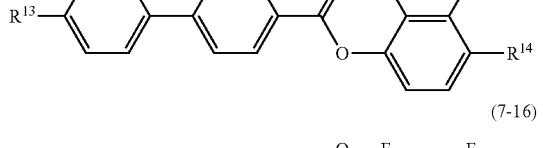
(7-16) 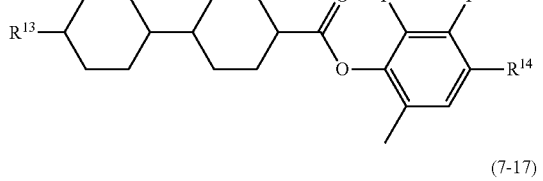
(7-17) 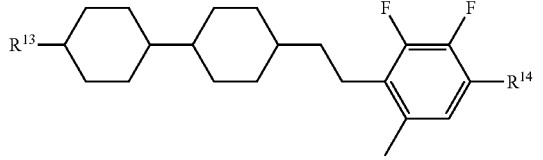
(8-1) 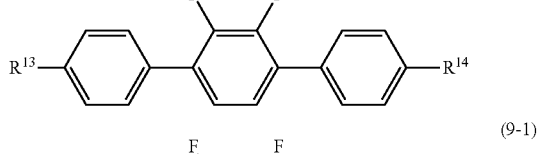
(9-1) 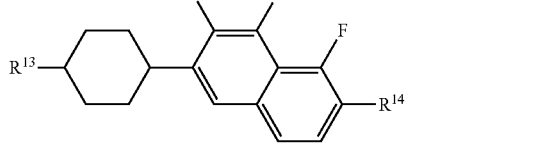

(9-2)
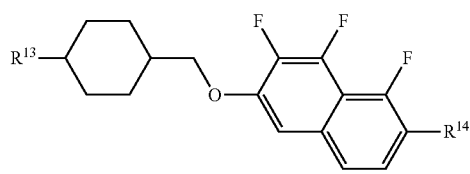
(9-3)
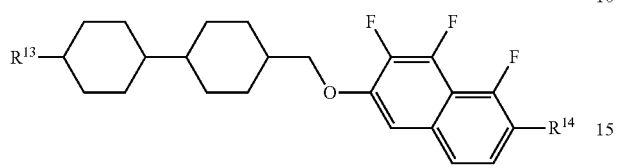
(10-1)
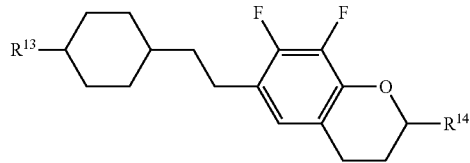
(10-2)
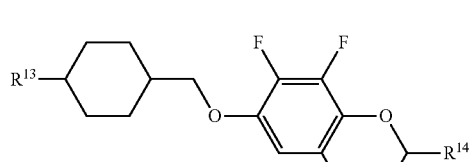
(10-3)
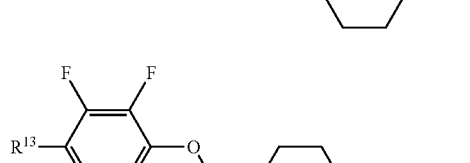
(10-4)
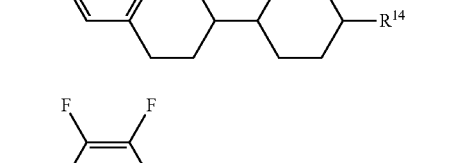
(10-5)
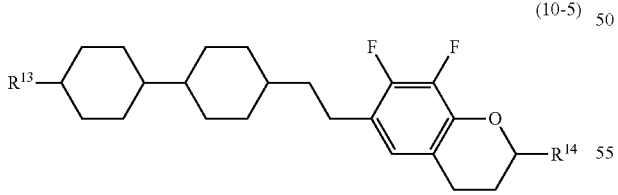
(10-6)
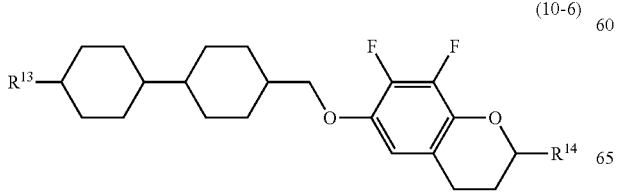
(10-7)
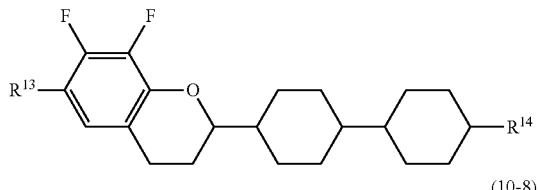
(10-8)
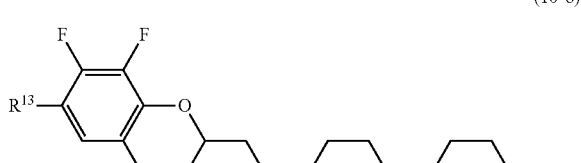
(10-9)
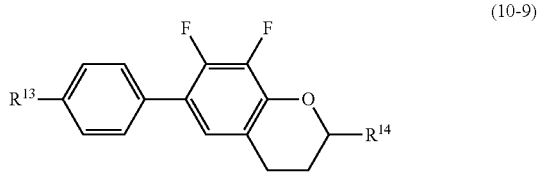
(10-10)
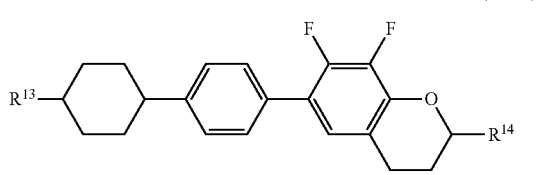
(10-11)
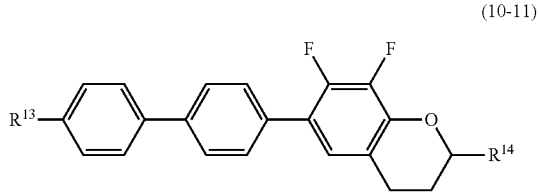
(11-1)
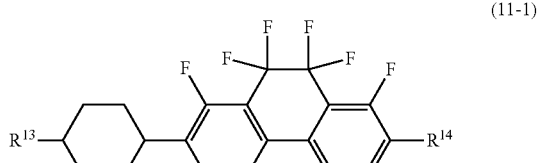
(11-2)
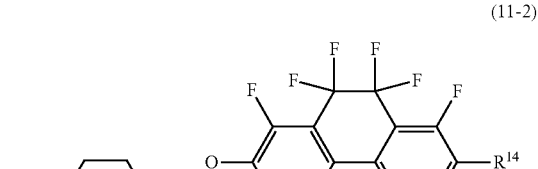
(11-3)
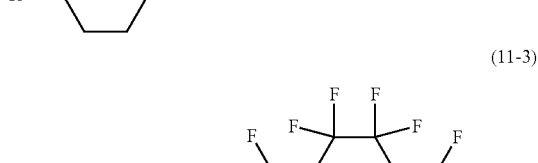
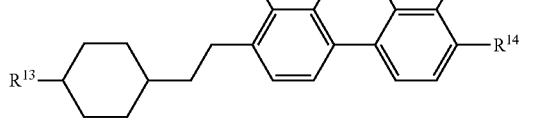

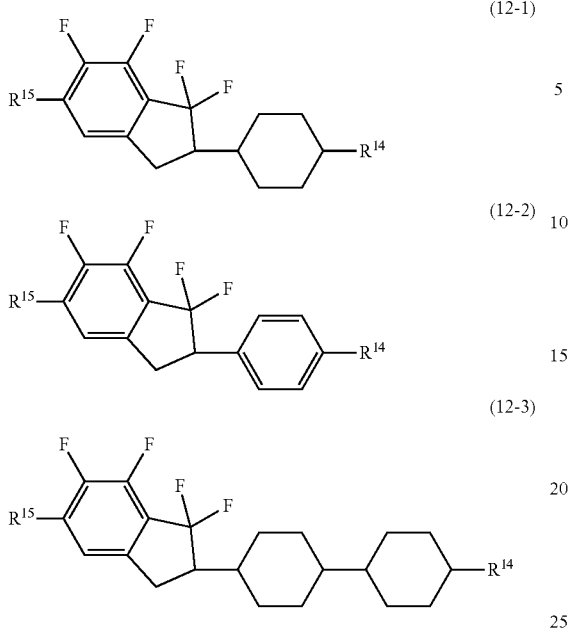

Component D is a compound having the negative dielectric anisotropy. Component D is mainly used when a composition for the VA mode or the PSA mode is prepared. Among types of compound D, compound (6) is a bicyclic compound, and therefore is effective mainly in adjusting the viscosity, the optical anisotropy or the dielectric anisotropy. Compounds (7) and (8) are a tricyclic compound, and therefore are effective in increasing the maximum temperature, the optical anisotropy or the dielectric anisotropy. Compounds (9) to (12) are effective in increasing the dielectric anisotropy.

When the composition for the VA mode or PSA mode is prepared, a content of component D is preferably approximately 40% or more by weight, and further preferably in the range of approximately 50 to approximately 95% by weight, based on the weight of the composition. When component D is added to the composition having the positive dielectric anisotropy, a preferred content of component D is approximately 30% by weight or less based on the weight of the composition. The voltage-transmittance curve of the device can be adjusted by adding component D.

Component E is a compound in which two terminal groups are alkyl or the like. Specific preferred examples of component E include compounds (13-1) to (13-11), compounds (14-1) to (14-19) or compounds (15-1) to (15-7). In the compounds (component E), $R^{16}$ and $R^{17}$ are defined in a manner identical with the definitions in item 16 described above.

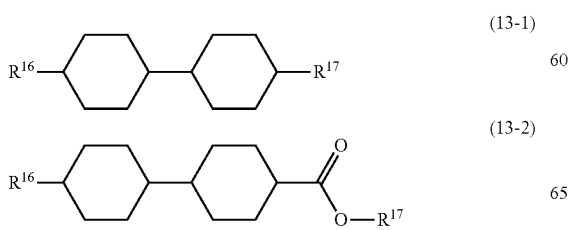

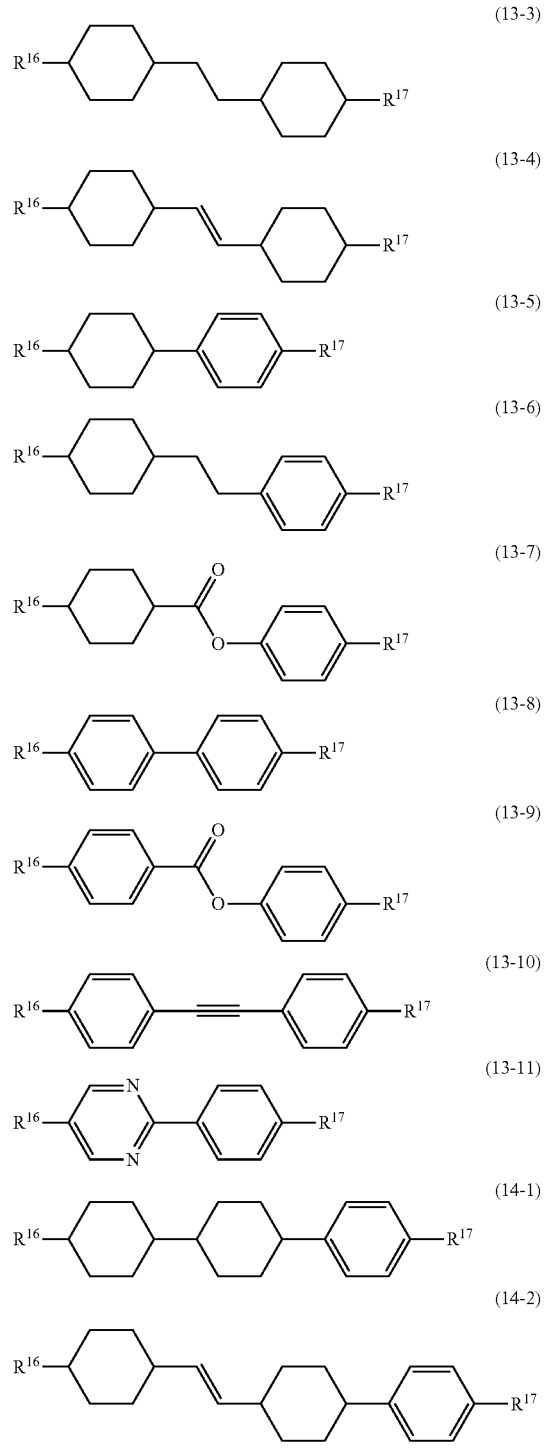

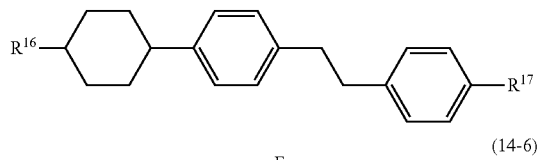 (14-5)
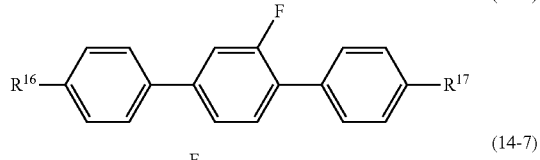 (14-6)
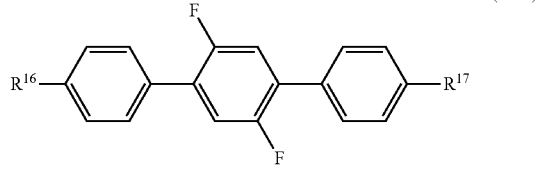 (14-7)
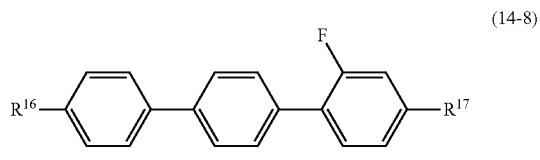 (14-8)
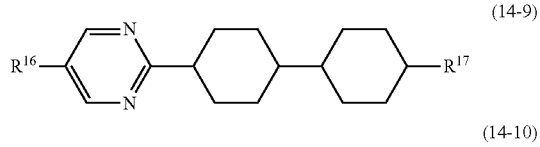 (14-9)
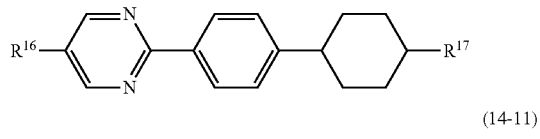 (14-10)
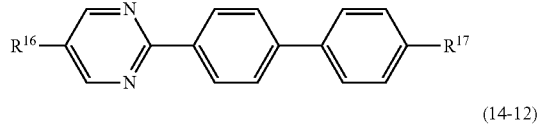 (14-11)
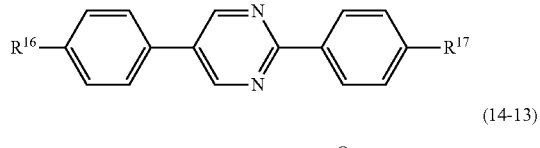 (14-12)
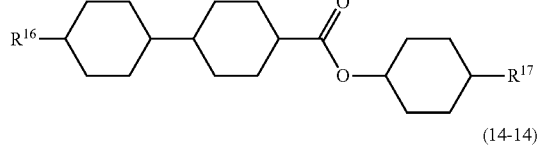 (14-13)
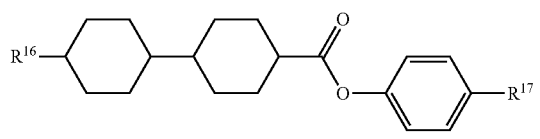 (14-14)
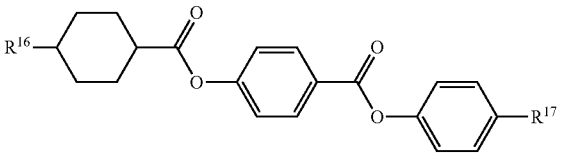 (14-15)
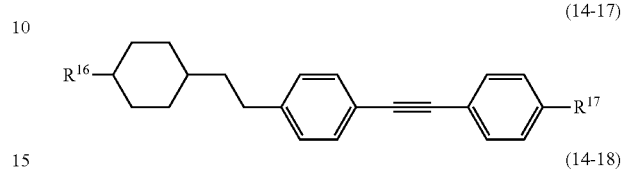 (14-16)
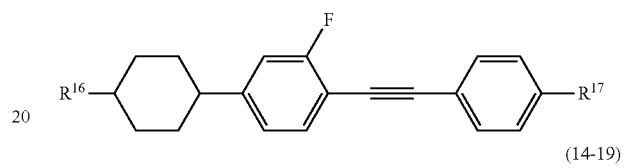 (14-17)
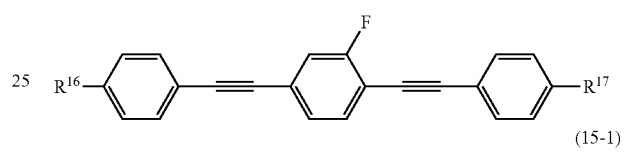 (14-18)
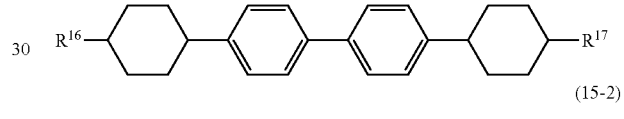 (14-19)
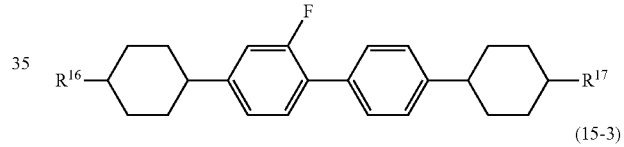 (15-1)
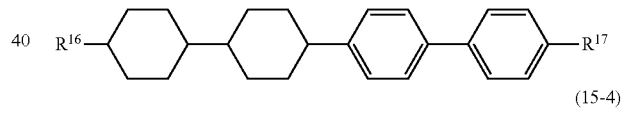 (15-2)
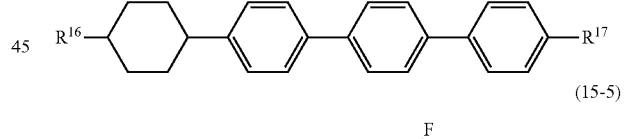 (15-3)
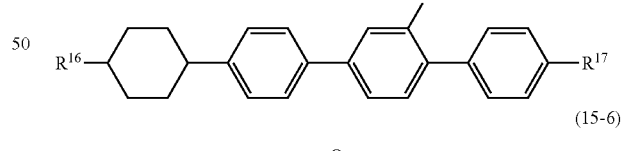 (15-4)
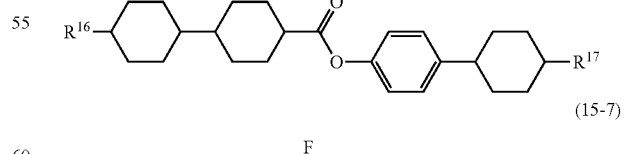 (15-5)
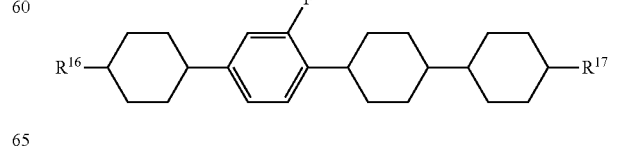 (15-6)
(15-7)
Component E has a small absolute value of dielectric anisotropy, and therefore is a compound close to neutrality.

Compound (13) is effective mainly in adjusting the viscosity or the optical anisotropy. Compounds (14) and (15) are effective in extending the temperature range of the nematic phase by increasing the maximum temperature, or adjusting the optical anisotropy.

If a content of component E is increased, the dielectric anisotropy of the composition decreases, but the viscosity decreases. Therefore, the content is preferably as large as possible, as long as the composition meets a desired value of threshold voltage of the device. Accordingly, when the composition is prepared, the content of component E is preferably approximately 30% by weight or more, and further preferably approximately 40% by weight or more, based on the weight of the composition.

Preparation of the composition is performed by a method for dissolving required components at a high temperature or the like. According to an application, the additive may be added to the composition. Specific examples of the additive include an optically active compound, a polymerizable compound, a polymerization initiator, an antioxidant, an ultraviolet light absorber, a light stabilizer, a heat stabilizer, an antifoaming agent and a dye. Such additives are well known to those skilled in the art, and described in literature.

The composition may further contain at least one optically active compound. The optically active compound is effective in inducing a helical structure in liquid crystal molecules to give a required twist angle, thereby preventing a reverse twist. Specific preferred examples of the optically active compound include compounds (Op-1) to (Op-18) described below.

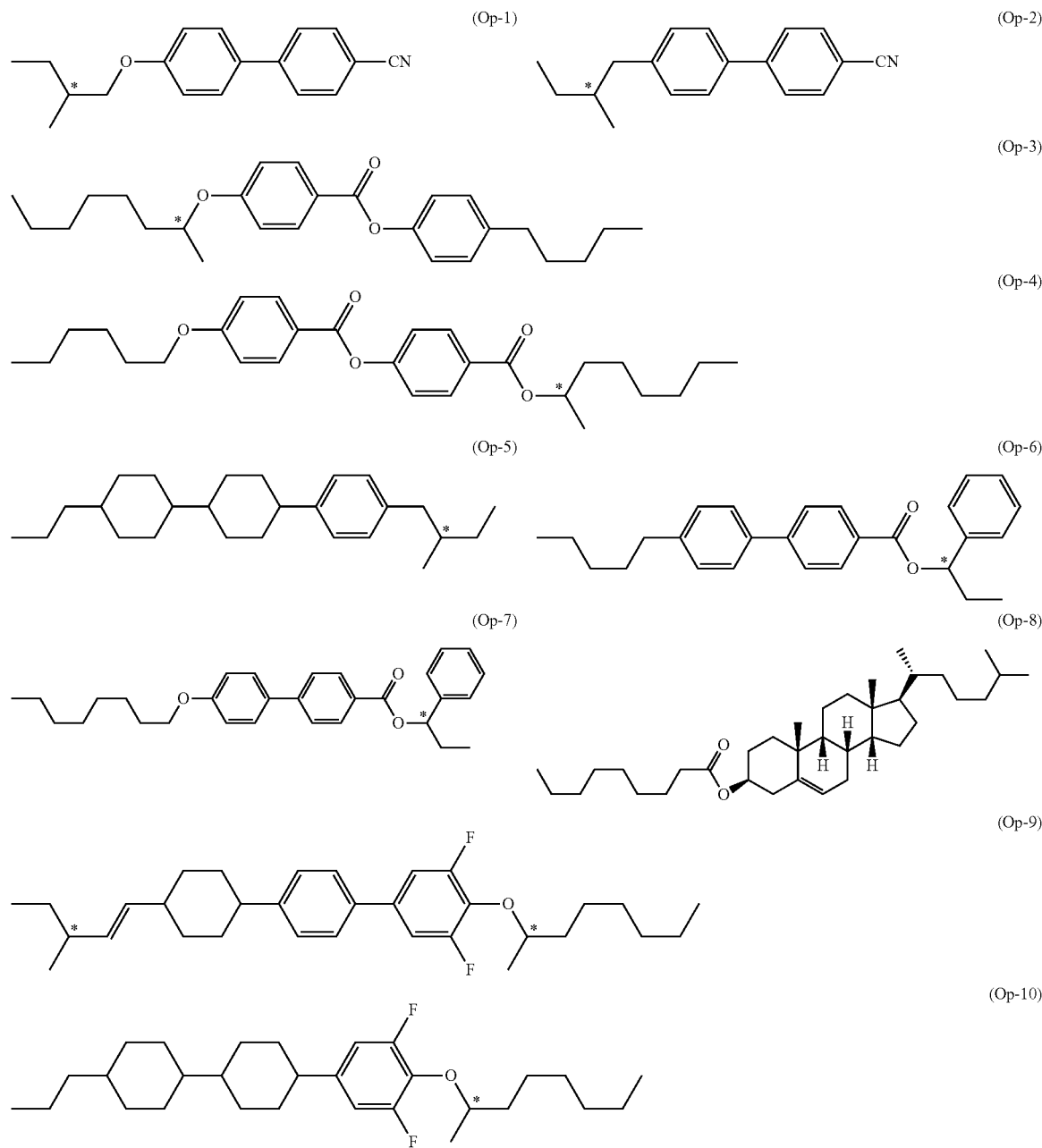

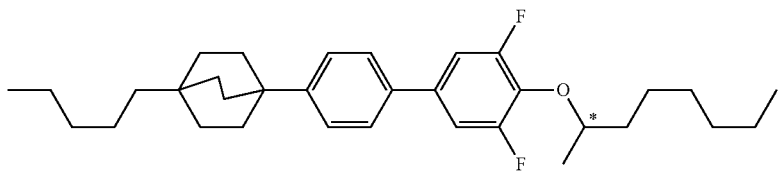
(Op-11)

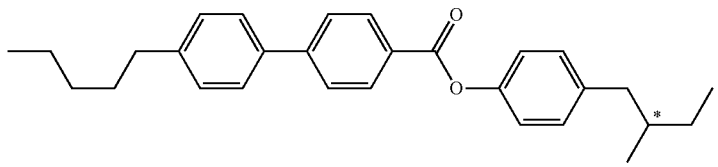
(Op-12)

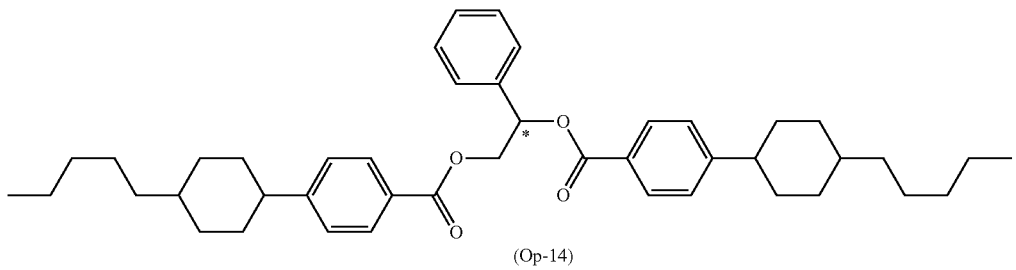
(Op-13)

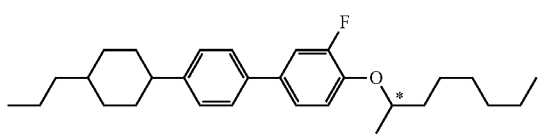
(Op-14)

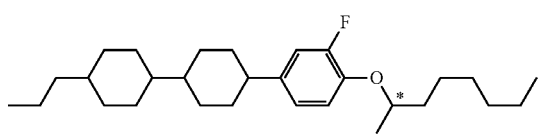
(Op-15)

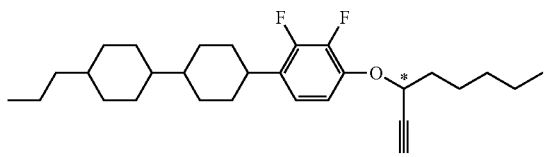
(Op-16)

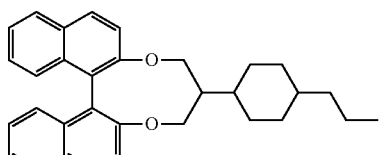
(Op-17)

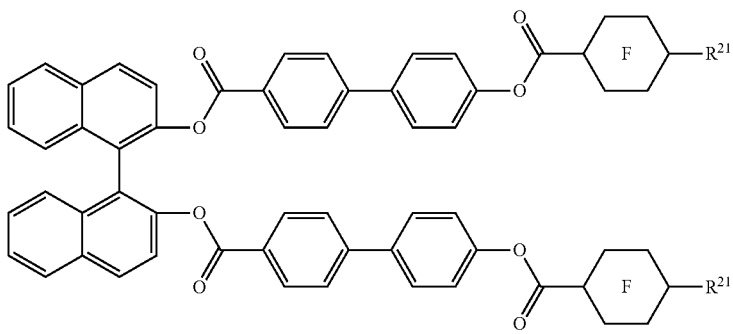
(Op-18)

In compound (Op-18), ring F is 1,4-cyclohexylene or 1,4-phenylene, and $R^{21}$ is alkyl having 1 to 10 carbons.

In the composition, a helical pitch is adjusted by adding such an optically active compound thereto. The helical pitch is preferably adjusted in the range of approximately 40 to approximately 200 micrometers in a composition for the TFT mode or the TN mode. In a composition for the STN mode, the helical pitch is preferably adjusted in the range of approximately 6 to approximately 20 micrometers. In the case of a composition for a BTN mode, the helical pitch is preferably adjusted in the range of approximately 1.5 to approximately 4 micrometers. Two or more optically active compounds may be added thereto for the purpose of adjusting temperature dependence of the helical pitch.

The composition can also be used for the PSA mode by adding the polymerizable compound. Specific examples of the polymerizable compound include an acrylate, a methacrylate, a vinyl compound, a vinyloxy compound, a propenyl ether, an epoxy compound (oxirane, oxetane) and a vinyl ketone. The polymerizable compound is polymerized by irradiation with ultraviolet light or the like. An initiator such as a photopolymerization initiator may be added thereto. Suitable conditions for polymerization, a suitable type of the initiator and a suitable amount thereof are known to those skilled in the art and are described in literature. Specific preferred examples of the polymerizable compound include compounds (M-1) to (M-12).

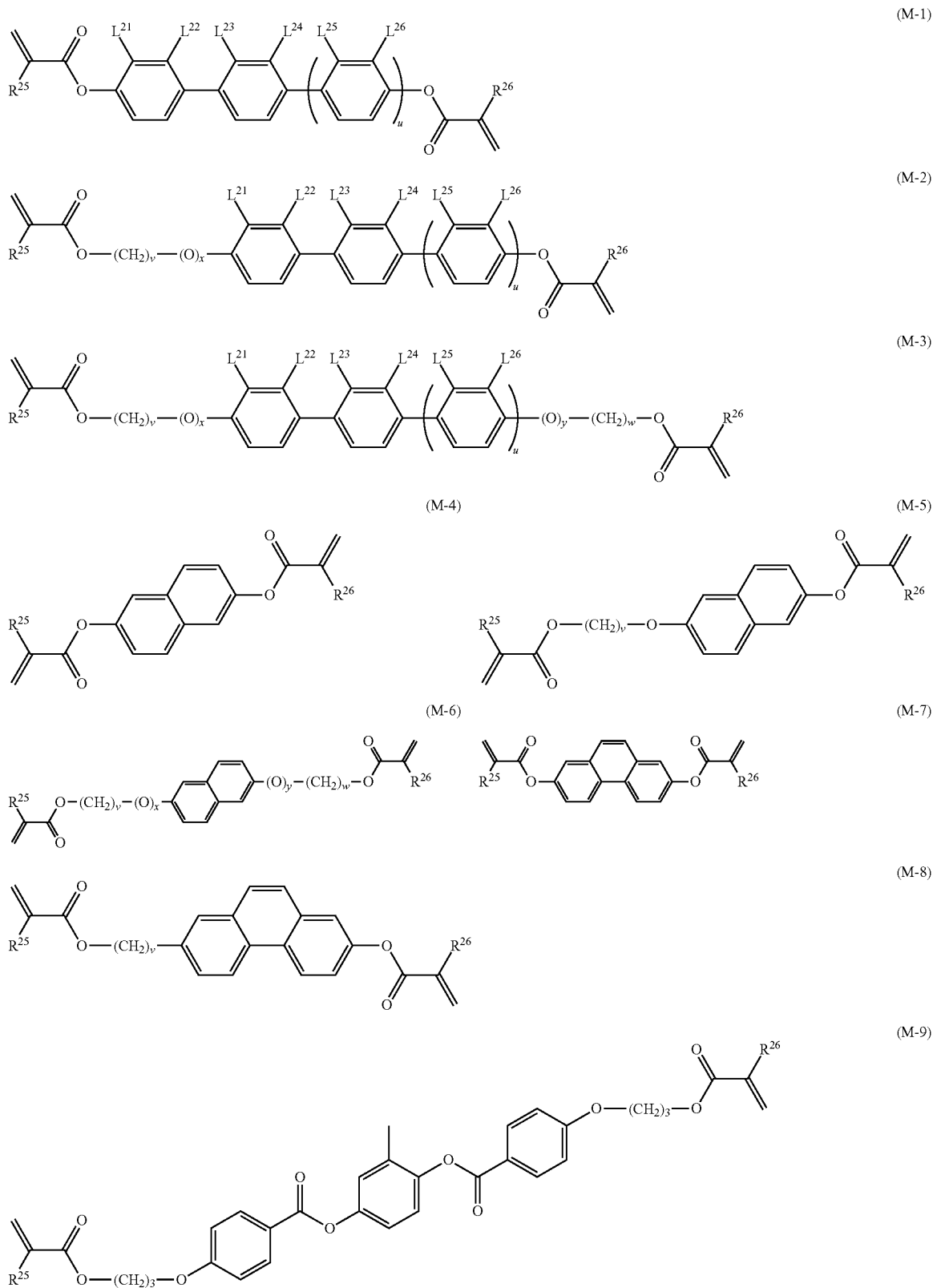

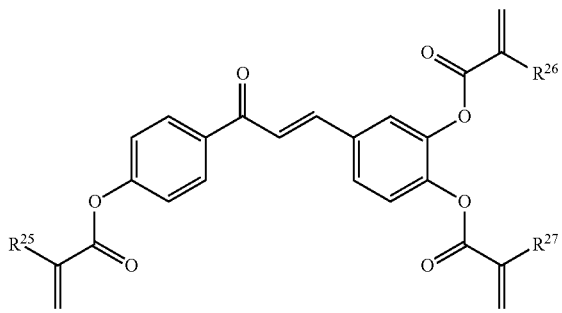

(M-10)

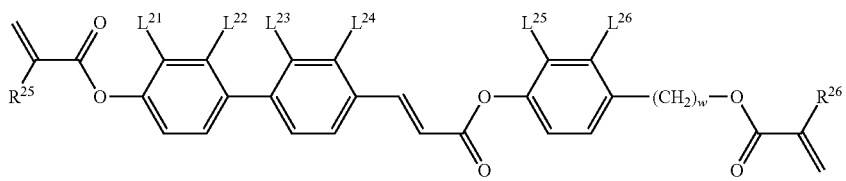

(M-11)

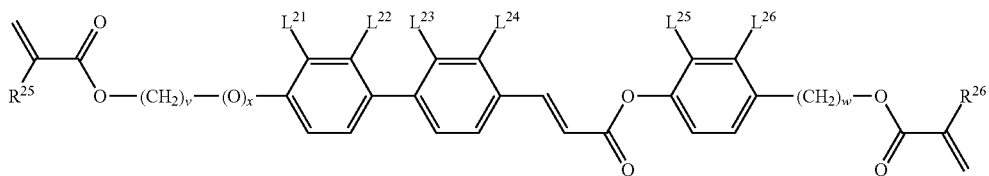

(M-12)

In compounds (M-1) to (M-12), $R^{25}$, $R^{26}$ and $R^{27}$ are independently hydrogen or methyl; u, x and y are independently 0 or 1; v and w are independently an integer from 1 to 10; and $L^{21}$, $L^{22}$, $L^{23}$, $L^{24}$, $L^{25}$ and $L^{26}$ are independently hydrogen or fluorine.

The antioxidant is effective for maintaining the large voltage holding ratio. Specific preferred examples of the antioxidant include compounds (AO-1) and (AO-2) described below, IRGANOX 415, IRGANOX 565, IRGANOX 1010, IRGANOX 1035, IRGANOX 3114 and IRGANOX 1098 (trade names: BASF SE). The ultraviolet light absorber is effective for preventing a decrease of the maximum temperature. Specific preferred examples of the ultraviolet light absorber include a benzophenone derivative, a benzoate derivative and a triazole derivative. Specific examples include (AO-3) and (AO-4) described below, TINUVIN329, TINUVIN P, TINUVIN 326, TINUVIN 234, TINUVIN 213, TINUVIN 400, TINUVIN 328, TINUVIN 99-2 (trade name: BASF SE) and 1,4-diazabicyclo[2.2.2] octane (DABCO). A light stabilizer such as amine having steric hindrance is preferred for maintaining the large voltage holding ratio. Specific preferred examples of the light stabilizer include (AO-5) and (AO-6) described below, TINUVIN 144, TINUVIN 765 and TINUVIN 770DF (trade name: BASF SE). The heat stabilizer is also effective for maintaining the large voltage holding ratio, and preferred examples include IRGAFOS 168 (trade name: BASF SE). The defoaming agent is effective for preventing foam formation. Specific preferred examples of the defoaming agent include dimethyl silicone oil and methylphenyl silicone oil.

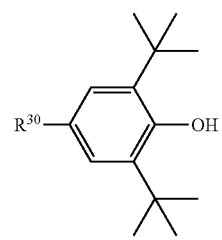

(AO-1)

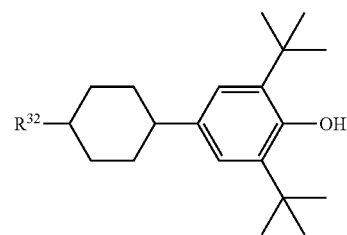

(AO-2)

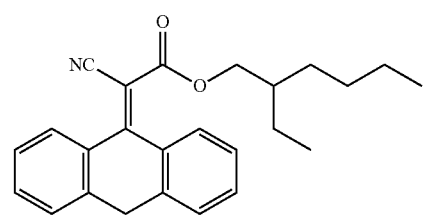

(AO-3)

(AO-4)

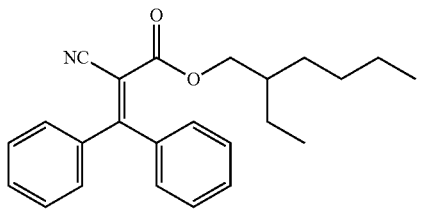

(AO-5)

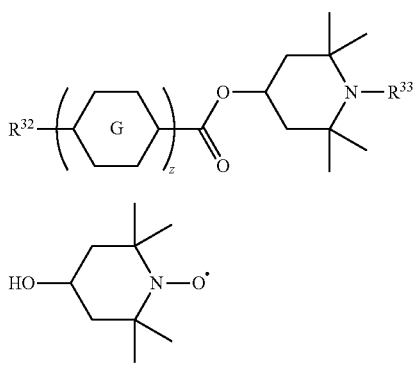

(AO-6)

In compound (AO-1), $R^{30}$ is alkyl having 1 to 20 carbons, alkoxy having 1 to 20 carbons, $-COOR^{31}$ or $-CH_2CH_2COOR^{31}$, and $R^{31}$ is alkyl having 1 to 20 carbons. In compound (AO-2), $R^{32}$ is alkyl having 1 to 20 carbons. In compound (AO-5), $R^{32}$ is alkyl having 1 to 20 carbons; $R^{33}$ is hydrogen, methyl, or O. (oxygen radical); ring G is 1,4-cyclohexylene or 1,4-phenylene; and z is 1, 2 or 3.

The composition can also be used for a liquid crystal composition for a guest host (GH) mode by addition of a dichroic dye such as a merocyanine, stylyl, azo, azomethine, azoxy, quinophthalone, anthraquinone or tetrazine dye thereto.

4. Liquid Crystal Display Device

The composition can be used for a liquid crystal display device having an operating mode such as the PC mode, the TN mode, the STN mode, the OCB mode and the PSA mode and driven by an active matrix (AM) mode. The composition can also be used for a liquid crystal display device having the operating mode such as the PC mode, the TN mode, the STN mode, the OCB mode, the VA mode and the IPS mode and driven by a passive matrix (PM) mode. The AM mode device and the PM mode device can be applied to any of a reflective type, a transmissive type and transflective type.

The composition can also be used for a nematic curvilinear aligned phase (NCAP) device prepared by microencapsulating a nematic liquid crystal, and a polymer dispersed liquid crystal display device (PDLCD) and a polymer network liquid crystal display device (PNLCD), in which a three-dimensional network polymer is formed in the liquid crystal.

It will be apparent to those skilled in the art that various modifications and variations can be made in the invention and specific examples provided herein without departing from the spirit or scope of the invention. Thus, it is intended that the invention covers the modifications and variations of this invention that come within the scope of any claims and their equivalents.

The following examples are for illustrative purposes only and are not intended, nor should they be interpreted to, limit the scope of the invention.

EXAMPLES

The invention will be described in greater detail by way of Examples. However, the invention is not limited by the Examples.

1. Example of Compound (1)

Compound (1) was synthesized by procedures described below. The thus prepared compound was identified by a method such as an NMR analysis. Physical properties of the compound were measured by methods described below.

NMR Analysis

For measurement, DRX-500 made by Bruker BioSpin Corporation was used. In $^1$H-NMR measurement, a sample was dissolved in a deuterated solvent such as $CDCl_3$, and measurement was carried out under conditions of room temperature, 500 MHz and 16 times of accumulation. Tetramethylsilane (TMS) was used as an internal standard. In $^{19}$F-NMR measurement, $CFCl_3$ was used as an internal standard, and measurement was carried out under conditions of 24 times of accumulation. In the explanation of nuclear magnetic resonance spectra, symbols s, d, t, q, quin, sex, m and br stand for a singlet, a doublet, a triplet, a quartet, a quintet, a sextet, a multiplet and being broad, respectively.

Sample for Measurement

When measuring a phase structure and a transition temperature, a liquid crystal compound itself was used as a sample. When characteristics such as a maximum temperature of a nematic phase, viscosity, optical anisotropy and dielectric anisotropy were measured, a composition prepared by mixing the compound with a base liquid crystal was used as the sample.

In a case where a sample prepared by mixing the compound with the base liquid crystal was used, measurement was carried out according to the method described below. The sample was prepared by mixing 15% by weight of the compound and 85% by weight of the base liquid crystal. Then, extrapolated values were calculated from measured values of the sample, according to an extrapolation method represented by an equation below, and the extrapolated values were described. {Extrapolated value}={100×(measured value of a sample)−(% by weight of a base liquid crystal)×(measured value of the base liquid crystal)}/(% by weight of the compound).

When crystals (or a smectic phase) precipitated at 25° C. even at a ratio of the compound to the base liquid crystal, a ratio of the compound to the base liquid crystal was changed in the order of (10% by weight: 90% by weight), (5% by weight: 95% by weight) and (1% by weight: 99% by weight), and physical properties of the sample at the ratio at which no crystals (or the smectic phase) precipitated at 25° C. were measured. In addition, unless otherwise noted, the ratio of the compound to the base liquid crystal was 15% by weight: 85% by weight.

As the base liquid crystal, base liquid crystal (i) described below was used. Ratios of components of base liquid crystal (i) were expressed in terms of weight percent (% by weight).

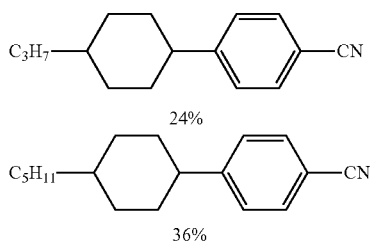

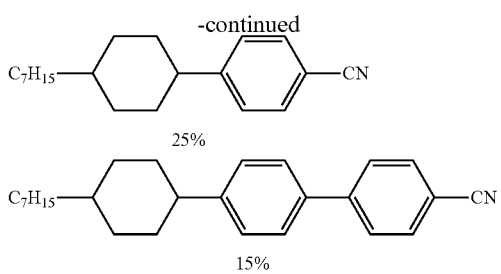

Measuring Methods

Physical properties were measured according to the methods described below. Most of the measuring methods were applied as described in the Standard of the Japan Electronics and Information Technology Industries Association (JEITA EIAJ ED-2521B) discussed and established by JEITA, or modified thereon. No thin film transistor was attached to a TN device used for measurement.

(1) Phase Structure

A sample was placed on a hot plate of a melting point apparatus (FP-52 Hot Stage made by Mettler-Toledo International Inc.) equipped with a polarizing microscope, and a state of phase and a change thereof were observed with the polarizing microscope while the sample was heated at a rate of 3° C. per minute, and a kind of the phase was specified.

(2) Transition Temperature (° C.)

For measurement, a differential scanning calorimeter, Diamond DSC System, made by PerkinElmer, Inc. or a high-sensitivity differential scanning calorimeter, X-DSC7000, made by SII NanoTechnology, Inc. were used. A sample was heated and then cooled at a rate of 3° C. per minute, and a starting point of an endothermic peak or an exothermic peak caused by a phase change of the sample was determined by extrapolation, and thus the transition temperature was determined. Temperature at which a compound undergoes transition from a solid to a liquid crystal phase such as a smectic phase and a nematic phase may be occasionally abbreviated as "minimum temperature of the liquid crystal phase." Temperature at which the compound undergoes transition from the liquid crystal phase to an isotropic liquid may be occasionally abbreviated as "clearing point."

The crystals were expressed as C. When kinds of the crystals were distinguishable, each of the crystals was expressed as $C_1$ or $C_2$. The smectic phase or the nematic phase was expressed as S or N. When smectic A phase, smectic B phase, smectic C phase or smectic F phase was distinguishable among the smectic phases, the phases were expressed as $S_A$, $S_B$, $S_C$ or $S_F$, respectively. A liquid (isotropic) was expressed as 1. The transition temperature was expressed as "C 50.0 N 100.0 I," for example. The expression indicates that the transition temperature from the crystals to the nematic phase was 50.0° C., and the transition temperature from the nematic phase to the liquid was 100.0° C.

(3) Compatibility at a Low Temperature

Samples in which the base liquid crystal and the compound were mixed for the compound to be 20% by weight, 15% by weight, 10% by weight, 5% by weight, 3% by weight and 1% by weight were prepared, and placed in glass vials. After the glass vials were kept in freezers at −10° C. or −20° C. for a predetermined period of time, whether or not crystals (or the smectic phase) precipitated was observed.

(4) Maximum Temperature of the Nematic Phase ($T_{NI}$ or NI; ° C.)

A sample was placed on a hot plate in a melting point apparatus equipped with a polarizing microscope, and heated at a rate of 1° C. per minute. Temperature when part of the sample began to change from the nematic phase to the isotropic liquid was measured. A higher limit of the temperature range of the nematic phase may be occasionally abbreviated as "maximum temperature." When the sample was a mixture of a compound and a base liquid crystal, the maximum temperature was expressed in terms of a symbol $T_{NI}$. When the sample was a mixture of the compound and component (B) or the like, the maximum temperature was expressed in terms of a symbol NI.

(5) Minimum Temperature of the Nematic Phase ($T_c$; ° C.)

Samples each having the nematic phase were kept in freezers at temperatures of 0° C., −10° C., −20° C., −30° C. and −40° C. for 10 days, and then liquid crystal phases were observed. For example, when the sample maintained the nematic phase at −20° C. and changed to the crystals or the smectic phase at −30° C., $T_c$ was expressed as $T_c \leq -20°$ C. A lower limit of the temperature range of the nematic phase may be occasionally abbreviated as "minimum temperature."

(6) Viscosity (Bulk Viscosity; η; Measured at 20° C.; mPa·s)

A cone-plate (E type) rotational viscometer made by Tokyo Keiki, Inc. was used for measurement.

(7) Viscosity (Rotational Viscosity; γ1; Measured at 25° C.; mPa·s)

Measurement was carried out according to the method described in M. Imai et al., Molecular Crystals and Liquid Crystals, Vol. 259, p. 37 (1995). A sample was put in a TN device in which a twist angle was 0 degrees and a distance (cell gap) between two glass substrates was 5 micrometers. Voltage was applied stepwise to the device in the range of 16 V to 19.5 V at an increment of 0.5 V. After a period of 0.2 second with no voltage application, voltage was repeatedly applied under conditions of only one rectangular wave (rectangular pulse; 0.2 second) and no voltage application (2 seconds). A peak current and a peak time of a transient current generated by the applied voltage were measured. A value of rotational viscosity was obtained from the measured values and calculation equation (8) described on page 40 of the paper presented by M. Imai et al. A value of dielectric anisotropy required for the calculation was determined using the device by which the rotational viscosity was measured and by the method described below.

(8) Optical Anisotropy (Refractive Index Anisotropy; an; Measured at 25° C.)

Measurement was carried out by an Abbe refractometer with a polarizing plate mounted on an ocular, using light at a wavelength of 589 nanometers. A surface of a main prism was rubbed in one direction, and then a sample was added dropwise onto the main prism. A refractive index (n∥) was measured when the direction of polarized light was parallel to the direction of rubbing. A refractive index (n⊥) was measured when the direction of polarized light was perpendicular to the direction of rubbing. A value of optical anisotropy was calculated from an equation: Δn=n∥−n⊥.

(9) Dielectric Constant (∈⊥) in a Minor Axis Direction and Dielectric Anisotropy (Δ∈; Measured at 25° C.)

A sample was put in a TN device in which a distance (cell gap) between two glass substrates was 9 micrometers and a twist angle was 80 degrees. Sine waves (10 V, 1 kHz) were applied to the device, and after 2 seconds, a dielectric constant (∈∥) in the major axis direction of liquid crystal molecules was measured. Sine waves (0.5 V, 1 kHz) were applied to the device, and after 2 seconds, a dielectric constant ($\in\perp$) in the minor axis direction of the liquid crystal molecules was measured. A value of dielectric anisotropy was calculated from an equation: $\Delta\in = \in\|  - \in\perp$.

(10) Elastic Constant (K; Measured at 25° C.; pN)

HP4284A LCR Meter made by Yokogawa-Hewlett-Packard Co. was used for measurement. A sample was put in a horizontal alignment device in which a distance (cell gap) between two glass substrates was 20 micrometers. An electric charge of 0 V to 20 V was applied to the device, and electrostatic capacity and applied voltage were measured. Measured values of electrostatic capacity (C) and applied voltage (V) were fitted to equation (2.98) and equation (2.101) on page 75 of "Liquid Crystal Device Handbook" (Ekisho Debaisu Handobukku in Japanese; The Nikkan Kogyo Shimbun, Ltd.) and values of $K_{11}$ and $K_{33}$ were obtained from equation (2.99). Next, $K_{22}$ was calculated using the previously determined values of $K_{11}$ and $K_{33}$ in formula (3.18) on page 171. Elastic constant K was expressed in terms of a mean value of the thus determined $K_{11}$, $K_{22}$ and $K_{33}$.

(11) Threshold Voltage (Vth; Measured at 25° C.; V)

An LCD-5100 luminance meter made by Otsuka Electronics Co., Ltd. was used for measurement. A light source was a halogen lamp. A sample was put in a normally white mode TN device in which a distance (cell gap) between two glass substrates was approximately 0.45/Δn (μm) and a twist angle was 80 degrees. A voltage (32 Hz, rectangular waves) to be applied to the device was stepwise increased from 0 V to 10 V at an increment of 0.02 V. On the occasion, the device was irradiated with light from a direction perpendicular to the device, and an amount of light transmitted through the device was measured. A voltage-transmittance curve was prepared, in which the maximum amount of light corresponds to 100% transmittance and the minimum amount of light corresponds to 0% transmittance. A threshold voltage was expressed in terms of a voltage at 90% transmittance.

(12) Voltage Holding Ratio (VHR-1; Measured at 25° C.; %)

A TN device used for measurement had a polyimide alignment film, and a distance (cell gap) between two glass substrates was 5 micrometers. A sample was put in the device, and the device was sealed with an ultraviolet-curable adhesive. The device was charged by applying a pulse voltage (60 microseconds at 5 V) at 25° C. A decaying voltage was measured for 16.7 milliseconds with a high-speed voltmeter, and area A between a voltage curve and a horizontal axis in a unit cycle was determined. Area B was an area without decay. A voltage holding ratio was expressed in terms of a percentage of area A to area B.

(13) Voltage Holding Ratio (VHR-2; Measured at 80° C.; %)

A voltage holding ratio (VHR-2) was determined in a manner similar to the method for measuring VHF-1 except that measurement was carried out at 80° C.

Raw Material

Solmix A-11 (trade name) is a mixture of ethanol (85.5%), methanol (13.4%) and isopropanol (1.1%), and was purchased from Japan Alcohol Trading Co., Ltd.

Example 1

Synthesis of Compound (No. 38)

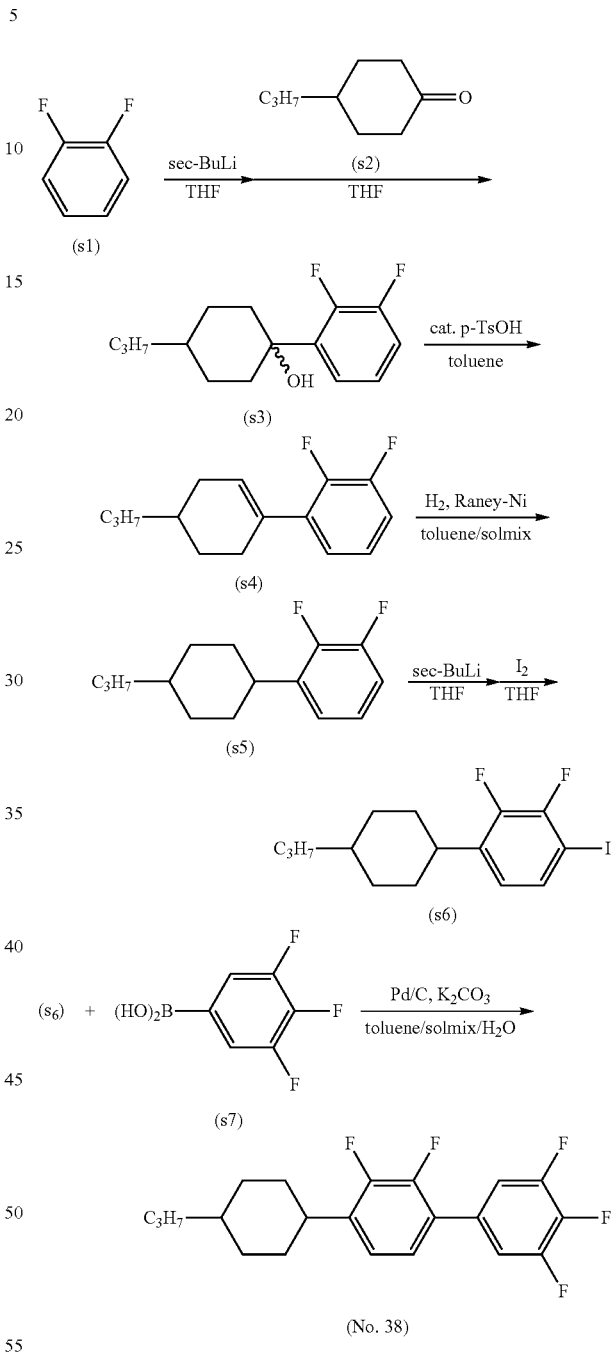

First Step

In a reaction vessel under a nitrogen atmosphere, 100 g of 1,2-difluorobenzene (s1) and 1,000 mL of THF were put and the resulting mixture was cooled to −74° C. Thereto, 876.5 mL of 1.57 M N-butyllithium n-hexane solution was added dropwise in the temperature range of −74° C. to −70° C., and the resulting mixture was further stirred for 2 hours. Subsequently, 300 mL of THF solution of 177.0 g of 4-propylcyclohexanone (s2) was added dropwise thereto in the temperature range of −74° C. to −65° C., and the resulting mixture was further stirred for 8 hours while returning to 25°

C. The resulting reaction mixture was added to a vessel in which 500 mL of 1 N HCl aqueous solution and 800 mL of ethyl acetate were put and mixed, and then left to stand to be separated into an organic layer and an aqueous layer, and extraction operation was performed to the organic layer. The resulting organic layer was fractionated and washed with water, sodium hydrogencarbonate and water, and dried over anhydrous magnesium sulfate. Then, a solvent was distilled off under reduced pressure to obtain 215.1 g of compound (S3). The resulting compound (s3) was a yellow liquid matter.

Second Step

Then, 215.1 g of compound (s3), 6.5 g of p-toluenesulfonic acid and 300 mL of toluene were mixed, and the resulting mixture was refluxed under heating for 2 hours while draining distilled-off water. The resulting reaction mixture was cooled to 30° C., 500 mL of water and 800 mL of toluene were added to the resulting liquid and mixed, and then left to stand to be separated into two layers of an organic layer and an aqueous layer, and extraction operation was performed to the organic layer. The resulting organic layer was fractionated and washed with a saturated aqueous solution of sodium hydrogencarbonate and water, and dried over anhydrous magnesium sulfate. The resulting solution was purified by fractionation operation by column chromatography using heptane as an eluent and a silica gel as a packing material and dried to obtain 186.6 g of compound (s4). A yield from compound (s2) was 81.0%.

Third Step

Into a mixed solvent of 150 mL of toluene and 150 mL of Solmix A-11, 50 g of compound (s4) was dissolved, and 5.0 g of Raney nickel was further added thereto, and the resulting mixture was stirred under a hydrogen atmosphere at room temperature until no hydrogen was absorbed. After reaction completion, Raney nickel was removed and the solvent was distilled off, and the resulting residue was purified by fractionation operation by column chromatography using a mixed solvent of heptane and toluene (heptane:toluene=2:3 in a volume ratio) as an eluent and a silica gel as a packing material, and the resulting residue was further purified by recrystallization from a mixed solvent of ethyl acetate and Solmix A-11 (ethyl acetate:Solmix=1:2 in a volume ratio) and dried to obtain 49.5 g of compound (s5). A yield from compound (s4) was 98.9%.

Fourth Step

In a reaction vessel under a nitrogen atmosphere, 10.0 g of compound (s5) and 100 mL of THF were put, and the resulting mixture was cooled to −74° C. Thereto, 43.3 mL of 1.00 M sec-butyl lithium, n-hexane and cyclohexane solution was added dropwise in the temperature range of −74° C. to −70° C., and the resulting mixture was further stirred for 2 hours. Subsequently, 100 mL of THF solution of 12.0 g of iodine was added dropwise thereto in the temperature range of −75° C. to −70° C., and the resulting mixture was stirred for 8 hours while returning to 25° C. The resulting reaction mixture was poured into 500 mL of aqueous sodium thiosulfate solution, and the resulting mixture was mixed. Then, 500 mL of toluene was added thereto to be separated into an organic layer and an aqueous layer, and extraction operation was performed. The resulting organic layer was fractionated and subsequently washed with brine and dried over anhydrous magnesium sulfate. The resulting solution was concentrated under reduced pressure, and the resulting residue was purified by fractionation operation by column chromatography using heptane as an eluent and a silica gel as a packing material. A solvent was distilled off and the resulting residue was dried to obtain 13.6 g of compound (s6). A yield from compound (s5) was 92.1%.

Fifth Step

In a reaction vessel under a nitrogen atmosphere, 6.0 g of compound (s6), 5.2 g of dihydroxyborane derivative (s7), 10.6 g of potassium carbonate, 0.06 g of Pd/C (NX type), 100 mL of toluene, 100 mL of Solmix A-11 and 100 mL of water were put, and the resulting mixture was refluxed under heating for 2 hours. The resulting reaction mixture was cooled to 25° C., and then poured into 300 mL of water and 300 mL of toluene and mixed. Then, the resulting mixture was left to stand to be separated into two layers of an organic layer and an aqueous layer, and extraction operation was performed to the organic layer. The resulting organic layer was fractionated and washed with water, dried over anhydrous magnesium sulfate. The resulting solution was concentrated under reduced pressure, and the resulting residue was purified by fractionation operation by column chromatography using a mixed solution of toluene and heptane (toluene:heptane=1:1 in a volume ratio) as an eluent and a silica gel as a packing material. The resulting residue was further purified by recrystallization form a mixed solution of ethyl acetate/Solmix A-11 (ethyl acetate: Solmix A-11=2:1 in a volume ratio) and dried to obtain 6.0 g of compound (No. 38). A yield from compound (s6) was 78.1%.

Chemical shift δ (ppm; CDCl$_3$): 7.16 (d, 2H), 7.05 (s, 2H), 2.87 (t, 1H), 1.88 (d, 4H), 1.51 (m, 2H), 1.35 (m, 3H), 1.23 (m, 2H), 1.10 (m, 2H), 0.91 (t, 3H).

Physical properties of compound (No. 38) were as described below.

Transition temperature: C 33.4 I.

Maximum temperature $(T_{NI})$=19.7° C.; optical anisotropy (Δn)=0.104; dielectric anisotropy (Δ∈)=15.4; dielectric constant (∈⊥) in a minor axis direction=8.4; viscosity (η)=51.7 mPa·s.

Example 2

Various kinds of compounds were synthesized using corresponding starting materials by the method described in Example 1, and the resulting products were confirmed to be a an objective compound.

Compound (No. 40)

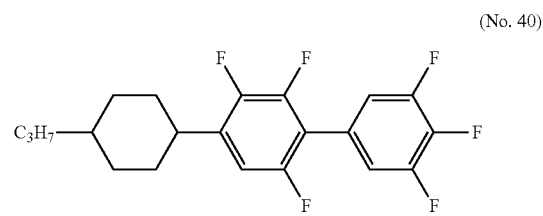

(No. 40)

$^1$H-NMR (δ ppm; CDCl$_3$): 7.11 (t, 2H), 6.84 (ddd, 1H), 2.88 (tt, 1H), 1.89 (m, 4H), 1.52-1.27 (m, 5H), 1.23 (m, 2H), 1.09 (m, 2H), and 0.91 (t, 3H).

Physical properties of compound (No. 40) were as described below.

Transition temperature: C 55.7 I.

Maximum temperature $(T_{NI})$=7.7° C.; optical anisotropy (Δn)=0.097; dielectric anisotropy (Δ∈)=21.1; dielectric constant (∈⊥) in a minor axis direction=7.4; viscosity (η)=70.9 mPa·s.

Compound (No. 7)

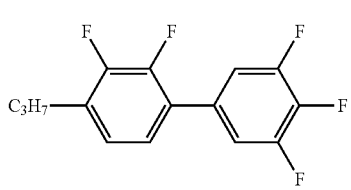

Physical properties of compound (No. 7) were as described below.
Transition temperature: C −17.3 I.
Maximum temperature ($T_{NI}$)=−132.3° C.; optical anisotropy (Δn)=−0.023; dielectric anisotropy (Δ∈)=10.77; dielectric constant (∈⊥) in a minor axis direction=15.73; viscosity (η)=22.9 mPa·s.
$^1$H-NMR (δ ppm; CDCl$_3$): 7.16 (t, 2H), 7.03 (m, 2H), 2.67 (t, 2H), 1.67 (sext, 2H), 0.98 (t, 3H).

Compound (No. 74)

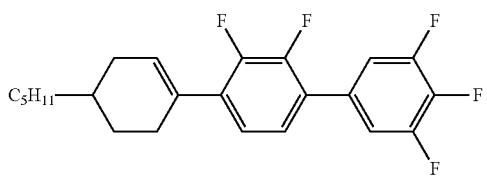

Physical properties of compound (No. 74) were as described below.
Transition temperature: C 59.7 I.
Maximum temperature ($T_{NI}$)=37.0° C.; optical anisotropy (Δn)=0.130; dielectric anisotropy (Δ∈)=12.77; dielectric constant in a minor axis direction (∈⊥)=7.83; viscosity (η)=54.7 mPa·s.
$^1$H-NMR (δ ppm; CDCl$_3$): 7.18 (t, 2H), 7.06 (m, 2H), 6.03 (m, 1H), 2.47 (m, 1H), 2.36 (m, 2H), 1.87 (m, 2H), 1.62 (m, 1H), 1.33 (m, 9H), 0.91 (t, 3H).

Compound (No. 86)

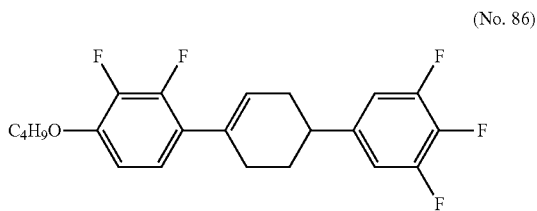

Physical properties of compound (No. 86) were as described below.
Transition temperature: C 56.4 I.
Maximum temperature ($T_{NI}$)=10.4° C.; optical anisotropy (Δn)=0.097; dielectric anisotropy (Δ∈)=10.10; dielectric constant in a minor axis direction (∈⊥)=11.83; viscosity (η)=72.7 mPa·s.
$^1$H-NMR (δ ppm; CDCl$_3$): 6.88 (m, 3H), 6.68 (t, 1H), 5.97 (m, 1H), 4.05 (t, 2H), 2.84 (m, 1H), 2.55 (m, 1H), 2.45 (m, 2H), 2.24 (m, 1H), 2.03 (m, 1H), 1.80 (m, 3H), 1.50 (m, 2H), 0.98 (t, 3H).

Compound (No. 87)

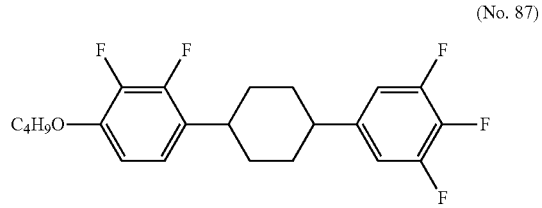

Physical properties of compound (No. 87) were as described below.
Transition temperature: C 65.7 I.
Maximum temperature ($T_{NI}$)=1.0° C.; optical anisotropy (Δn)=0.070; dielectric anisotropy (Δ∈)=8.57; dielectric constant in a minor axis direction (∈⊥)=12.40; viscosity (η)=76.0 mPa·s.
$^1$H-NMR (δ ppm; CDCl$_3$): 6.84 (m, 3H), 6.69 (t, 1H), 4.02 (t, 2H), 2.85 (t, 1H), 2.54 (t, 1H), 1.99 (d, 4H), 1.79 (quin, 2H), 1.67-1.45 (m, 7H), 0.98 (t, 3H).

Compound (No. 71)

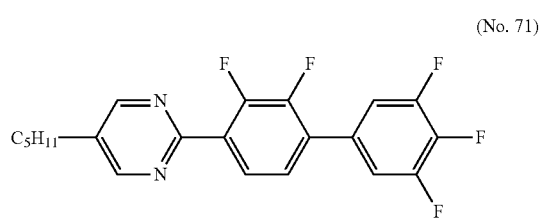

Physical properties of compound (No. 71) were as described below.
Transition temperature: C 84.5 I.
Maximum temperature ($T_{NI}$)=43.7° C.; optical anisotropy (Δn)=0.164; dielectric anisotropy (Δ∈)=26.57; dielectric constant in a minor axis direction (∈⊥)=9.07; viscosity (η)=85.4 mPa·s.
$^1$H-NMR (δ ppm; CDCl$_3$): 8.72 (s, 2H), 7.93 (t, 1H), 7.26 (m, 3H), 2.67 (t, 1H), 1.69 (m, 2H), 1.38 (m, 4H), 0.93 (t, 3H).

Compound (No. 70)

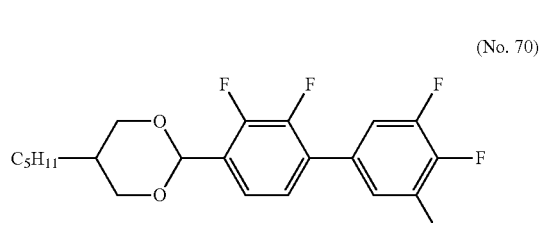

Physical properties of compound (No. 70) were as described below.
Transition temperature: C 35.4 I.
Maximum temperature ($T_{NI}$)=29.0° C.; optical anisotropy (Δn)=0.104; dielectric anisotropy (Δ∈)=21.4; dielectric constant in a minor axis direction (∈⊥)=8.4; viscosity (η)=80.1 mPa·s.
$^1$H-NMR (δ ppm; CDCl$_3$): 7.46 (t, 1H), 7.16 (m, 3H), 5.73 (m, 1H), 4.24 (dd, 2H), 3.58 (t, 2H), 2.16 (m, 1H), 1.29 (m, 6H), 1.11 (m, 2H), 0.90 (t, 3H).

Example 3

Compounds (No. 1) to (No. 140) shown below can be prepared in a manner similar to the synthetic method described in Example 1 by taking as an example the synthetic compound described in Example 2. Attached data were determined by the methods describe above. When measuring a transition temperature, a compound itself was used as a sample. When measuring a maximum temperature ($T_{NI}$), optical anisotropy ($\Delta n$) and dielectric anisotropy ($\Delta\epsilon$), a mixture of a compound (15% by weight) and base liquid crystal (i) (85% by weight) was used as a sample. Then, extrapolated values were calculated from measured values thereof, according to the extrapolation method described above, and described. In addition, in compound (No. 40), a sample for measurement was prepared from 10% by weight of compound (No. 40) and 90% by weight of base liquid crystal (i) because crystals precipitated at an ordinary ratio (15% by weight:85% by weight).

| No. | |
|---|---|
| 1 | (structure) |
| 2 | (structure) |
| 3 | (structure) |
| 4 | (structure) |
| 5 | (structure) |
| 6 | (structure) |
| 7 | (structure) C –17.3 I; $T_{NI}$; –132.3° C., $\Delta$ n; –0.023, $\Delta$ ∈; 10.77, ∈ ⊥; 15.73, η; 22.9 |
| 8 | (structure) |

-continued
| No. | |
|---|---|
| 9 | 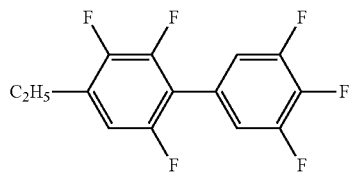 [SMILES: CCc1cc(F)c(-c2cc(F)c(F)c(F)c2)c(F)c1F] |
| 10 | 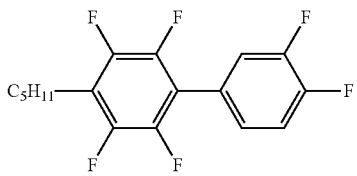 |
| 11 | 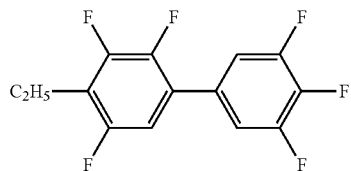 [SMILES: CCc1c(F)cc(-c2cc(F)c(F)c(F)c2)c(F)c1F] |
| 12 | 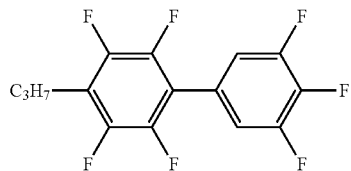 |
| 13 | 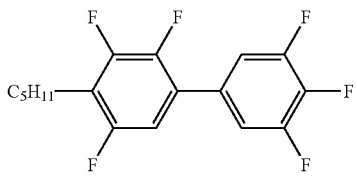 |
| 14 | 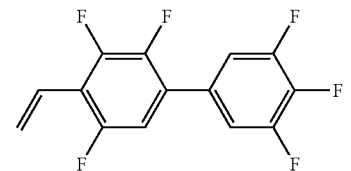 [SMILES: C=Cc1c(F)cc(-c2cc(F)c(F)c(F)c2)c(F)c1F] |
| 15 | 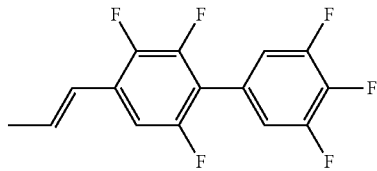 [SMILES: C/C=C/c1cc(F)c(-c2cc(F)c(F)c(F)c2)c(F)c1F] |
| 16 | 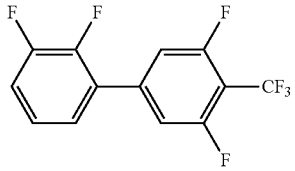 |

| No. | |
|---|---|
| 17 | 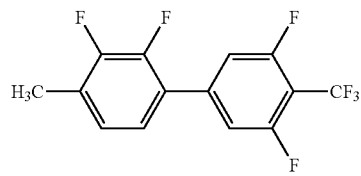 [SMILES: Cc1ccc(-c2cc(F)c(C(F)(F)F)c(F)c2)c(F)c1F] |
| 18 | 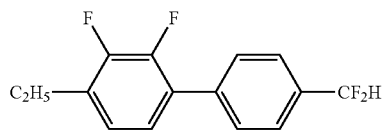 |
| 19 | 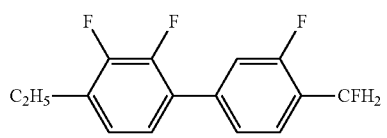 |
| 20 | 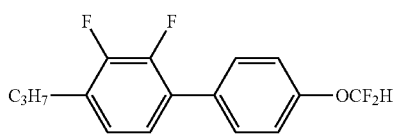 |
| 21 | 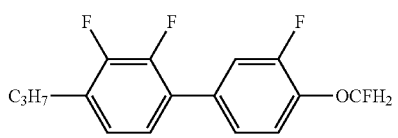 |
| 22 | 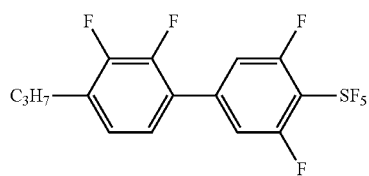 |
| 23 | 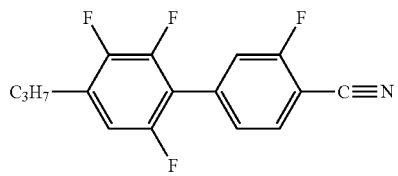 |
| 24 | 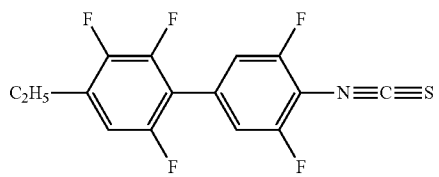 |
| 25 | 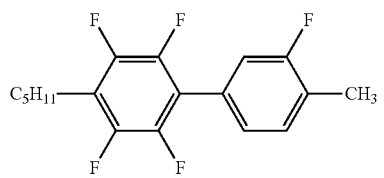 |

-continued
| No. | |
|---|---|
| 26 | 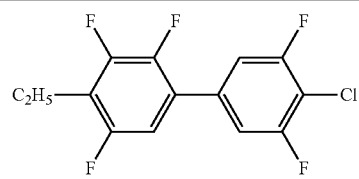 |
| 27 | 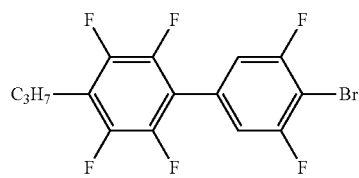 |
| 28 | 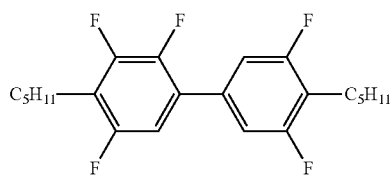 |
| 29 | 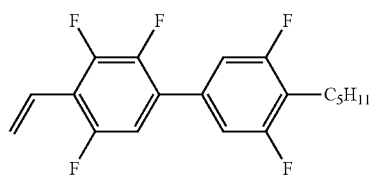 |
| 30 | 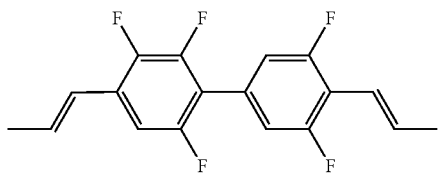 [SMILES: C/C=C/c1cc(F)c(-c2cc(F)c(/C=C/C)c(F)c2)c(F)c1F] |
| 31 | 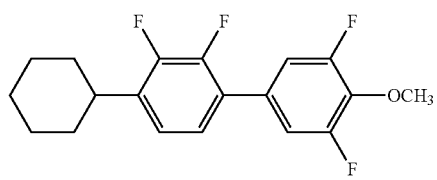 |
| 32 | 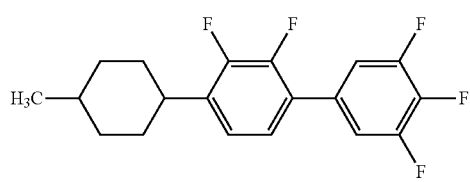 |
| 33 | 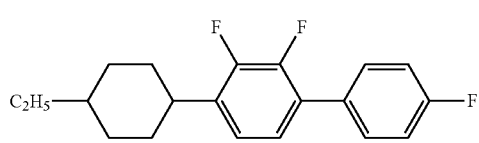 |
| 34 | 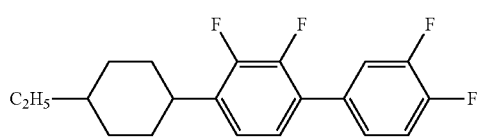 |

| No. | |
|---|---|
| 35 | 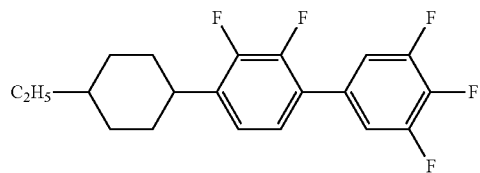 |
| 36 | 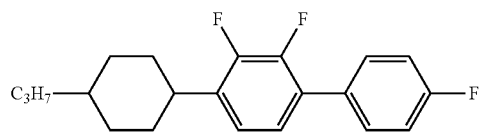 |
| 37 | 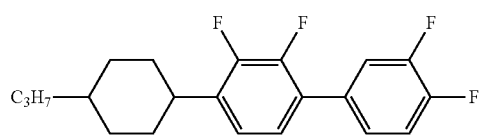 |
| 38 | 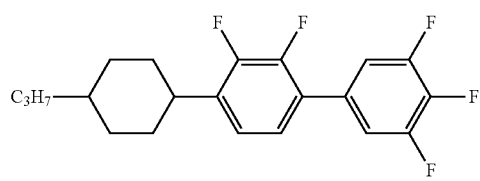<br>C 33.4 I<br>$T_{NI}$; −19.7° C., Δ n; 0.1037,<br>Δ ε; 15.43, ε ⊥; 8.4, η; 51.7 |
| 39 | 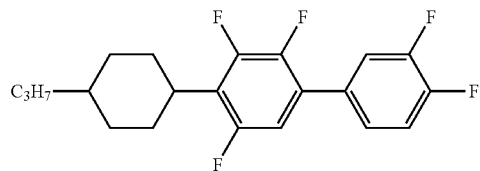 |
| 40 | 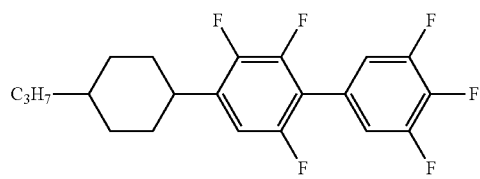<br>C 95.2 I<br>$T_{NI}$; 7.7° C., Δ n; 0.097,<br>Δ ε; 21.1, ε ⊥; 7.4, η; 70.9 |
| 41 | 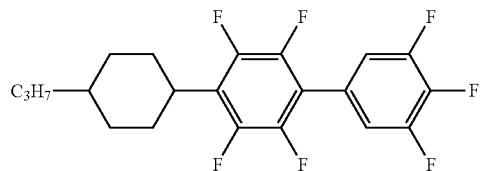 |
| 42 | 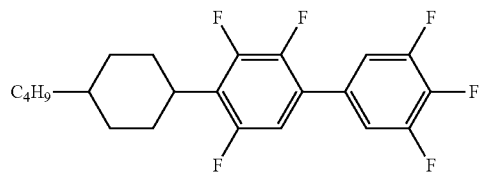 |

-continued
| No. |
|---|
| 43 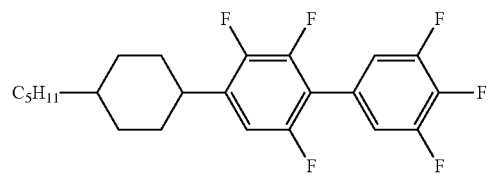 |
| 44 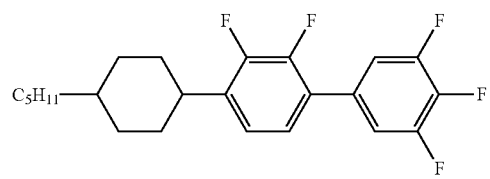 |
| 45 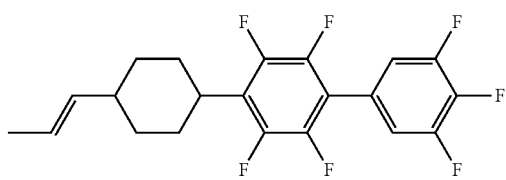 [SMILES: C/C=C/C1CCC(c2c(F)c(F)c(-c3cc(F)c(F)c(F)c3)c(F)c2F)CC1] |
| 46 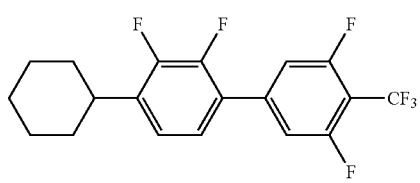 [SMILES: Fc1cc(-c2ccc(C3CCCCC3)c(F)c2F)cc(F)c1C(F)(F)F] |
| 47 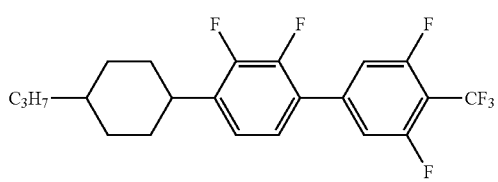 |
| 48 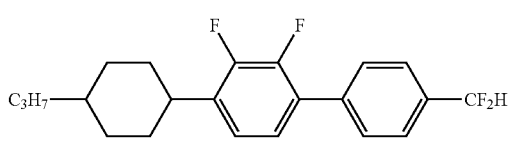 |
| 49 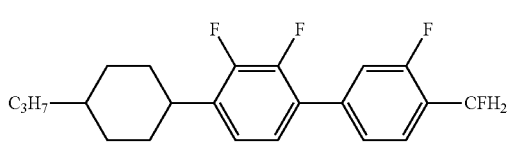 |
| 50 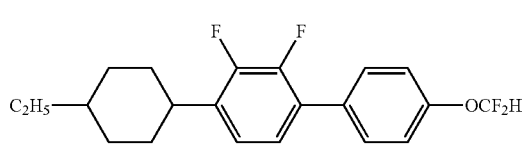 |
| 51 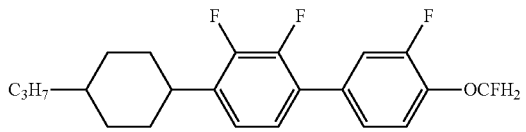 |

-continued
| No. | |
|---|---|
| 52 | 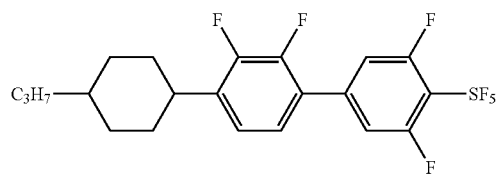 |
| 53 | 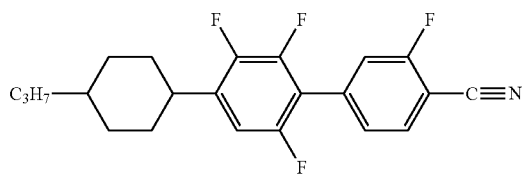 |
| 54 | 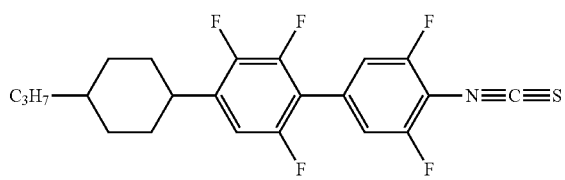 |
| 55 | 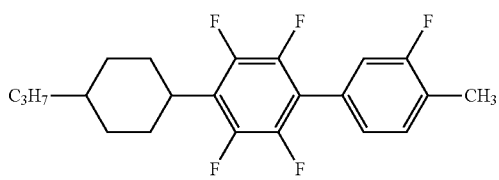 |
| 56 | 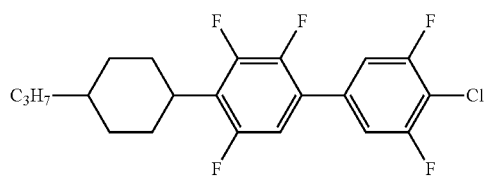 |
| 57 | 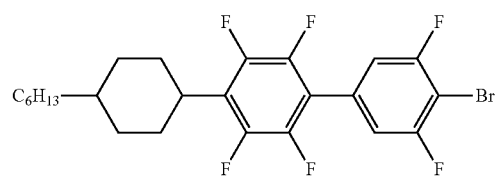 |
| 58 | 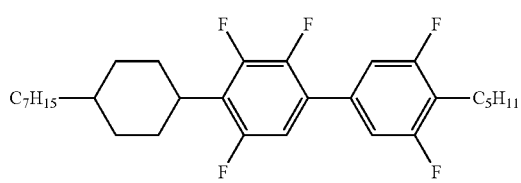 |
| 59 | 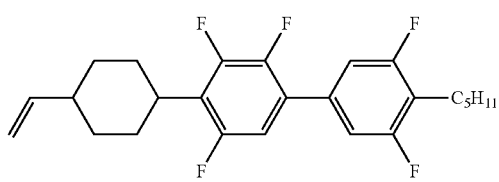 |

-continued
| No. |
|---|
| 60 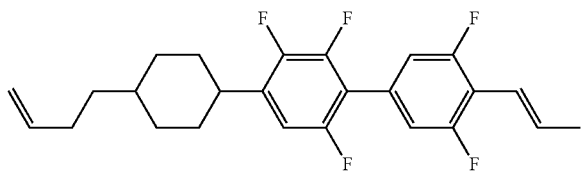 [SMILES: C=CCCC1CCC(c2cc(F)c(-c3cc(F)c(/C=C/C)c(F)c3)c(F)c2F)CC1] |
| 61 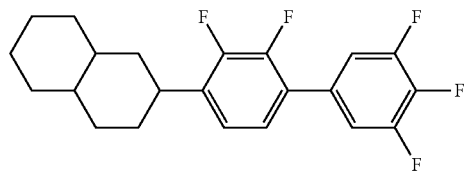 [SMILES: Fc1cc(-c2ccc(C3CCC4CCCCC4C3)c(F)c2F)cc(F)c1F] |
| 62 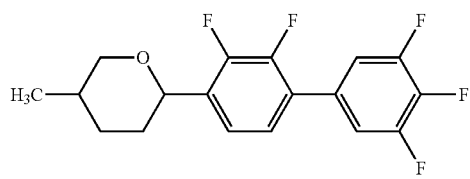 |
| 63 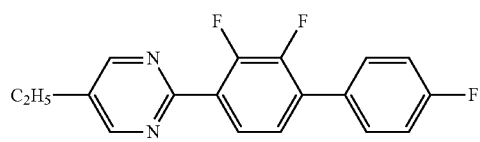 [SMILES: CCc1cnc(-c2ccc(-c3ccc(F)cc3)c(F)c2F)nc1] |
| 64 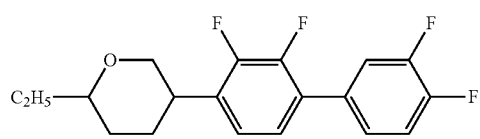 [SMILES: CCC1CCC(c2ccc(-c3ccc(F)c(F)c3)c(F)c2F)CO1] |
| 65 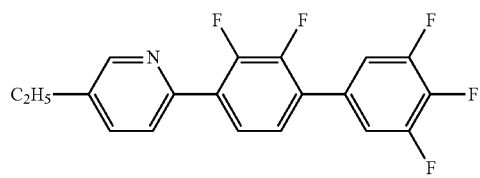 |
| 66 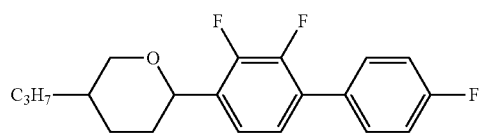 |
| 67 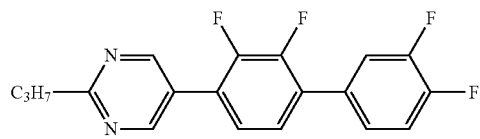 |
| 68 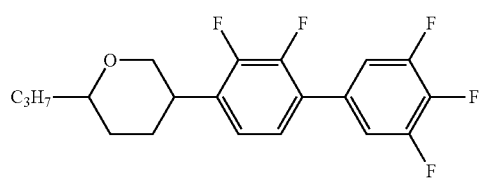 |

-continued

| No. | |
|---|---|
| 69 | C₃H₇–[pyridine]–[difluorophenyl]–[trifluorophenyl] |
| 70 | C₅H₁₁–[dioxane]–[difluorophenyl]–[trifluorophenyl]

C 35.4 I
$T_{NI}$; 29.. 0° C., Δ n; 0.104,
Δ ε; 21.4, ε ⊥; 8.4, η; 80.1 |
| 71 | C₅H₁₁–[pyrimidine]–[difluorophenyl]–[trifluorophenyl]

C 84.5 (S$_A$ 75.3 N 78.1) I
$T_{NI}$; 43.7° C., Δ n; 0.164,
Δ ε; 26.57, ε ⊥; 9.07, η; 85.4 |
| 72 | C₄H₉–[bicyclic dioxolane]–[trifluorophenyl]–[trifluorophenyl] |
| 73 | C₅H₁₁–[phenyl]–[difluorophenyl]–[trifluorophenyl] |
| 74 | C₅H₁₁–[pyridine]–[difluorophenyl]–[trifluorophenyl]

C 59.7 I
$T_{NI}$; 37.0° C., Δ n; 0.130,
Δ ε; 12.77, ε ⊥; 7.8, η; 54.7 |
| 75 | C₃H₇–[cyclohexenyl]–[difluorophenyl]–[trifluorophenyl] |

-continued
| No. | |
|---|---|
| 76 | 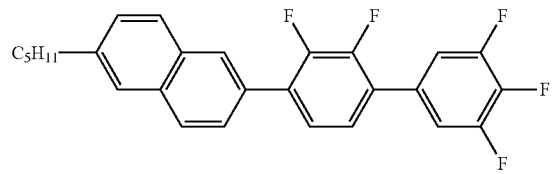 |
| 77 | 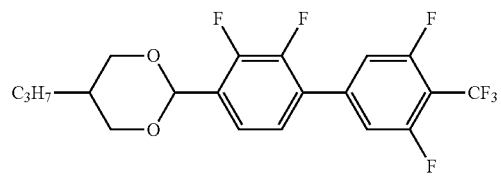 |
| 78 | 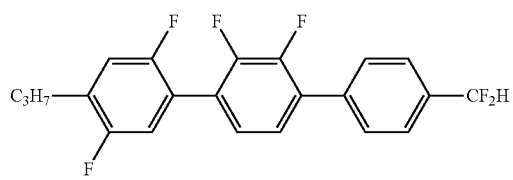 |
| 79 | 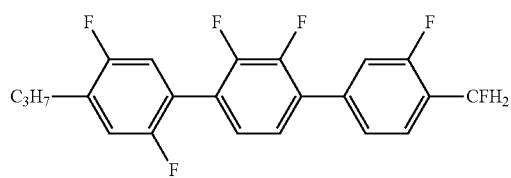 |
| 80 | 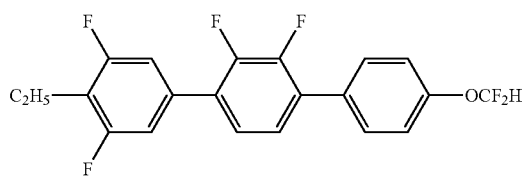 |
| 81 | 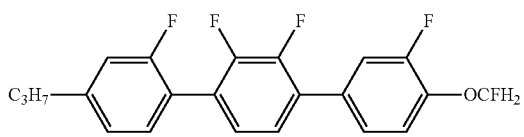 |
| 82 | 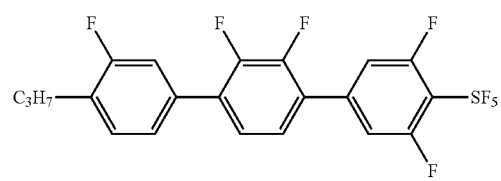 |
| 83 | 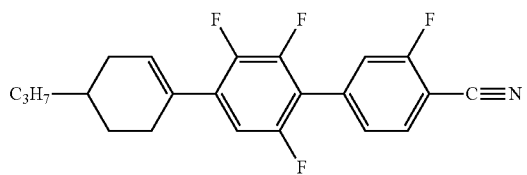 |
| 84 | 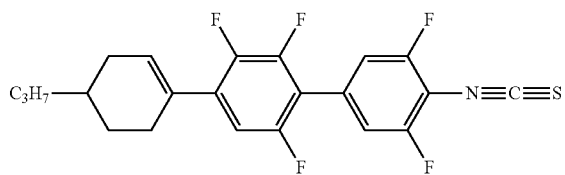 |

-continued
| No. | |
|---|---|
| 85 | 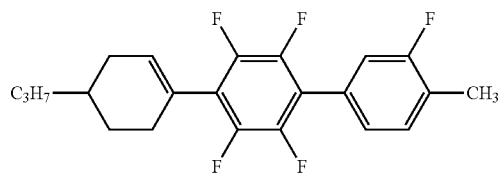 |
| 86 | 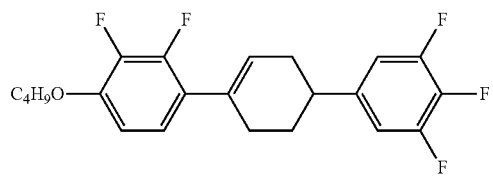
C 56.4 I
$T_{NI}$; 10.4° C., Δ n; 0.097,
Δ ε; 10.1, ε ⊥; 11.8, η; 72.7 |
| 87 | 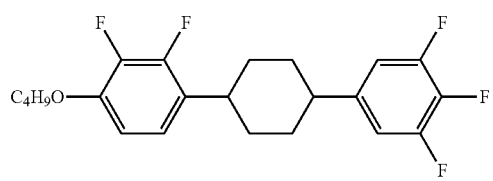
C 65.7 I
$T_{NI}$; 1.0° C., Δ n; 0.070,
Δ ε; 8.57, ε ⊥; 12.4, η; 76.0 |
| 88 | 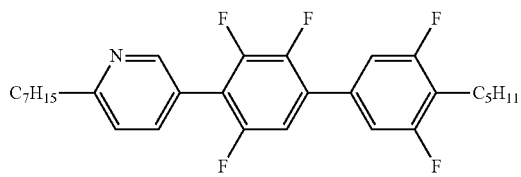 |
| 89 | 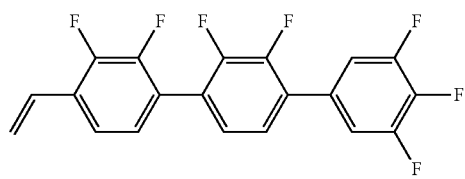 [SMILES: C=Cc1ccc(-c2ccc(-c3cc(F)c(F)c(F)c3)c(F)c2F)c(F)c1F] |
| 90 | 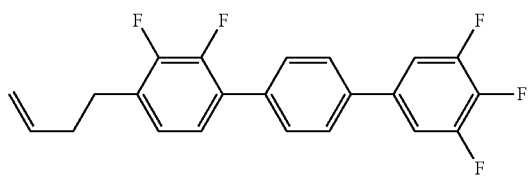 [SMILES: C=CCCc1ccc(-c2ccc(-c3cc(F)c(F)c(F)c3)cc2)c(F)c1F] |
| 91 | 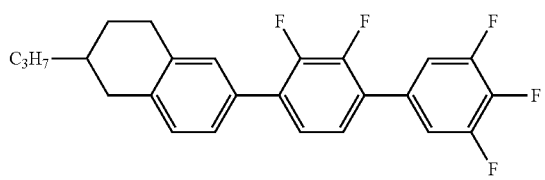 |

-continued
| No. | |
|---|---|
| 92 | 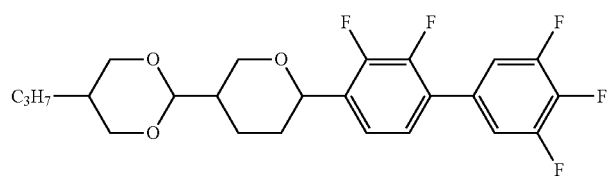 |
| 93 | 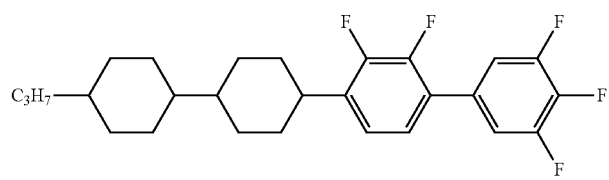 |
| 94 | 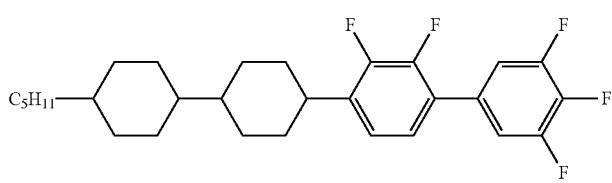 |
| 95 | 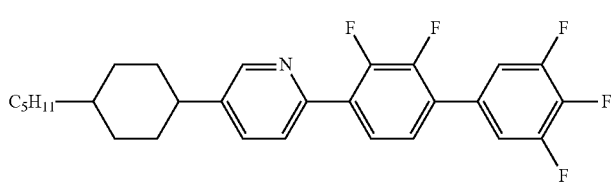 |
| 96 | 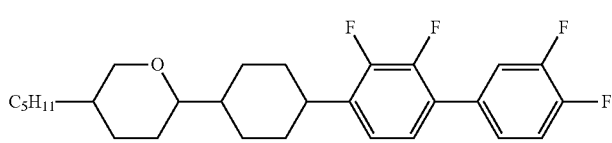 |
| 97 | 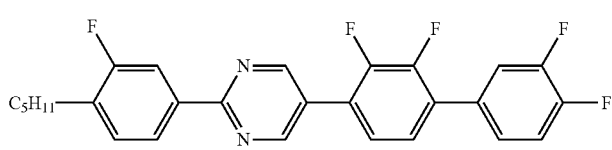 |
| 98 | 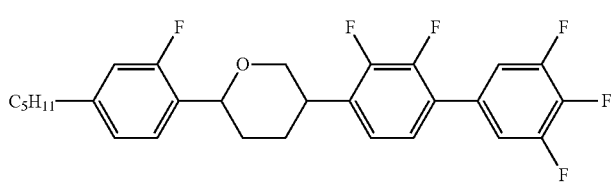 |
| 99 | 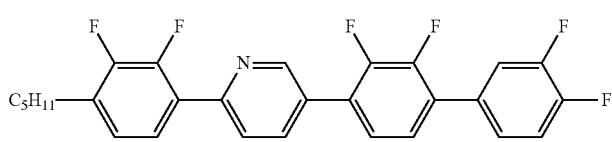 |
| 100 | 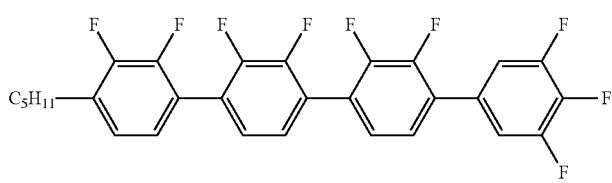 |

-continued
| No. | |
|---|---|
| 101 | 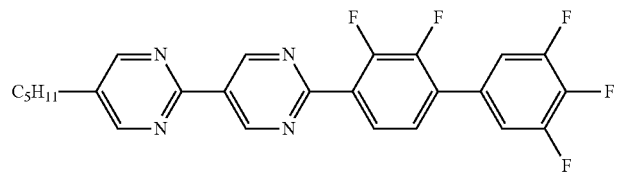 |
| 102 | 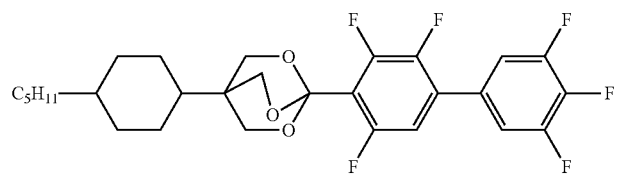 |
| 103 | 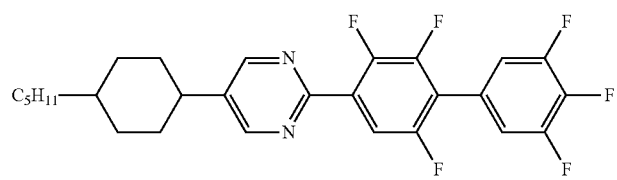 |
| 104 | 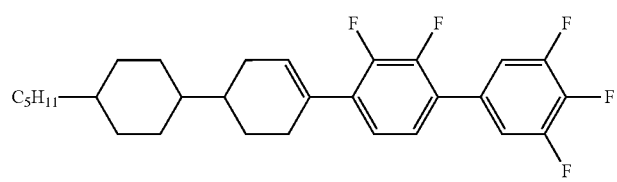 |
| 105 | 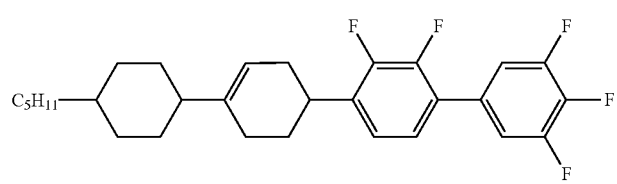 |
| 106 | 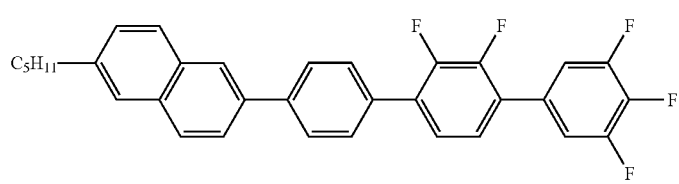 |
| 107 | 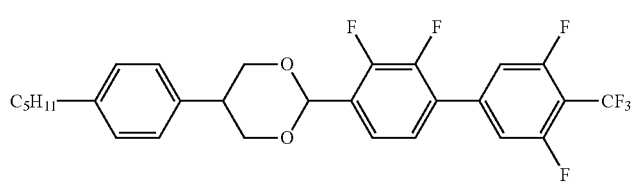 |
| 108 | 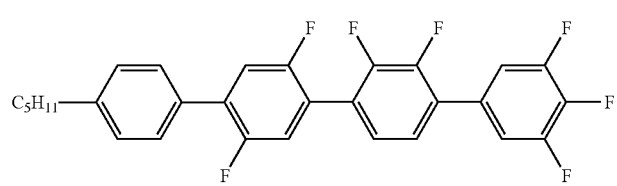 |

| No. |
|---|
| 109 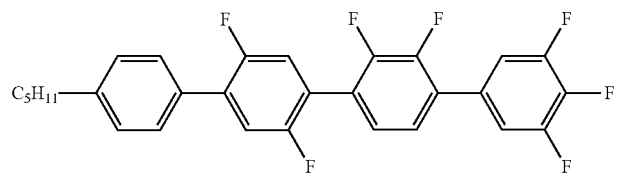 |
| 110 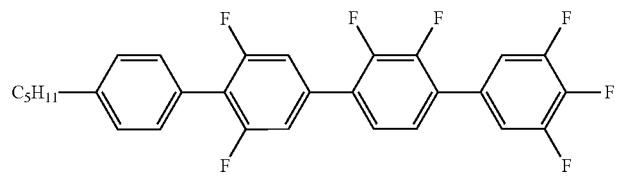 |
| 111 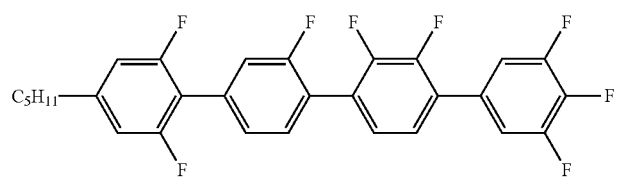 |
| 112 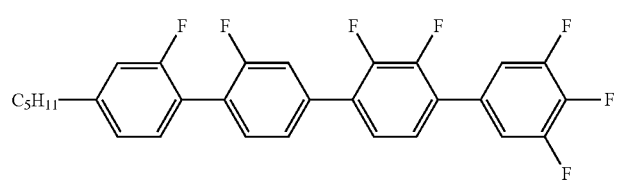 |
| 113 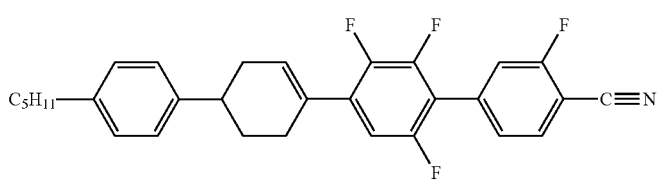 |
| 114 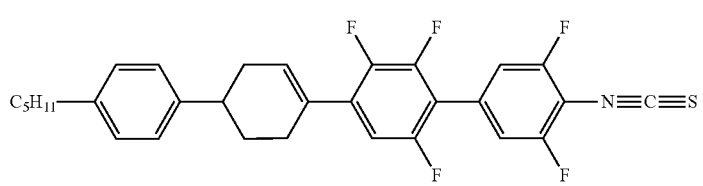 |
| 115 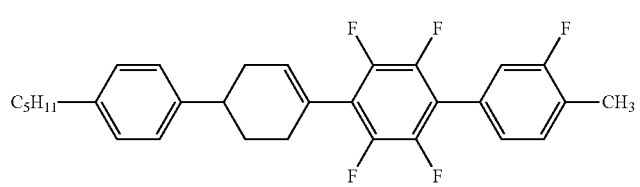 |
| 116 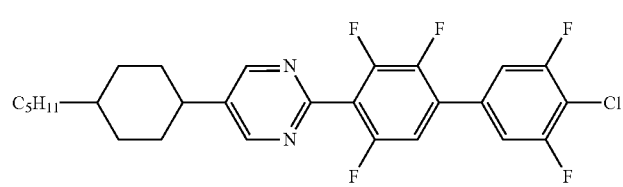 |

-continued
| No. |  |
|---|---|
| 117 | 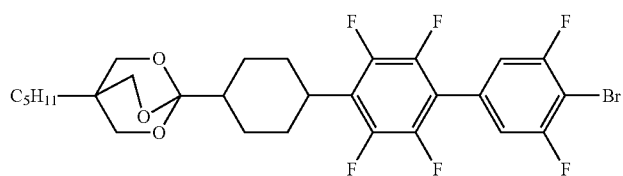 |
| 118 | 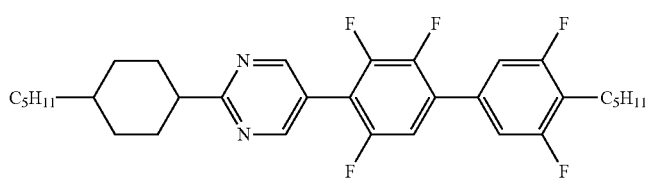 |
| 119 | 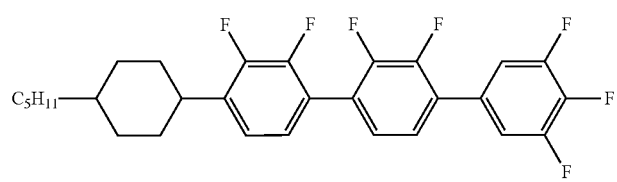 |
| 120 | 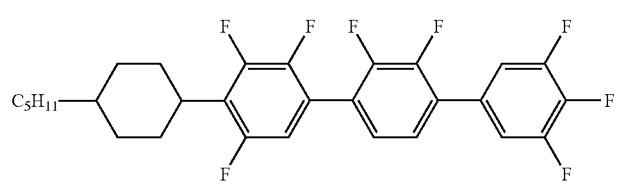 |
| 121 | 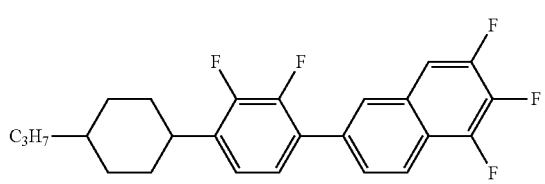 |
| 122 | 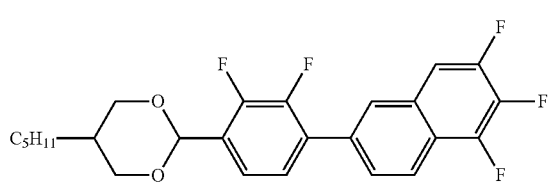 |
| 123 | 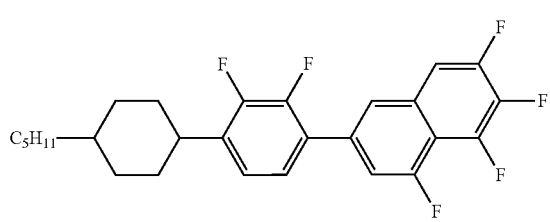 |
| 124 | 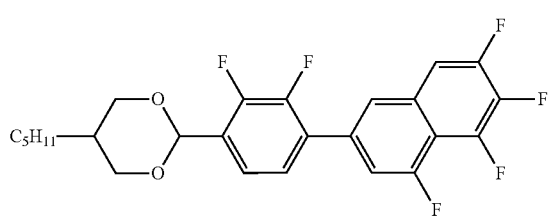 |

-continued
| No. | |
|---|---|
| 125 | 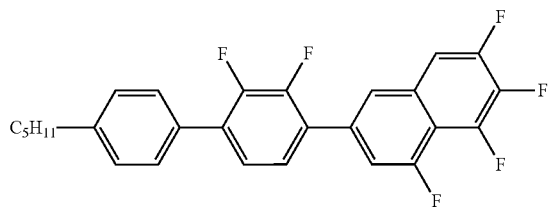 |
| 126 | 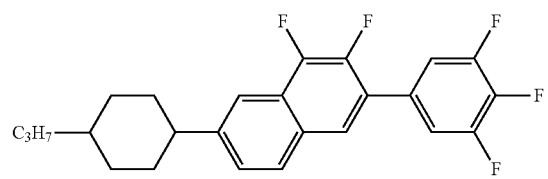 |
| 127 | 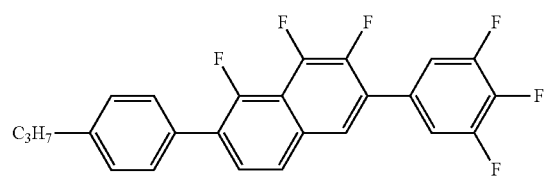 |
| 128 | 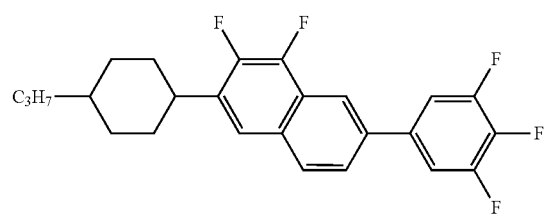 |
| 129 | 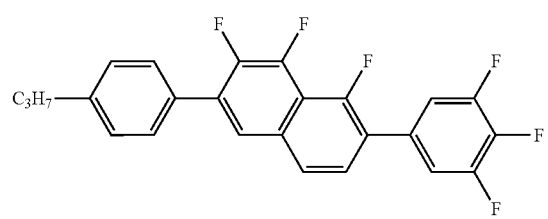 |
| 130 | 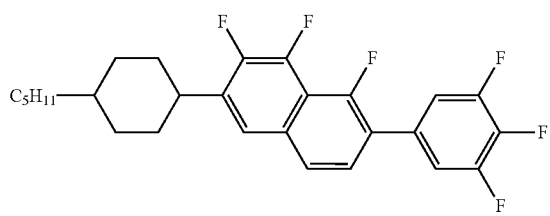 |
| 131 | 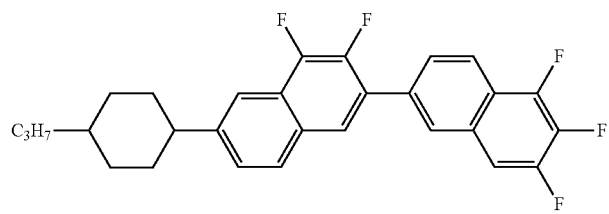 |

-continued
| No. | |
|---|---|
| 132 | 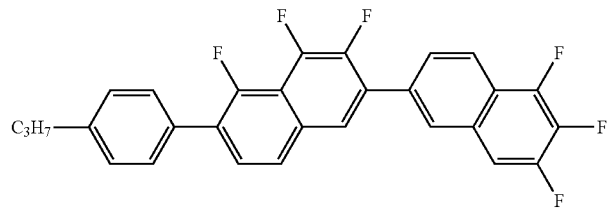 |
| 133 | 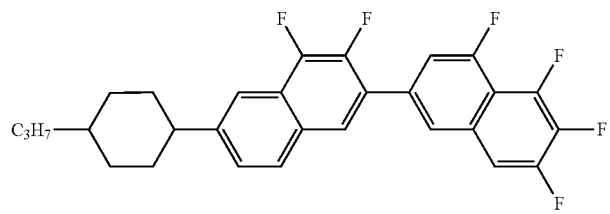 |
| 134 | 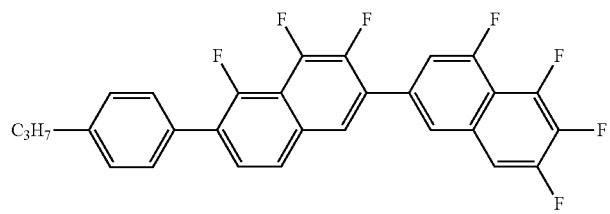 |
| 135 | 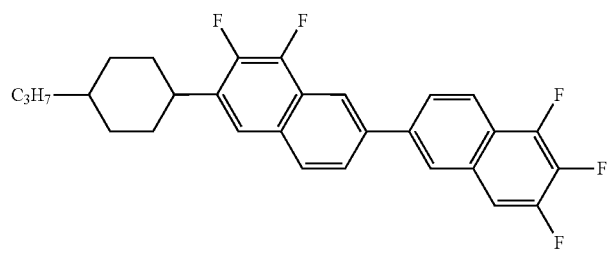 |
| 136 | 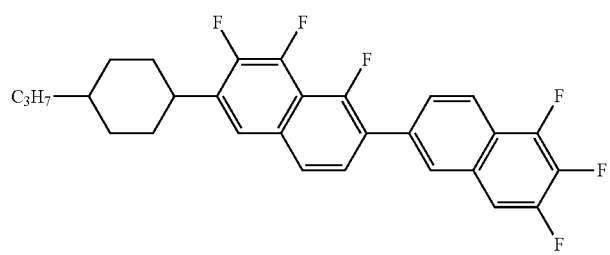 |
| 137 | 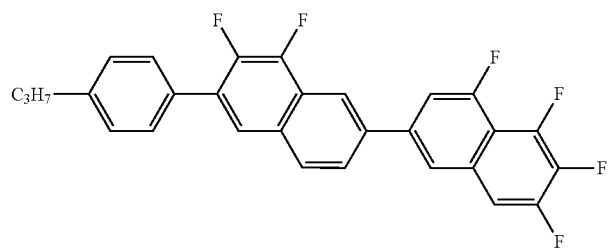 |

-continued

| No. | |
|---|---|
| 138 | 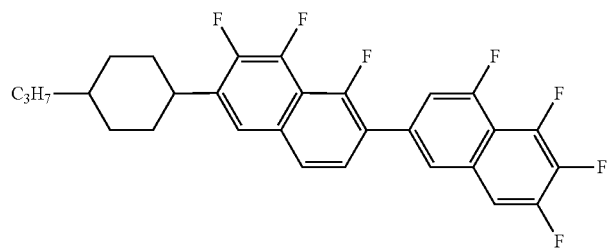 |
| 139 | 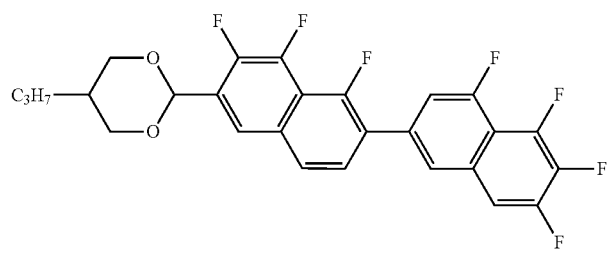 |
| 140 | 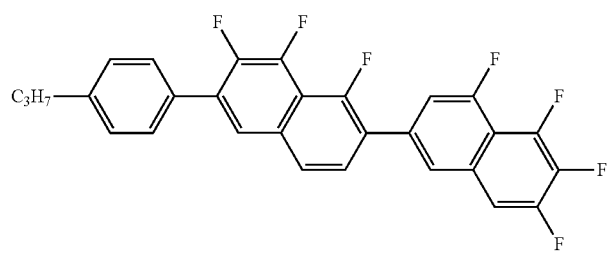 |

Comparative Example 1

As a comparative compound, compound (S-1) was synthesized. The reason is that the compound is described in JP 2002-327175 A and similar to the compound of the invention.

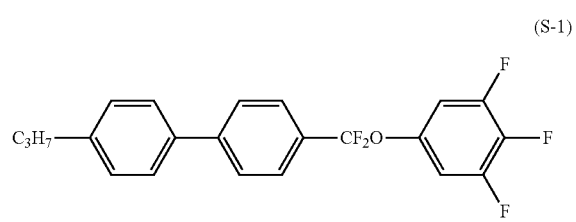
(S-1)

Chemical shift δ (ppm; CDCl$_3$): 7.75 (d, J=8.4 Hz, 2H), 7.68 (d, J=8.4 Hz, 2H), 7.53 (d, J=8.1 Hz, 2H), 7.29 (d, J=8.1 Hz, 2H), 7.02-6.94 (m, 2H), 2.65 (t, J=7.9 Hz, 2H), 1.75-1.65 (m, 2H), 0.98 (t, J=7.5 Hz, 3H).

Physical properties of comparative compound (S-1) were as described below.

Transition temperature: C 80.3 I.

Maximum temperature ($T_{NI}$)=35.0° C.; optical anisotropy (Δn)=0.144; dielectric anisotropy (Δ∈)=19.6; dielectric constant in a minor axis direction (∈⊥)=5.2; viscosity (η)=19.6 mPa·s.

TABLE 1

| Comparison of ∈⊥ | |
|---|---|
| Liquid crystal compound | ∈⊥ |
| Compound No. 7 | 15.73 |
| Compound No. 38 | 8.4 |
| Compound No. 40 | 7.4 |
| Comparative compound (S-1) | 5.2 |

Any of compound (No. 7), compound (No. 38) and compound (No. 40) shown in Examples 1 to 3 has the large dielectric constant in the minor axis direction in comparison with comparative compound (S-1). Therefore, the compound of the invention is found to be an excellent compound that can improve the transmittance of the liquid crystal composition used in an FFS mode liquid crystal display device.

1-2. Example of Liquid Crystal Composition

The invention will be described in greater detail by way of Examples. Compounds in Examples were described using symbols according to a definition in Table 4 below. In Table 4, a configuration of 1,4-cyclohexylene is trans. A parenthesized number next to a symbolized compound in Examples corresponds to the number of a compound. A symbol (-) means any other liquid crystal compound. A ratio (percentage) of the liquid crystal compound was expressed in terms of weight percent (% by weight) based on the weight of the liquid crystal composition. Values of physical properties of the composition were summarized in a last part. Physical properties were measured according to the methods described above, and measured values were directly described without extrapolation.

TABLE 2

Method for Description of Compounds using Symbols
R—(A₁)—Z₁— . . . —Zn—(An)—R'

1) Left-terminal Group R—

| | Symbol |
|---|---|
| $C_nH_{2n+1}$— | n- |
| $C_nH_{2n+1}O$— | nO— |
| $C_mH_{2m+1}C_nH_{2n}$— | mOn— |
| $CH_2=CH$— | V— |
| $C_nH_{2n+1}$—CH=CH— | nV— |
| $CH_2=CH$—$C_nH_{2n}$— | Vn— |
| $C_mH_{2m+1}$—CH=CH—$C_nH_{2n}$— | mVn— |
| $CF_2=CH$— | VFF— |
| $CF_2=CH$—$C_nH_{2n}$— | VFFn— |

2) Right-terminal Group —R'

| | Symbol |
|---|---|
| —$C_nH_{2n+1}$ | -n |
| —$OC_nH_{2n+1}$ | —On |
| —$COOCH_3$ | —EMe |
| —$CH=CH_2$ | —V |
| —CH=CH—$C_nH_{2n+1}$ | —Vn |
| —$C_nH_{2n}$—CH=$CH_2$ | —nV |
| —$C_mH_{2m}$—CH=CH—$C_nH_{2n+1}$ | —mVn |
| —CH=$CF_2$ | —VFF |
| —F | —F |
| —Cl | —CL |
| —$OCF_3$ | —OCF3 |
| —$OCF_2H$ | —OCF2H |
| —$CF_3$ | —CF3 |
| —OCH=CH—$CF_3$ | —OVCF3 |
| —C≡N | —C |

3) Bonding Group —$Z_n$—

| | Symbol |
|---|---|
| —$C_nH_{2n}$— | n |
| —COO— | E |
| —CH=CH— | V |
| —$CH_2O$— | 1O |
| —$OCH_2$— | O1 |
| —$CF_2O$— | X |
| —C≡C— | T |

4) Ring Structure —$A_n$—

| | Symbol |
|---|---|
| 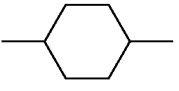 | H |
|  | B |
| 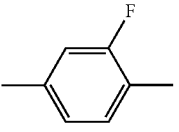 | B(F) |
| 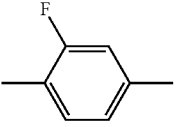 | B(2F) |
| 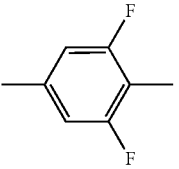 | B(F,F) |
| 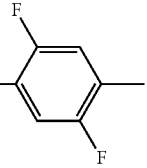 | B(2F,5F) |
| 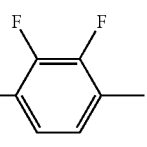 | B(2F,3F) |
| 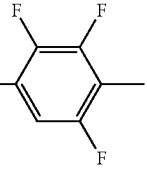 | B(2F,3F,5F) |
| 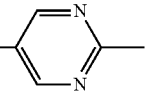 | Py |
| 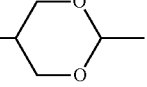 | G |
| 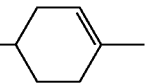 | ch |
| 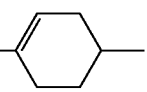 | Ch |
| 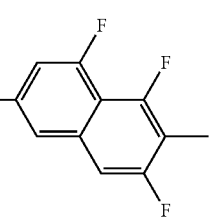 | Np(4F,5F,7F) |
| 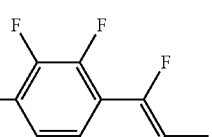 | Np(3F,4F,5F) |

5) Examples of Description

Example 1 3-B(2F,3F)B(F,F)—F

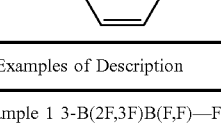

TABLE 2-continued

Example 2  3-GB(2F,3F)B(F,F)—F

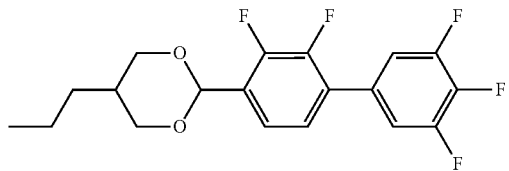 [SMILES: CCCC1COC(c2ccc(-c3cc(F)c(F)c(F)c3)c(F)c2F)OC1]

Example 4

| | | |
|---|---|---|
| 3-B(2F,3F)B(F,F)-F | (No. 7) | 8% |
| 3-HB-O2 | (13-5) | 10% |
| 5-HB-CL | (2-2) | 13% |
| 3-HBB(F,F)-F | (3-24) | 5% |
| 3-PyB(F)-F | (2-15) | 10% |
| 5-PyB(F)-F | (2-15) | 10% |
| 3-PyBB-F | (3-80) | 8% |
| 4-PyBB-F | (3-80) | 8% |
| 5-PyBB-F | (3-80) | 8% |
| 5-HBB(F)B-2 | (15-5) | 10% |
| 5-HBB(F)B-3 | (15-5) | 10% |

NI = 79.2° C.;
η = 37.9 mPa · s;
Δn = 0.172;
Δ∈ = 7.6

Example 5

| | | |
|---|---|---|
| 3-HB(2F,3F)B(F,F)-F | (No. 38) | 10% |
| 2-HB-C | (5-1) | 5% |
| 3-HB-C | (5-1) | 12% |
| 3-HB-O2 | (13-5) | 15% |
| 2-BTB-1 | (13-10) | 3% |
| 3-HHB-F | (3-1) | 4% |
| 3-HHB-1 | (14-1) | 8% |
| 3-HHB-O1 | (14-1) | 5% |
| 3-HHB-3 | (14-1) | 14% |
| 2-HHB(F)-F | (3-2) | 5% |
| 3-HHB(F)-F | (3-2) | 7% |
| 5-HHB(F)-F | (3-2) | 7% |
| 3-HHB(F,F)-F | (3-3) | 5% |

NI = 81.9° C.;
η = 16.0 mPa · s;
Δn = 0.096;
Δ∈ = 5.5

Example 6

| | | |
|---|---|---|
| 3-B(2F,3F,5F)B(F,F)-F | (No. 40) | 5% |
| 7-HB(F,F)-F | (2-4) | 3% |
| 3-HB-O2 | (13-5) | 5% |
| 2-HHB(F)-F | (3-2) | 9% |
| 3-HHB(F)-F | (3-2) | 9% |
| 5-HHB(F)-F | (3-2) | 9% |
| 2-HBB(F)-F | (3-23) | 9% |
| 3-HBB(F)-F | (3-23) | 9% |
| 5-HBB(F)-F | (3-23) | 16% |
| 2-HBB-F | (3-22) | 4% |
| 3-HBB-F | (3-22) | 4% |
| 5-HBB-F | (3-22) | 3% |
| 3-HBB(F,F)-F | (3-24) | 5% |
| 5-HBB(F,F)-F | (3-24) | 10% |

NI = 82.3° C.;
η = 27.8 mPa · s;
Δn = 0.116;
Δ∈ = 6.6

Example 7

| | | |
|---|---|---|
| 5-chB(2F,3F)B(F,F)-F | (No. 74) | 5% |
| 3-HB-O2 | (13-5) | 10% |
| 5-HB-CL | (2-2) | 13% |
| 3-HBB(F,F)-F | (3-24) | 7% |
| 3-PyB(F)-F | (2-15) | 10% |
| 5-PyB(F)-F | (2-15) | 10% |
| 3-PyBB-F | (3-80) | 10% |
| 4-PyBB-F | (3-80) | 10% |
| 5-PyBB-F | (3-80) | 9% |
| 5-HBB(F)B-2 | (15-5) | 8% |
| 5-HBB(F)B-3 | (15-5) | 8% |

Example 8

| | | |
|---|---|---|
| 5-GB(2F,3F)B(F,F)-F | (No. 70) | 9% |
| 5-HB-F | (2-2) | 12% |
| 6-HB-F | (2-2) | 9% |
| 7-HB-F | (2-2) | 7% |
| 2-HHB-OCF$_3$ | (3-1) | 5% |
| 3-HHB-OCF$_3$ | (3-1) | 6% |
| 4-HHB-OCF$_3$ | (3-1) | 6% |
| 5-HHB-OCF$_3$ | (3-1) | 5% |
| 3-HH2B-OCF$_3$ | (3-4) | 4% |
| 5-HH2B-OCF$_3$ | (3-4) | 3% |
| 3-HHB(F,F)-OCF$_2$H | (3-3) | 4% |
| 3-HHB(F,F)-OCF$_3$ | (3-3) | 4% |
| 3-HH2B(F)-F | (3-5) | 3% |
| 3-HBB(F)-F | (3-23) | 8% |
| 5-HBB(F)-F | (3-23) | 9% |
| 5-HBBH-3 | (15-1) | 3% |
| 3-HB(F)BH-3 | (15-2) | 3% |

Example 9

| | | |
|---|---|---|
| 3-B(2F,3F)HB(F,F)-F | (No. 7) | 5% |
| 3-HB-CL | (2-2) | 6% |
| 5-HB-CL | (2-2) | 4% |
| 3-HHB-OCF$_3$ | (3-1) | 5% |
| 3-H2HB-OCF$_3$ | (3-13) | 5% |
| 5-H4HB-OCF$_3$ | (3-19) | 10% |
| V-HHB(F)-F | (3-2) | 5% |
| 3-HHB(F)-F | (3-2) | 5% |
| 5-HHB(F)-F | (3-2) | 5% |
| 3-H4HB(F,F)-CF$_3$ | (3-21) | 8% |
| 5-H4HB(F,F)-CF$_3$ | (3-21) | 10% |
| 5-H2HB(F,F)-F | (3-15) | 5% |
| 5-H4HB(F,F)-F | (3-21) | 7% |
| 2-H2BB(F)-F | (3-26) | 5% |
| 3-H2BB(F)-F | (3-26) | 10% |
| 3-HBEB(F,F)-F | (3-39) | 5% |

Example 10

| | | |
|---|---|---|
| 3-B(2F,3F)B(F,F)-F | (No. 7) | 5% |
| 3-HB(2F,3F)B(F,F)-F | (No. 38) | 6% |
| 5-HB-CL | (2-2) | 3% |
| 7-HB(F)-F | (2-3) | 4% |
| 3-HH-4 | (13-1) | 8% |
| 3-HH-EMe | (13-2) | 20% |
| 3-HHEB-F | (3-10) | 8% |
| 5-HHEB-F | (3-10) | 8% |
| 3-HHEB(F,F)-F | (3-12) | 10% |
| 4-HHEB(F,F)-F | (3-12) | 5% |
| 4-HGB(F,F)-F | (3-103) | 5% |
| 5-HGB(F,F)-F | (3-103) | 6% |
| 2-H2GB(F,F)-F | (3-106) | 4% |
| 3-H2GB(F,F)-F | (3-106) | 3% |
| 5-GHB(F,F)-F | (3-109) | 5% |

NI = 70.9° C.;
η = 22.0 mPa · s;
Δn = 0.064;
Δ∈ = 6.3

Example 11

| | | |
|---|---|---|
| 3-HB(2F,3F,5F)B(F,F)-F | (No. 40) | 5% |
| 3-HHB(F,F)-F | (3-3) | 9% |
| 3-H2HB(F,F)-F | (3-15) | 8% |
| 4-H2HB(F,F)-F | (3-15) | 8% |
| 5-H2HB(F,F)-F | (3-15) | 8% |
| 3-HBB(F,F)-F | (3-24) | 18% |
| 5-HBB(F,F)-F | (3-24) | 18% |
| 3-H2BB(F,F)-F | (3-27) | 10% |
| 5-HHBB(F,F)-F | (4-6) | 3% |
| 5-HHEBB-F | (4-17) | 2% |
| 3-HH2BB(F,F)-F | (4-15) | 3% |
| 1O1-HBBH-4 | (15-1) | 4% |
| 1O1-HBBH-5 | (15-1) | 4% |

NI = 95.6° C.;
η = 36.6 mPa · s;
Δn = 0.115;
Δ∈ = 9.5

A pitch when 0.25 part of Op-05 was added to 100 parts of the above composition was 64.8 μm.

Example 12

| | | |
|---|---|---|
| 5-chB(2F,3F)B(F,F)-F | (No. 74) | 5% |
| 5-GB(2F,3F)B(F,F)-F | (No. 70) | 5% |
| 3-HB-C | (5-1) | 12% |
| 3-HB-O2 | (13-5) | 15% |
| 2-BTB-1 | (13-10) | 3% |
| 3-HHB-F | (3-1) | 4% |
| 3-HHB-1 | (14-1) | 8% |
| 3-HHB-O1 | (14-1) | 5% |
| 3-HHB-3 | (14-1) | 10% |
| 3-HHEB-F | (3-10) | 4% |
| 5-HHEB-F | (3-10) | 4% |
| 2-HHB(F)-F | (3-2) | 6% |
| 3-HHB(F)-F | (3-2) | 7% |
| 5-HHB(F)-F | (3-2) | 7% |
| 3-HHB(F,F)-F | (3-3) | 5% |

Example 13

| | | |
|---|---|---|
| 3-B(2F,3F)HB(F,F)-F | (No. 7) | 4% |
| 7-HB(F,F)-F | (2-4) | 3% |
| 3-HB-O2 | (13-5) | 7% |
| 2-HHB(F)-F | (3-2) | 9% |
| 3-HHB(F)-F | (3-2) | 9% |
| 5-HHB(F)-F | (3-2) | 9% |
| 2-HBB(F)-F | (3-23) | 9% |
| 3-HBB(F)-F | (3-23) | 9% |
| 5-HBB(F)-F | (3-23) | 15% |
| 2-HBB-F | (3-22) | 4% |
| 3-HBB-F | (3-22) | 4% |
| 5-HBB-F | (3-22) | 3% |
| 3-HBB(F,F)-F | (3-24) | 5% |
| 5-HBB(F,F)-F | (3-24) | 10% |

Example 14

| | | |
|---|---|---|
| 5-GB(2F,3F)B(F,F)-F | (No. 70) | 10% |
| 3-HB-O2 | (13-5) | 8% |
| 5-HB-CL | (2-2) | 12% |
| 3-HBB(F,F)-F | (3-24) | 6% |
| 3-PyB(F)-F | (2-15) | 10% |
| 5-PyB(F)-F | (2-15) | 10% |
| 3-PyBB-F | (3-80) | 10% |
| 4-PyBB-F | (3-80) | 8% |
| 5-PyBB-F | (3-80) | 9% |
| 5-HBB(F)B-2 | (15-5) | 9% |
| 5-HBB(F)B-3 | (15-5) | 8% |

NI = 90.1° C.;
η = 44.4 mPa · s;
Δn = 0.183;
Δ∈ = 9.3

Example 15

| | | |
|---|---|---|
| 5-PyB(2F,3F)B(F,F)-F | (No. 71) | 7% |
| 2-HB-C | (5-1) | 5% |
| 3-HB-C | (5-1) | 11% |
| 3-HB-O2 | (13-5) | 13% |
| 2-BTB-1 | (13-10) | 3% |
| 3-HHB-F | (3-1) | 4% |
| 3-HHB-1 | (14-1) | 8% |
| 3-HHB-O1 | (14-1) | 5% |
| 3-HHB-3 | (14-1) | 14% |
| 3-HHEB-F | (3-10) | 4% |
| 5-HHEB-F | (3-10) | 3% |
| 2-HHB(F)-F | (3-2) | 6% |
| 3-HHB(F)-F | (3-2) | 6% |
| 5-HHB(F)-F | (3-2) | 6% |
| 3-HHB(F,F)-F | (3-3) | 5% |

NI = 97.4° C.;
η = 22.1 mPa · s;
Δn = 0.105;
Δ∈ = 6.1

Example 16

| | | |
|---|---|---|
| 4O-B(2F,3F)ChB(F,F)-F | (No. 86) | 9% |
| 7-HB(F,F)-F | (2-4) | 3% |
| 3-HB-O2 | (13-5) | 7% |
| 2-HHB(F)-F | (3-2) | 10% |
| 3-HHB(F)-F | (3-2) | 8% |
| 5-HHB(F)-F | (3-2) | 9% |

| | | |
|---|---|---|
| 2-HBB(F)-F | (3-23) | 6% |
| 3-HBB(F)-F | (3-23) | 8% |
| 5-HBB(F)-F | (3-23) | 16% |
| 2-HBB-F | (3-22) | 4% |
| 3-HBB-F | (3-22) | 4% |
| 5-HBB-F | (3-22) | 3% |
| 3-HBB(F,F)-F | (3-24) | 5% |
| 5-HBB(F,F)-F | (3-24) | 8% |

NI = 79.5° C.;
η = 28.4 mPa · s;
Δn = 0.114;
Δ∈ = 5.9

Example 17

| | | |
|---|---|---|
| 4O-B(2F,3F)HB(F,F)-F | (No. 87) | 5% |
| 3-HHB(F,F)-F | (3-3) | 9% |
| 3-H2HB(F,F)-F | (3-15) | 7% |
| 4-H2HB(F,F)-F | (3-15) | 8% |
| 5-H2HB(F,F)-F | (3-15) | 7% |
| 3-HBB(F,F)-F | (3-24) | 21% |
| 5-HBB(F,F)-F | (3-24) | 20% |
| 3-H2BB(F,F)-F | (3-27) | 9% |
| 5-HHBB(F,F)-F | (4-6) | 3% |
| 5-HHEBB-F | (4-17) | 2% |
| 3-HH2BB(F,F)-F | (4-15) | 3% |
| 1O1-HBBH-4 | (15-1) | 3% |
| 1O1-HBBH-5 | (15-1) | 3% |

NI = 90.8° C.;
η = 36.6 mPa · s;
Δn = 0.113;
Δ∈ = 9.1

Example 18

| | | |
|---|---|---|
| 5-HNp(3F,4F,5F)B(F,F)-F | (No. 129) | 6% |
| 5-HB-F | (2-2) | 10% |
| 6-HB-F | (2-2) | 7% |
| 7-HB-F | (2-2) | 6% |
| 2-HHB-OCF$_3$ | (3-1) | 7% |
| 3-HHB-OCF$_3$ | (3-1) | 7% |
| 4-HHB-OCF$_3$ | (3-1) | 7% |
| 5-HHB-OCF$_3$ | (3-1) | 5% |
| 3-HH2B-OCF$_3$ | (3-4) | 4% |
| 5-HH2B-OCF$_3$ | (3-4) | 4% |
| 3-HHB(F,F)-OCF$_3$ | (3-3) | 5% |
| 3-HH2B(F)-F | (3-5) | 3% |
| 3-HBB(F)-F | (3-23) | 10% |
| 5-HBB(F)-F | (3-23) | 10% |
| 5-HBBH-3 | (15-1) | 3% |
| 3-HB(F)BH-3 | (15-2) | 3% |

Example 19

| | | |
|---|---|---|
| 5-HB(2F,3F)Np(4F,5F,7F)-F | (No. 123) | 8% |
| 3-HB-CL | (2-2) | 6% |
| 5-HB-CL | (2-2) | 4% |
| 3-HHB-OCF$_3$ | (3-1) | 5% |
| 5-H4HB-OCF$_3$ | (3-19) | 15% |
| V-HHB(F)-F | (3-2) | 5% |
| 3-HHB(F)-F | (3-2) | 5% |
| 5-HHB(F)-F | (3-2) | 5% |
| 3-H4HB(F,F)-CF$_3$ | (3-21) | 5% |
| 5-H4HB(F,F)-CF$_3$ | (3-21) | 10% |
| 5-H2HB(F,F)-F | (3-15) | 5% |
| 5-H4HB(F,F)-F | (3-21) | 7% |
| 2-H2BB(F)-F | (3-26) | 5% |
| 3-H2BB(F)-F | (3-26) | 10% |
| 3-HBEB(F,F)-F | (3-39) | 5% |

Although the invention has been described and illustrated with a certain degree of particularity, it was understood that the disclosure has been made only by way of example, and that numerous changes in the conditions and order of steps can be resorted to by those skilled in the art without departing from the spirit and scope of the invention.

INDUSTRIAL APPLICABILITY

A liquid crystal compound of the invention satisfies at least one of physical properties such as a high stability to heat, light and so forth, a high clearing point, a low minimum temperature of a liquid crystal phase, a small viscosity, a suitable optical anisotropy, a large dielectric anisotropy, a large dielectric constant in a minor axis direction, a suitable elastic constant and an excellent compatibility with other liquid crystal compounds. A liquid crystal composition of the invention contains the compound, and satisfies at least one of physical properties such as a high maximum temperature, a low minimum temperature, a small viscosity, a suitable optical anisotropy, a large dielectric anisotropy, a large dielectric constant in a minor axis direction and a suitable elastic constant. The composition has a suitable balance regarding at least two of the physical properties. A liquid crystal display device of the invention includes the composition, and has a wide temperature range in which the device can be used, a short response time, a large voltage holding ratio, a low threshold voltage, a large contrast ratio and a long service life. Accordingly, the device of the invention can be widely utilized in the liquid crystal display device such as a personal computer, and a television.

What is claimed is:

1. A compound represented by formula (1-1):

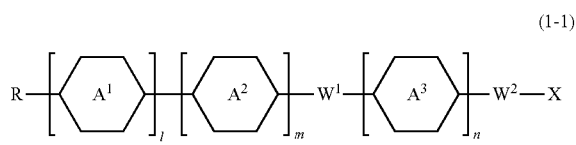

(1-1)

wherein, in formula (1-1),
R is hydrogen or alkyl having 1 to 10 carbons, and in the alkyl, at least one of —CH$_2$— may be replaced by —O— or —S—, at least one of —(CH$_2$)$_2$— may be replaced by —CH=CH—, and in the groups, at least one of hydrogen may be replaced by halogen;
ring A$^1$, ring A$^2$ and ring A$^3$ are independently 1,4-cyclohexylene, 1,4-cyclohexenylene, tetrahydropyran-2,5-diyl, 1,3-dioxane-2,5-diyl, 2,6,7-trioxabicyclo[2.2.2]octane-1,4-diyl, pyrimidine-2,5-diyl, pyridine-2,5-diyl, naphthalene-2,6-diyl, decahydronaphthalene-2,6-diyl, 1,2,3,4-tetrahydronaphthalene-2,6-diyl, 1,4-phenylene, or 1,4-phenylene in which at least one of hydrogen is replaced by halogen;
W$^1$ is a group represented by formula (1a) or formula (1b);

(1a)

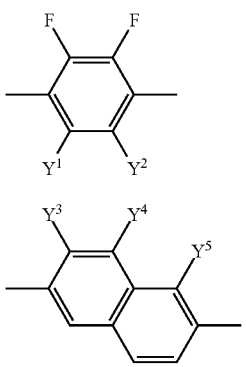

(1b)

wherein, in formula (1a) and formula (1b),
Y$^1$ and Y$^2$ are independently hydrogen, chlorine or fluorine, Y$^3$, Y$^4$ and Y$^5$ are independently hydrogen, fluorine or chlorine, and at least two of Y$^3$, Y$^4$ and Y$^5$ is fluorine or chlorine; and
in formula (1-1),
W$^2$ is a group represented by formula (1c) or formula (1d);

(1c)

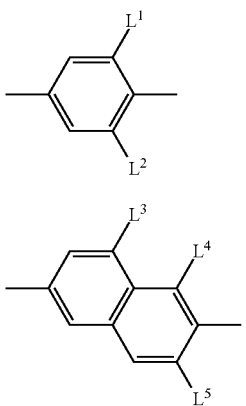

(1d)

wherein, in formula (1c) and formula (1d),
L$^1$, L$^2$, L$^3$, L$^4$ and L$^5$ are independently hydrogen, fluorine or chlorine; and
in formula (1-1),
X is halogen, —C≡N, —N=C=S, —SF$_5$, —CF$_3$, —CF$_2$H, —CFH$_2$, —OCF$_3$, —OCF$_2$H, —OCFH$_2$ or alkyl having 1 to 10 carbons, and in the alkyl, at least one of —CH$_2$— may be replaced by —O— or —S—, at least one of —(CH$_2$)$_2$— may be replace by CH=CH—, and in the groups, at least one of hydrogen may be replaced by halogen; and
l, m and n are 0 or 1, and a sum of l, m and n is 0, 1 or 2;
in which, when a sum of l and m is 1 and n is 0, at least one of W$^1$ and W$^2$ is a group represented by formula (1b) or formula (1d), or at least one of l piece of ring A$^1$ and m pieces of ring A$^2$ is 1,4-cyclohexylene, 1,4-cyclohexenylene, tetrahydropyran-2,5-diyl, 1,3-dioxane-2,5-diyl, 2,6,7-trioxabicyclo[2.2.2]octane-1,4-diyl, pyrimidine-2,5-diyl, pyridine-2,5-diyl, naphthalene-2,6-diyl, decahydronaphthalene-2,6-diyl, 1,2,3,4-tetrahydronaphthalene-2,6-diyl, or 1,4-phenylene in which at least one of hydrogen is replaced by halogen.

2. The compound according to claim 1, represented by formula (1-2):

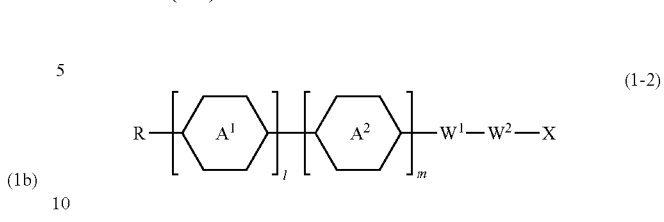

(1-2)

wherein, in formula (1-2),
R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;
ring A$^1$ and ring A$^2$ are independently 1,4-cyclohexylene, 1,4-cyclohexenylene, 1,3-dioxane-2,5-diyl, 2,6,7-trioxabicyclo[2.2.2]octane-1,4-diyl, pyrimidine-2,5-diyl, naphthalene-2,6-diyl, 2-fluoro-1,4-phenylene, 3-fluoro-1,4-phenylene, 2,3-difluoro-1,4-phenylene or 3,5-difluoro-1,4-phenylene;
W$^1$ is a group represented by formula (1a) or formula (1b);

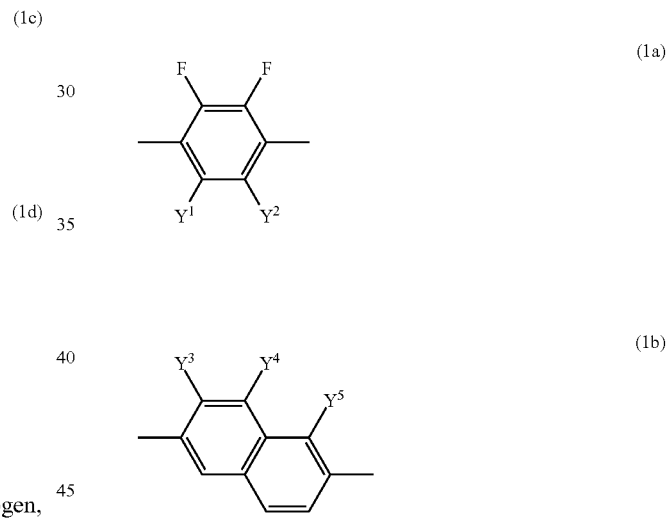

wherein, in formula (1a) and formula (1b),
Y$^1$ and Y$^2$ are independently hydrogen, chlorine or fluorine, Y$^3$, Y$^4$ and Y$^5$ are independently hydrogen, fluorine or chlorine, and at least two of Y$^3$, Y$^4$ and Y$^5$ is fluorine or chlorine; and
in formula (1-2),
W$^2$ is a group represented by formula (1c) or formula (1d);

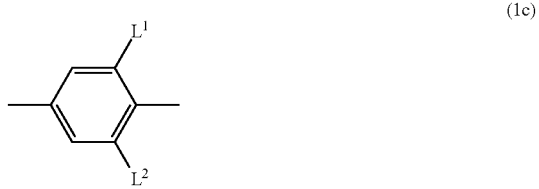

-continued (1d)

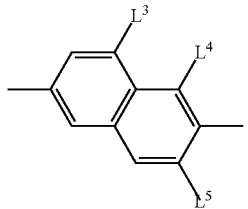

wherein, in formula (1c) and formula (1d),
$L^1$, $L^2$, $L^3$, $L^4$ and $L^5$ are independently hydrogen, fluorine or chlorine; and
in formula (1-2),
X is fluorine, chlorine, —C≡N, —N=C=S, —SF$_5$, —CH$_2$F, —CHF$_2$, —CF$_3$, —(CH$_2$)$_2$—F, —CH$_2$CF$_3$, —CF$_2$CF$_3$, —(CH$_2$)$_3$—F, —(CH$_2$)$_2$—CF$_3$, —(CF$_2$)$_3$—F, —(CH$_2$)$_4$—F, —(CH$_2$)$_3$—CF$_3$, —(CF$_2$)$_4$—F, —(CF$_2$)$_5$—F, —(CF$_2$)$_6$—F, —(CF$_2$)$_7$—F, —OCH$_2$F, —OCHF$_2$, —OCF$_3$, —O—(CH$_2$)$_2$—F, —OCH$_2$CF$_3$, —OCF$_2$CF$_3$, —O—(CH$_2$)$_3$—F, —O—(CH$_2$)$_2$—CF$_3$, —O—(CF$_2$)$_3$—F, —O(CH$_2$)$_4$—F, —O—(CH$_2$)$_3$—CF$_3$, —O—(CF$_2$)$_4$—F, —O—(CF$_2$)$_5$—F, —O—(CF$_2$)$_6$—F, —CH=CHF, —CH=CF$_2$, —CF=CHF, —CF=CF$_2$, —CH=CHCH$_2$F, —CF=CF$_2$HCF$_3$, —CF=CHCF$_3$, —CF=CFCF$_3$, —(CH$_2$)$_2$—CH=CF$_2$, —(CH$_2$)$_2$—CF=CF$_2$, —(CH$_2$)$_2$—CH=CHCF$_3$, —(CH$_2$)$_2$—CF=CHCF$_3$ or —(CH$_2$)$_2$—CF=CFCF$_3$; and
l and m are 0 or 1, and a sum of l and m is 0, 1 or 2; in which, when a sum of l and m is 1, at least one of $W^1$ and $W^2$ is a group represented by formula (1b) or formula (1d), or at least one of ring $A^1$ and ring $A^2$ is 1,4-cyclohexylene, 1,4-cyclohexenylene, 1,3-dioxane-2,5-diyl, 2,6,7-trioxabicyclo[2.2.2]octane-1,4-diyl, pyrimidine-2,5-diyl, naphthalene-2,6-diyl, 2-fluoro-1,4-phenylene, 2,3-difluoro-1,4-phenylene or 3,5-difluoro-1,4-phenylene.

3. The compound according to claim 1, represented by formula (1-3):

(1-3)

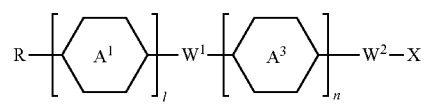

wherein, in formula (1-3),
R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;
ring $A^1$ is 1,4-cyclohexylene, 1,4-cyclohexenylene, 1,3-dioxane-2,5-diyl, 2,6,7-trioxabicyclo[2.2.2]octane-1,4-diyl, pyrimidine-2,5-diyl, naphthalene-2,6-diyl, 2-fluoro-1,4-phenylene, 3-fluoro-1,4-phenylene, 2,3-difluoro-1,4-phenylene or 3,5-difluoro-1,4-phenylene; ring $A^3$ is 1,4-cyclohexylene, 1,4-cyclohexenylene, 1,3-dioxane-2,5-diyl, 2,6,7-trioxabicyclo[2.2.2]octane-1,4-diyl, pyrimidine-2,5-diyl, naphthalene-2,6-diyl, 1,4-phenylene, 2-fluoro-1,4-phenylene, 3-fluoro-1,4-phenylene, 2,3-difluoro-1,4-phenylene or 3,5-difluoro-1,4-phenylene;

$W^1$ is a group represented by formula (1a) or formula (1b);

(1a)

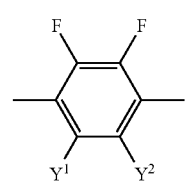

(1b)

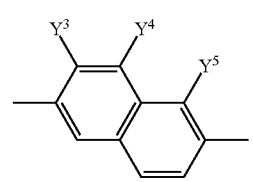

wherein, in formula (1a) and formula (1b),
$Y^1$ and $Y^2$ are independently hydrogen, chlorine or fluorine, $Y^3$, $Y^4$ and $Y^5$ are independently hydrogen, fluorine or chlorine, and at least two of $Y^3$, $Y^4$ and $Y^5$ is fluorine or chlorine; and
in formula (1-3),
$W^2$ is a group represented by formula (1c) or formula (1d);

(1c)

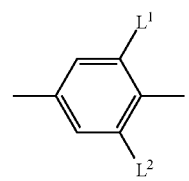

(1d)

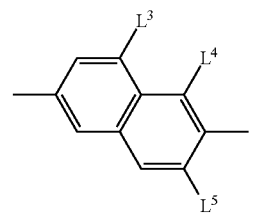

wherein, in formula (1c) and formula (1d),
$L^1$, $L^2$, $L^3$, $L^4$ and $L^5$ are independently hydrogen, fluorine or chlorine; and
in formula (1-3),
X is fluorine, chlorine, —C≡N, —N=C=S, —SF$_5$, —CH$_2$F, —CHF$_2$, —CF$_3$, —(CH$_2$)$_2$—F, —CH$_2$CF$_3$, —CF$_2$CF$_3$, —(CH$_2$)$_3$—F, —(CH$_2$)$_2$—CF$_3$, —(CF$_2$)$_3$—F, —(CH$_2$)$_4$—F, —(CH$_2$)$_3$—CF$_3$, —(CF$_2$)$_4$—F, —(CF$_2$)$_5$—F, —(CF$_2$)$_6$—F, —(CF$_2$)$_7$—F, —OCH$_2$F, —OCHF$_2$, —OCF$_3$, —O—(CH$_2$)$_2$—F, —OCH$_2$CF$_3$, —OCF$_2$CF$_3$, —O—(CH$_2$)$_3$—F, —O—(CH$_2$)$_2$—CF$_3$, —O—(CF$_2$)$_3$—F, —O(CH$_2$)$_4$—F, —O—(CH$_2$)$_3$—CF$_3$, —O—(CF$_2$)$_4$—F, —O—(CF$_2$)$_5$—F, —O—(CF$_2$)$_6$—F, —CH=CHF, —CH=CF$_2$, —CF=CHF, —CF=CF$_2$, —CH=CHCH$_2$F, —CH=CHCF$_3$, —CF=CHCF$_3$, —CF=CFCF$_3$, —(CH$_2$)$_2$—CH=CF$_2$, —(CH$_2$)$_2$—CF=CF$_2$, —(CH$_2$)$_2$—CH=CHCF$_3$, —(CH$_2$)$_2$—CF=CHCF$_3$ or —(CH$_2$)$_2$—CF=CFCF$_3$; and
l and n are 0 or 1, and a sum of l and n is 0, 1 or 2.

4. The compound according to claim 1, represented by formula (1-4):

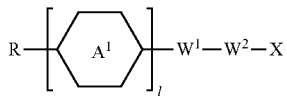
(1-4)

wherein, in formula (1-4),
R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;
ring $A^1$ is independently 1,4-cyclohexylene, 1,4-cyclohexenylene, 1,3-dioxane-2,5-diyl, pyrimidine-2,5-diyl, naphthalene-2,6-diyl, 2-fluoro-1,4-phenylene, 3-fluoro-1,4-phenylene or 2,3-difluoro-1,4-phenylene;
$W^1$ is a group represented by formula (1a) or formula (1b);

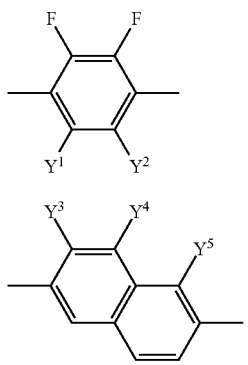
(1a)
(1b)

wherein, in formula (1c) and formula (1d),
$Y^1$ and $Y^2$ are independently hydrogen, chlorine or fluorine, $Y^3$, $Y^4$ and $Y^5$ are independently hydrogen, fluorine or chlorine, and at least two of $Y^3$, $Y^4$ and $Y^5$ is fluorine or chlorine; and
in formula (1-4),
$W^2$ is a group represented by formula (1c) or formula (1d);

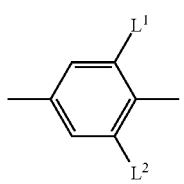
(1c)

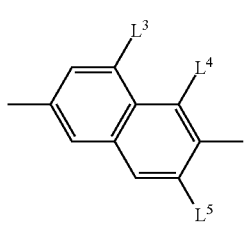
(1d)

wherein, in formula (1c) and formula (1d),
$L^1$, $L^2$, $L^3$, $L^4$ and $L^5$ are independently hydrogen, fluorine or chlorine; and
in formula (1-4),
X is fluorine, —C≡N, —N═C═S, —SF$_5$, —CF$_3$, —CHF$_2$, —CH$_2$F, —OCF$_3$, —OCHF$_2$, or —OCH$_2$F; and
l is 0 or 1.

5. The compound according to claim 1, represented by formula (1-5):

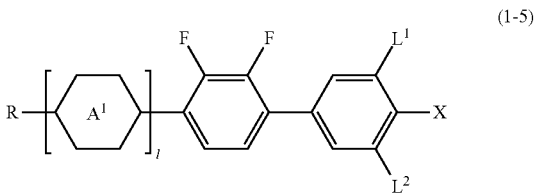
(1-5)

wherein, in formula (1-5),
R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;
ring $A^1$ is 1,4-cyclohexylene, 1,4-cyclohexenylene, 1,3-dioxane-2,5-diyl, pyrimidine-2,5-diyl, naphthalene-2,6-diyl, 1,4-phenylene, 2-fluoro-1,4-phenylene, 3-fluoro-1,4-phenylene or 2,3-difluoro-1,4-phenylene;
$L^1$ and $L^2$ are independently hydrogen or fluorine;
X is fluorine, —C≡N, —N═C═S, —SF$_5$, —CF$_3$, —CHF$_2$, —OCF$_3$, —OCHF$_2$ or —OCH$_2$F; and
l is 0 or 1.

6. The compound according to claim 1, represented by formulas (1-6-1) to (1-6-5):

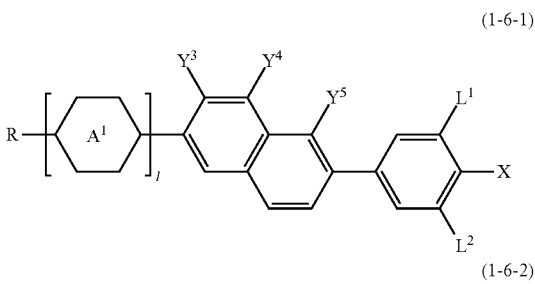
(1-6-1)

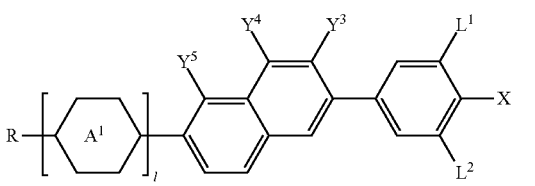
(1-6-2)

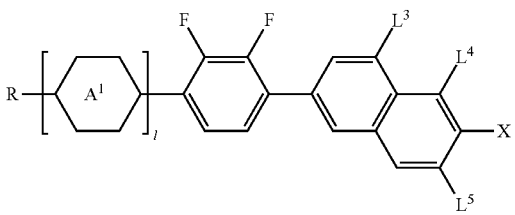
(1-6-3)

-continued (1-6-4)

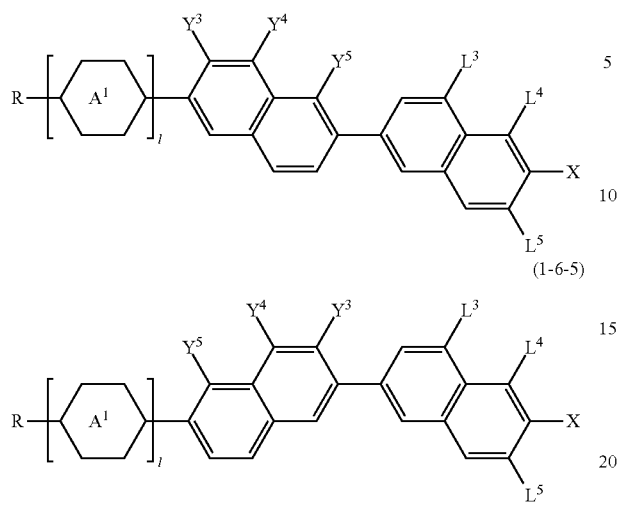

(1-6-5)

wherein, in formulas (1-6-1) to (1-6-5),
R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;
ring $A^1$ is 1,4-cyclohexylene, 1,4-cyclohexenylene, 1,3-dioxane-2,5-diyl or pyrimidine-2,5-diyl;
$Y^3$, $Y^4$ and $Y^5$ are independently hydrogen, fluorine or chlorine and at least two of $Y^3$, $Y^4$ and $Y^5$ is fluorine or chlorine;
$L^1$, $L^2$, $L^3$, $L^4$ and $L^5$ are independently hydrogen, fluorine or chlorine;
X is fluorine, —C≡N, —CF$_3$ or —OCF$_3$; and
l is 0 or 1.

7. The compound according to claim 1, represented by formula (1-7):

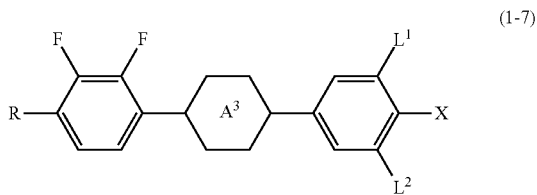

(1-7)

wherein, in formula (1-7),
R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;
ring $A^3$ is 1,4-cyclohexylene, 1,4-cyclohexenylene, 1,3-dioxane-2,5-diyl, pyrimidine-2,5-diyl, naphthalene-2,6-diyl, 1,4-phenylene, 2-fluoro-1,4-phenylene or 2,3-difluoro-1,4-phenylene;
$L^1$ and $L^2$ are independently hydrogen or fluorine; and
X is fluorine, —C≡N, —N=C=S, —SF$_5$, —CF$_3$, —CHF$_2$, —CH$_2$F, —OCF$_3$, —OCHF$_2$, or —OCH$_2$F.

8. The compound according to claim 1, represented by any one of formulas (1-8-1) to (1-8-5):

(1-8-1)

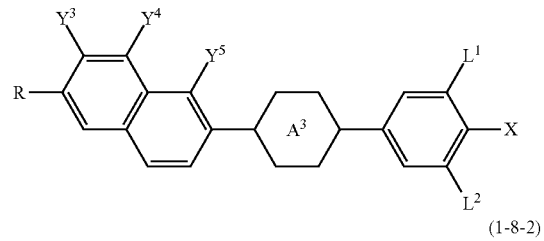

(1-8-2)

(1-8-3)

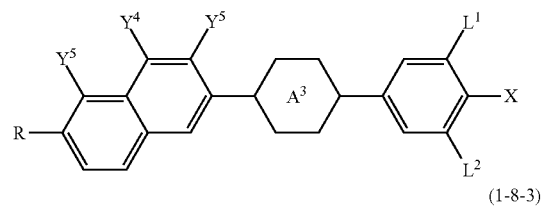

(1-8-4)

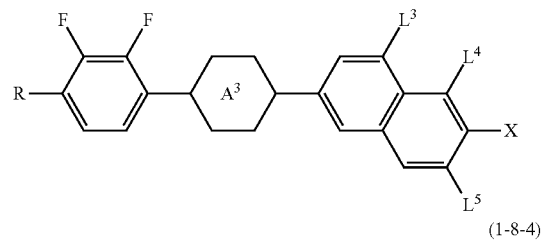

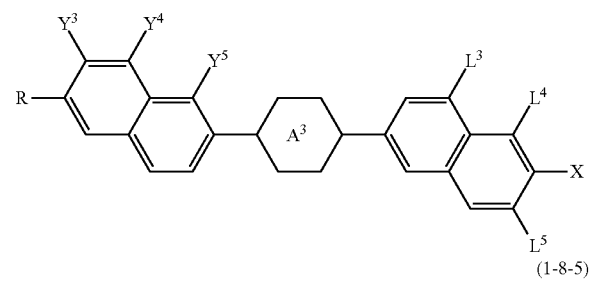

(1-8-5)

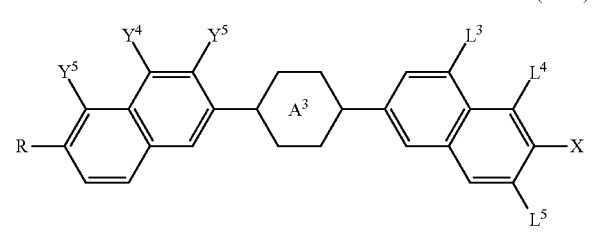

wherein, in formulas (1-8-1) to (1-8-5),
R is hydrogen, alkyl having 1 to 10 carbons, alkenyl having 2 to 10 carbons, alkoxy having 1 to 9 carbons, alkoxyalkyl having 2 to 9 carbons or alkenyloxy having 2 to 9 carbons;
ring $A^3$ is 1,4-cyclohexylene, 1,4-cyclohexenylene, 1,3-dioxane-2,5-diyl, pyrimidine-2,5-diyl, 1,4-phenylene, 2-fluoro-1,4-phenylene or 2,3-difluoro-1,4-phenylene;
$Y^3$, $Y^4$ and $Y^5$ are independently hydrogen, fluorine or chlorine, and at least two of $Y^3$, $Y^4$ and $Y^5$ is fluorine or chlorine;
$L^1$, $L^2$, $L^3$, $L^4$ and $L^5$ are independently hydrogen, fluorine or chlorine; and
X is fluorine, —C≡N, —CF$_3$ or —OCF$_3$.

9. The compound according to claim 1, represented by any one of formulas (1-9-1) to (1-9-12):

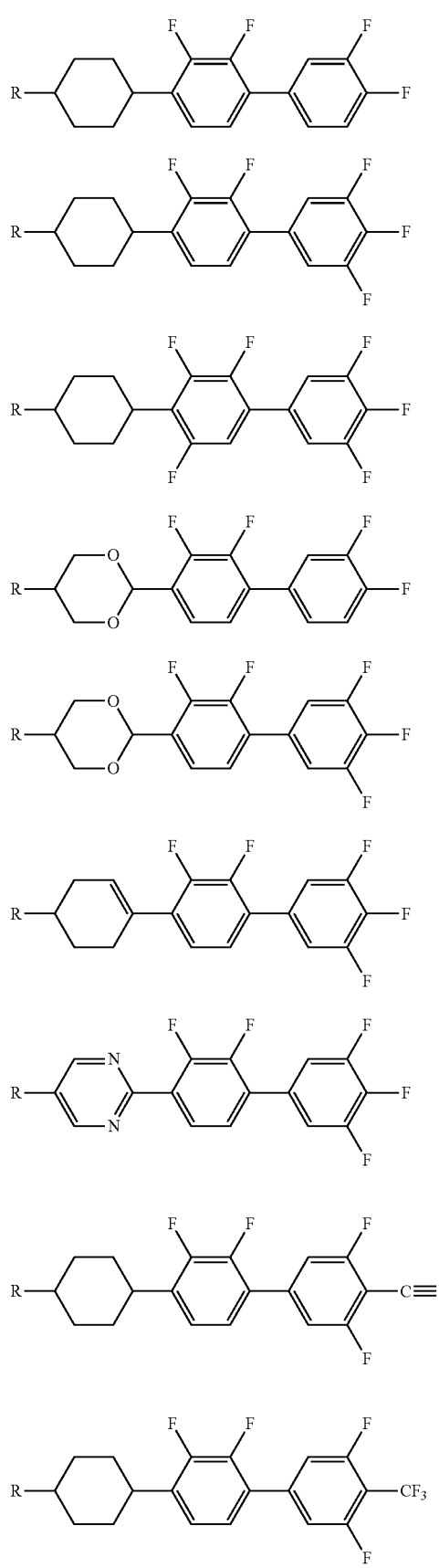
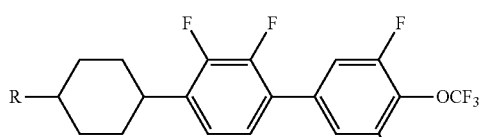
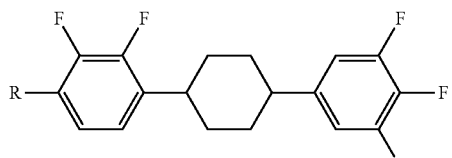
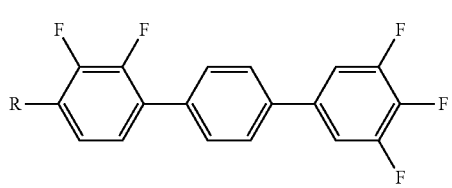
wherein, in formulas (1-9-1) to (1-9-12), R is independently alkyl having 1 to 10 carbons, alkenyl having 2 to 10 carbons or alkoxy having 1 to 9 carbons.
10. The compound according to claim 1, represented by any one of formulas (1-10-1) to (1-10-12):
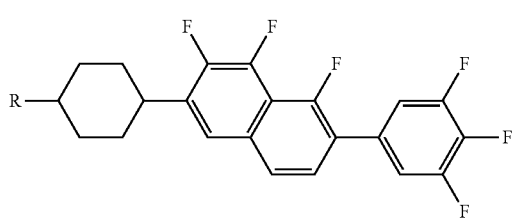
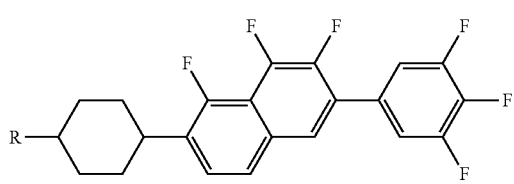
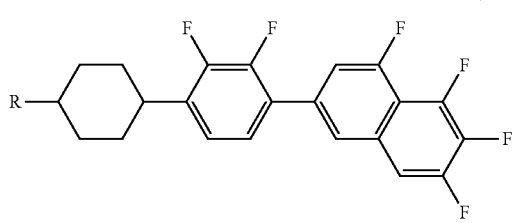

(1-10-4)
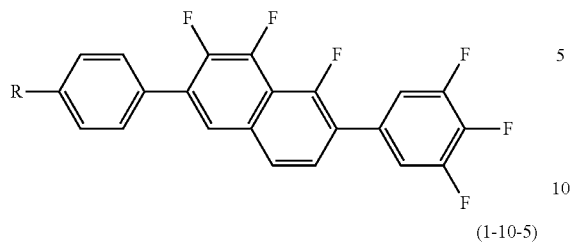

(1-10-5)
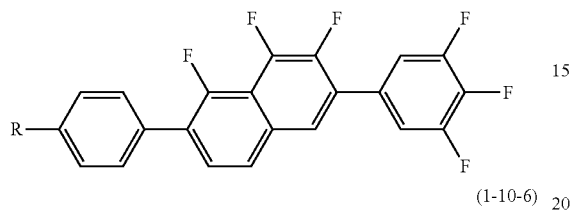

(1-10-6)
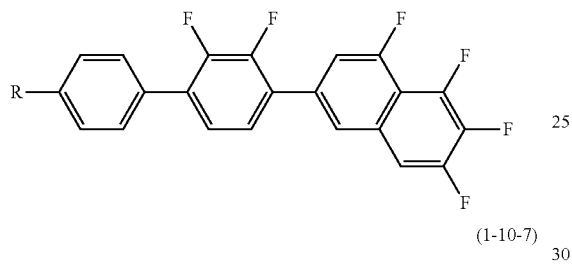

(1-10-7)
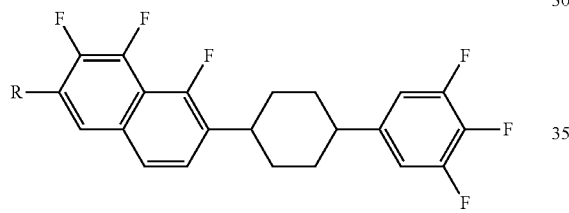

(1-10-8)
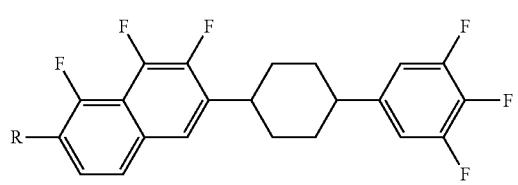

(1-10-9)
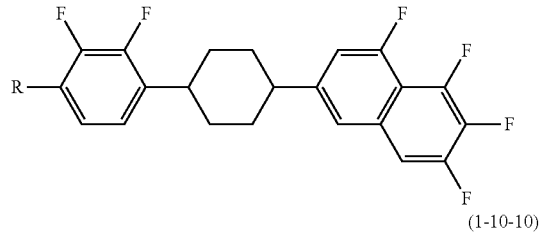

(1-10-10)
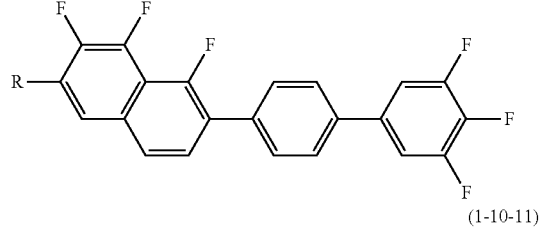

(1-10-11)
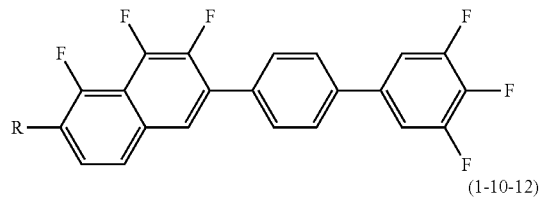

(1-10-12)
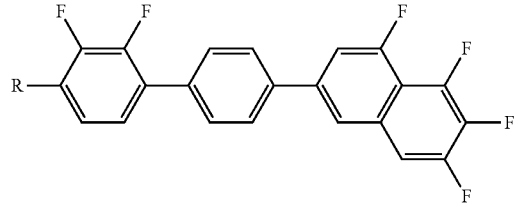

wherein, in formulas (1-10-1) to (1-10-12), R is independently alkyl having 1 to 10 carbons, alkenyl having 2 to 10 carbons or alkoxy having 1 to 9 carbons.

11. A liquid crystal composition containing at least one liquid crystal compound according to claim 1.

12. The liquid crystal composition according to claim 11, further containing at least one compound selected from the group of compounds represented by formulas (2), (3) and (4):

(2)
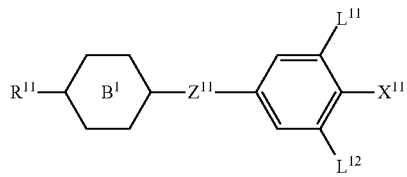

(3)
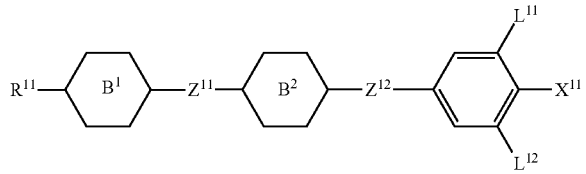

-continued (4)

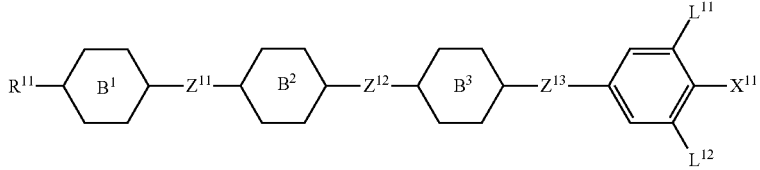

wherein, in formulas (2) to (4), $R^{11}$ is alkyl having 1 to 10 carbons or alkenyl having 2 to 10 carbons, and in the alkyl and the alkenyl, at least one of hydrogen may be replaced by fluorine and at least one of —CH$_2$— may be replaced by —O—;

$X^{11}$ is fluorine, chlorine, —OCF$_3$, —OCHF$_2$, —CF$_3$, —CHF$_2$, —CH$_2$F, —OCF$_2$CHF$_2$ or —OCF$_2$CHFCF$_3$;

ring $B^1$, ring $B^2$ and ring $B^3$ are independently 1,4-cyclohexylene, 1,4-phenylene, 2-fluoro-1,4-phenylene, 2,6-difluoro-1,4-phenylene, tetrahydropyran-2,5-diyl, 1,3-dioxane-2,5-diyl or pyrimidine-2,5-diyl;

$Z^{11}$, $Z^{12}$ and $Z^{13}$ are independently a single bond, —CH$_2$CH$_2$—, —CH=CH—, —C≡C—, —COO—, —CF$_2$O—, —OCF$_2$—, —CH$_2$O— or —(CH$_2$)$_4$—; and $L^{11}$ and $L^{12}$ are independently hydrogen or fluorine.

13. The liquid crystal composition according to claim 11, further containing at least one compound selected from the group of compounds represented by formula (5):

(5)

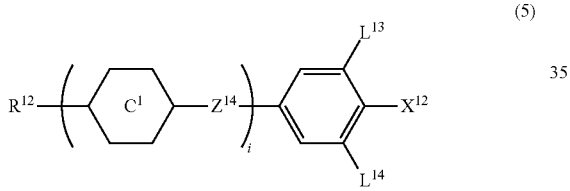

wherein, in formula (5), $R^{12}$ is alkyl having 1 to 10 carbons or alkenyl having 2 to 10 carbons, and in the alkyl and the alkenyl, at least one of hydrogen may be replaced by fluorine and at least one of —CH$_2$— may be replaced by —O—;

$X^{12}$ is —C≡N or —C≡C—C≡N;

ring $C^1$ is 1,4-cyclohexylene, 1,4-phenylene in which at least one of hydrogen may be replaced by fluorine, tetrahydropyran-2,5-diyl, 1,3-dioxane-2,5-diyl or pyrimidine-2,5-diyl;

$Z^{14}$ is a single bond, —CH$_2$CH$_2$—, —C≡C—, —COO—, —CF$_2$O—, —OCF$_2$—, or —CH$_2$O—, however, at least one of $Z^{14}$ is —CH$_2$CH$_2$—, —C≡C—, —COO—, —CF$_2$O—, —OCF$_2$—, or —CH$_2$O—;

$L^{13}$ and $L^{14}$ are independently hydrogen or fluorine; and i is 1, 2, 3 or 4.

14. The liquid crystal composition according to claim 11, further containing at least one compound selected from the group of compounds represented by formulas (6) to (12):

(6)

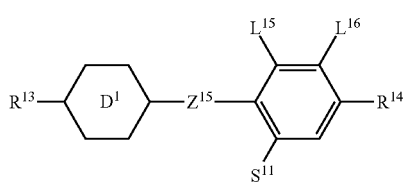

(7)

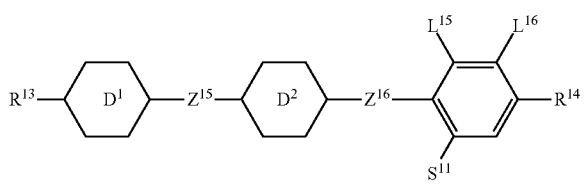

(8)

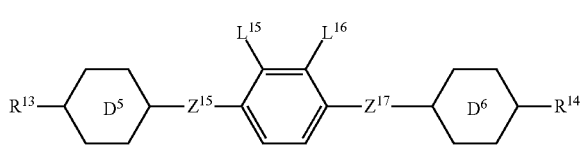

-continued (9)
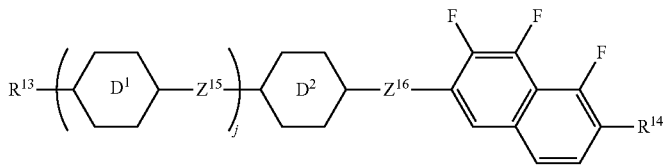

(10)
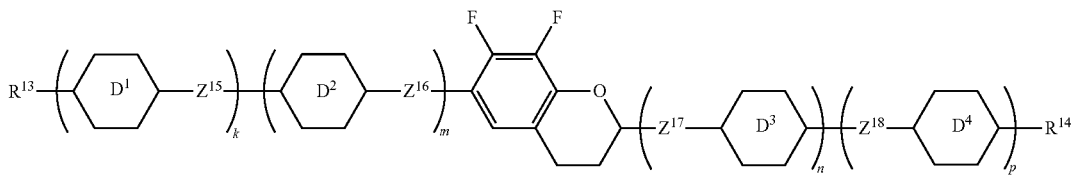

(11)
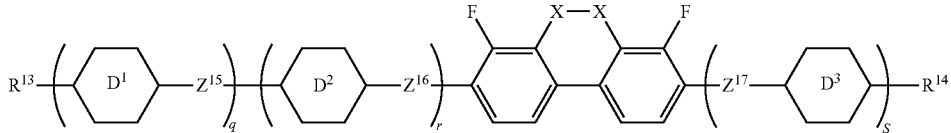

(12)
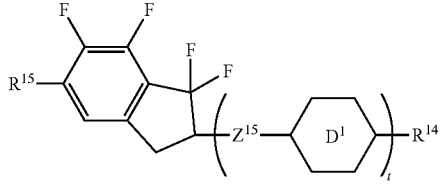

wherein, in formulas (6) to (12),
$R^{13}$ and $R^{14}$ are independently alkyl having 1 to 10 carbons or alkenyl having 2 to 10 carbons, and in the alkyl and the alkenyl, at least one of —CH$_2$— may be replaced by —O— and at least one of hydrogen may be replaced by fluorine;
$R^{15}$ is hydrogen, fluorine, alkyl having 1 to 10 carbons or alkenyl having 2 to 10 carbons, and in the alkyl and the alkenyl, at least one of —CH$_2$— may be replaced by —O— and at least one of hydrogen may be replaced by fluorine;
$S^{11}$ is hydrogen or methyl;
X is —CF$_2$—, —O— or —CHF—;
ring D$^1$, ring D$^2$, ring D$^3$ and ring D$^4$ are independently 1,4-cyclohexylene, 1,4-cyclohexenylene, 1,4-phenylene in which at least one of hydrogen may be replaced by fluorine, tetrahydropyran-2,5-diyl or decahydronaphthalene-2,6-diyl;
ring D$^5$ and ring D$^6$ are independently 1,4-cyclohexylene, 1,4-cyclohexenylene, 1,4-phenylene, tetrahydropyran-2,5-diyl or decahydronaphthalene-2,6-diyl;
$Z^{15}$, $Z^{16}$, $Z^{17}$ and $Z^{18}$ are independently a single bond, —CH$_2$CH$_2$—, —COO—, —CH$_2$O—, —OCF$_2$— or —OCF$_2$CH$_2$CH$_2$—;
$L^{15}$ and $L^{16}$ are independently fluorine or chlorine; and
j, k, m, n, p, q, r and s are independently 0 or 1, a sum of k, m, n and p is 1 or 2, a sum of q, r and s is 0, 1, 2 or 3, and t is 1, 2 or 3.

15. The liquid crystal composition according to claim 11, further containing at least one compound selected from the group of compounds represented by formulas (13) to (15):

(13)
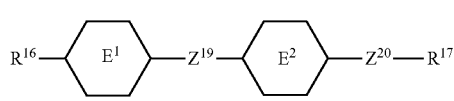

(14)
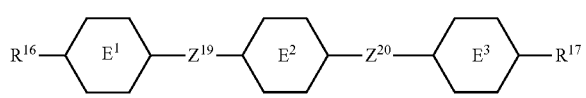

(15)
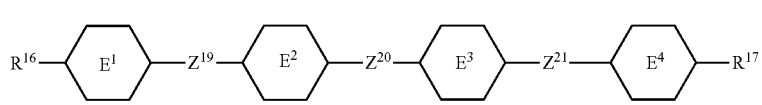

wherein, in formulas (13) to (15), $R^{16}$ and $R^{17}$ are independently alkyl having 1 to 10 carbons or alkenyl having 2 to 10 carbons, and in the alkyl and the alkenyl, at least one of —$CH_2$— may be replaced by —O—, and at least one of hydrogen may be replaced by fluorine;

ring $E^1$, ring $E^2$, ring $E^3$ and ring $E^4$ are independently 1,4-cyclohexylene, 1,4-phenylene, 2-fluoro-1,4-phenylene, 2,5-difluoro-1,4-phenylene or pyrimidine-2,5-diyl; and $Z^{19}$, $Z^{20}$ and $Z^{21}$ are independently a single bond, —$CH_2CH_2$—, —CH=CH—, —C≡C— or —COO—.

16. The liquid crystal composition according to claim 11, further containing at least one optically active compound and/or polymerizable compound.

17. The liquid crystal composition according to claim 11, further containing at least one antioxidant and/or ultraviolet light absorber.

18. A liquid crystal display device, including the liquid crystal composition according to claim 11.

* * * * *